(12) United States Patent
Moriya et al.

(10) Patent No.: US 10,428,359 B2
(45) Date of Patent: Oct. 1, 2019

(54) METHOD FOR PRODUCING L-AMINO ACID

(71) Applicant: AJINOMOTO CO., INC., Tokyo (JP)

(72) Inventors: Mika Moriya, Kanagawa (JP);
Kazuyuki Hayashi, Kanagawa (JP);
Akari Yokokawa, Kanagawa (JP)

(73) Assignee: AJINOMOTO CO, INC., Tokyo (JP)

( * ) Notice: Subject to any disclaimer, the term of this patent is extended or adjusted under 35 U.S.C. 154(b) by 0 days.

(21) Appl. No.: 15/717,042

(22) Filed: Sep. 27, 2017

(65) Prior Publication Data
US 2018/0094285 A1 Apr. 5, 2018

(30) Foreign Application Priority Data
Oct. 3, 2016 (JP) ................................ 2016-195818

(51) Int. Cl.
*C12P 13/20* (2006.01)
*C07C 227/28* (2006.01)
*C12P 13/08* (2006.01)
*C12P 13/14* (2006.01)
*C07K 14/34* (2006.01)
*C12N 9/88* (2006.01)
*C07C 229/36* (2006.01)
*C12N 1/20* (2006.01)
*C12N 15/66* (2006.01)
*C12Q 1/686* (2018.01)

(52) U.S. Cl.
CPC ............ *C12P 13/20* (2013.01); *C07C 227/28* (2013.01); *C07K 14/34* (2013.01); *C12N 9/88* (2013.01); *C12P 13/08* (2013.01); *C12P 13/14* (2013.01); *C07C 229/36* (2013.01); *C12N 1/20* (2013.01); *C12N 15/66* (2013.01); *C12Q 1/686* (2013.01)

(58) Field of Classification Search
None
See application file for complete search history.

(56) References Cited

U.S. PATENT DOCUMENTS

| 8,722,370 | B2 | 5/2014 | Filippov et al. |
| 9,487,806 | B2 | 11/2016 | Toyazaki et al. |
| 9,506,094 | B2 | 11/2016 | Hirano et al. |
| 2002/0106759 | A1 | 8/2002 | Farwick et al. |
| 2006/0141588 | A1* | 6/2006 | Nakamura ............ C07K 14/34 435/110 |
| 2010/0099152 | A1* | 4/2010 | Chinen ................ C12N 9/1029 435/107 |
| 2017/0121743 | A1 | 5/2017 | Hirano et al. |

FOREIGN PATENT DOCUMENTS

| WO | WO-200224915 A1 * | 3/2002 |
| WO | WO03/054206 A1 | 7/2003 |
| WO | WO2006/016705 A1 | 2/2006 |
| WO | WO2006/070944 A2 | 7/2006 |

OTHER PUBLICATIONS

Six et al. *Escherichia coli* Possesses Two Homologous Anaerobic C4-Dicarboxylate Membrane Transporters (DcuA and DcuB) Distinct from the Aerobic Dicarboxylate Transport System (Dct). J. Bacteriol. (1994), 176(21): 6470-6478.*

Karinou, E., et al., "The *Escherichia coil* SLC26 homologue YchM (DauA) is a C4-dicarboxylic acid transporter," Mol. Microbiol. 2013;87(3):623-640.

Janausch, I. G., et al., "C4-dicarboxylate carriers and sensors in bacteria," Biochim. Biophys. Acta 2002;1553:39-56.

Nakamura, J., et al., "Mutations of the Corynebacterium glutamicum NCgl1221 Gene, Encoding a Mechanosensitive Channel Homolog, Induce L-Glutamic Acid Production," Appl. Environmen. Microbiol. 2007;73(14):4491-4498.

Youn, J.-W., et al., "Characterization of the Dicarboxylate Transporter DctA in Corynebacterium glutamicum," J. Bacteriol. 2009;191(17):5480-5488.

Search Report from French Patent App. No. 1759214 (dated Mar. 28, 2019) and English language translation thereof.

* cited by examiner

*Primary Examiner* — Iqbal H Chowdhury
(74) *Attorney, Agent, or Firm* — Cermak Nakajima & McGowan LLP; Shelly Guest Cermak

(57) ABSTRACT

A method for producing an L-amino acid such as L-glutamic acid is provided. An L-amino acid is produced by culturing a bacterium having an L-amino acid-producing ability, which has been modified so that the activity of a C4-dicarboxylic acid-uptake carrier such as DctA, DcuA, and DcuB is increased, in a medium, and collecting the L-amino acid from the medium or cells of the bacterium.

23 Claims, 1 Drawing Sheet
Specification includes a Sequence Listing.

```
                            SEQUENCE LISTING

<160> NUMBER OF SEQ ID NOS: 22

<210> SEQ ID NO 1
<211> LENGTH: 50
<212> TYPE: DNA
<213> ORGANISM: Artificial Sequence
<220> FEATURE:
<223> OTHER INFORMATION: primer

<400> SEQUENCE: 1
ccaagcttgc atgccaggag gattataatg gattcaaaca cagaatcttc            50

<210> SEQ ID NO 2
<211> LENGTH: 39
<212> TYPE: DNA
<213> ORGANISM: Artificial Sequence
<220> FEATURE:
<223> OTHER INFORMATION: primer
```

-continued

<400> SEQUENCE: 2
cggtacccgg ggatcctagt ggtcttcttc taactccac                           39

<210> SEQ ID NO 3
<211> LENGTH: 52
<212> TYPE: DNA
<213> ORGANISM: Artificial Sequence
<220> FEATURE:
<223> OTHER INFORMATION: primer

<400> SEQUENCE: 3
ccaagcttgc atgccaggag gattataatg aaaacctctc tgtttaaaag cc            52

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4
cggtacccgg ggatcttaag aggataattc gtgcg                               35

<210> SEQ ID NO 5
<211> LENGTH: 52
<212> TYPE: DNA
<213> ORGANISM: Artificial Sequence
<220> FEATURE:
<223> OTHER INFORMATION: primer

<400> SEQUENCE: 5
ccaagcttgc atgccaggag gattataatg ctagttgtag aactcatcat ag            52

<210> SEQ ID NO 6
<211> LENGTH: 40
<212> TYPE: DNA
<213> ORGANISM: Artificial Sequence
<220> FEATURE:
<223> OTHER INFORMATION: primer

<400> SEQUENCE: 6
cggtacccgg ggatcttaca gcatgaagct acccagcacg                          40

<210> SEQ ID NO 7
<211> LENGTH: 51
<212> TYPE: DNA
<213> ORGANISM: Artificial Sequence
<220> FEATURE:
<223> OTHER INFORMATION: primer

<400> SEQUENCE: 7
ccaagcttgc atgccaggag gattataatg ttatttacta tccaacttat c             51

<210> SEQ ID NO 8
<211> LENGTH: 40
<212> TYPE: DNA
<213> ORGANISM: Artificial Sequence
<220> FEATURE:
<223> OTHER INFORMATION: primer

<400> SEQUENCE: 8
cggtacccgg ggatcttata agaacccgta catcgcggcg                          40

<210> SEQ ID NO 9

<211> LENGTH: 1602
<212> TYPE: DNA
<213> ORGANISM: Corynebacterium glutamicum

<400> SEQUENCE: 9

```
atgattttag gcgtacccat tcaatatttg ctctattcat tgtggaattg gattgtcgat      60
accggttttg atgtagcaat tatcctggtc ttggcgtttt tgattccacg tatcggccga     120
ctggccatgc gtattatcaa gcagcgagtg gagtctgcag ccgatgcgga caccactaag     180
aaccagctcg cgttcgctgg cgttggcgtt tatatcgcgc aaattgtggc gttttcatg      240
cttgccgtct ccgcgatgca ggcttttggt ttctctctcg cgggcgctgc gattccggca     300
accattgcgt cagctgccat tggtcttggt gcgcagtcga ttgttgcgga cttcttggcc     360
ggattttca tcctgacgga aaagcaattc ggcgtgggtg actgggtgcg ctttgagggc      420
aacggcatcg ttgttgaagg caccgtcatt gagatcacca tgcgcgcgac caaaattcgc     480
acgattgcac aagagaccgt gatcatcccg aactccacgg cgaaagtgtg catcaacaat     540
tctaataact ggtcgcgtgc ggttgtcgtt attccgatcc ccatgttggg ttctgaaaac     600
atcacagatg tcatcgcgcg ctctgaagct gcgactcgtc gcgcacttgg ccaggagaaa     660
atcgcaccgg aaatcctcgg tgaactcgat gtgcacccag ccacggaagt cacaccgcca     720
acggtggtcg gcatgccgtg gatggtcacc atgcgttttc ctgtgcaagt caccgccggc     780
aatcaatggc tggtcgaacg cgccatccgc acagaaatca tcaacgaatt ctgggaagaa     840
tacggcagcg caaccactac atcgggaacc ctcattgatt ccttacacgt gagcatgaa      900
gagccaaaga cctcgcttat cgacgcctcc cccaggctc ttaaggaacc gaagccggag      960
gctgcggcga cggttgcatc gctagctgca tcgtctaacg acgatgcaga caatgcagac    1020
gcctcggcga tcaatgcagg caatccagag aaggaacttg attccgatgt gctggaacaa    1080
gaactctcca gcgaagaacc ggaagaaaca gcaaaaccag atcactctct ccgaggcttc    1140
ttccgcactg attactaccc aaatcggtgg cagaagatcc tgtcgtttgg cggacgtgtc    1200
cgcatgagca cttccctgtt gttgggtgcg ctgctcttgc tgtcactatt taaggtcatg    1260
actgtggaac caagtgagaa ttggcaaaac tccagtggat ggctgtcacc aagcactgcc    1320
acctcaactg cggtgaccac ctccgaaact tccgcgccag caagcacgcc ttcgatgaca    1380
gtgcccacta cggtggagga acccaacg atggaatcta gcgtcgaaac gcagcaggaa     1440
acctcaaccc ctgcaaccgc aacgccccag cgagccgaca ccatcgaacc gaccgaggaa    1500
gccacgtcgc aggaggaaac gactgcatcg cagacgcagt ctccagcagt ggaagcacca    1560
accgcggtcc aagaaacagt tgcgccgacg tccaccccctt ag                      1602
```

<210> SEQ ID NO 10
<211> LENGTH: 533
<212> TYPE: PRT
<213> ORGANISM: Corynebacterium glutamicum

<400> SEQUENCE: 10

```
Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Gln
        35                  40                  45

Arg Val Glu Ser Ala Ala Asp Ala Asp Thr Thr Lys Asn Gln Leu Ala
    50                  55                  60
```

-continued

```
Phe Ala Gly Val Gly Val Tyr Ile Ala Gln Ile Val Ala Phe Phe Met
 65                  70                  75                  80

Leu Ala Val Ser Ala Met Gln Ala Phe Gly Phe Ser Leu Ala Gly Ala
                 85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
            180                 185                 190        Pro

Ile Pro Met Leu Gly Ser Glu Asn Ile Thr Asp Val Ile Ala Arg Ser
        195                 200                 205

Glu Ala Ala Thr Arg Arg Ala Leu Gly Gln Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Asn Glu Phe Trp Glu Glu Tyr Gly Ser Ala Thr Thr Thr Ser
        275                 280                 285

Gly Thr Leu Ile Asp Ser Leu His Val Glu His Glu Pro Lys Thr
    290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
            340                 345                 350

Leu Asp Ser Asp Val Leu Glu Gln Glu Leu Ser Ser Glu Glu Pro Glu
        355                 360                 365

Glu Thr Ala Lys Pro Asp His Ser Leu Arg Gly Phe Phe Arg Thr Asp
    370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415

Phe Lys Val Met Thr Val Glu Pro Ser Glu Asn Trp Gln Asn Ser Ser
            420                 425                 430

Gly Trp Leu Ser Pro Ser Thr Ala Thr Ser Thr Ala Val Thr Thr Ser
        435                 440                 445

Glu Thr Ser Ala Pro Ala Ser Thr Pro Ser Met Thr Val Pro Thr Thr
    450                 455                 460

Val Glu Glu Thr Pro Thr Met Glu Ser Ser Val Glu Thr Gln Gln Glu
465                 470                 475                 480
```

```
Thr Ser Thr Pro Ala Thr Ala Thr Pro Gln Arg Ala Asp Thr Ile Glu
            485                 490                 495

Pro Thr Glu Glu Ala Thr Ser Gln Glu Glu Thr Thr Ala Ser Gln Thr
        500                 505                 510

Gln Ser Pro Ala Val Glu Ala Pro Thr Ala Val Gln Glu Thr Val Ala
            515                 520                 525

Pro Thr Ser Thr Pro
        530

<210> SEQ ID NO 11
<211> LENGTH: 3063
<212> TYPE: DNA
<213> ORGANISM: Corynebacterium glutamicum
<220> FEATURE:
<221> NAME/KEY: CDS
<222> LOCATION: (1)..(1269)

<400> SEQUENCE: 11
```

| | | | | | | | | | | | | | | | | |
|---|---|---|---|---|---|---|---|---|---|---|---|---|---|---|---|---|
| atg | att | tta | ggc | gta | ccc | att | caa | tat | ttg | ctc | tat | tca | ttg | tgg | aat | 48 |
| Met | Ile | Leu | Gly | Val | Pro | Ile | Gln | Tyr | Leu | Leu | Tyr | Ser | Leu | Trp | Asn | |
| 1 | | | | 5 | | | | | 10 | | | | | 15 | | |
| tgg | att | gtc | gat | acc | ggt | ttt | gat | gta | gca | att | atc | ctg | gtc | ttg | gcg | 96 |
| Trp | Ile | Val | Asp | Thr | Gly | Phe | Asp | Val | Ala | Ile | Ile | Leu | Val | Leu | Ala | |
| | | | 20 | | | | | 25 | | | | | 30 | | | |
| ttt | ttg | att | cca | cgt | atc | ggc | cga | ctg | gcc | atg | cgt | att | atc | aag | cag | 144 |
| Phe | Leu | Ile | Pro | Arg | Ile | Gly | Arg | Leu | Ala | Met | Arg | Ile | Ile | Lys | Gln | |
| | | 35 | | | | | 40 | | | | | 45 | | | | |
| cga | gtg | gag | tct | gca | gcc | gat | gcg | gac | acc | act | aag | aac | cag | ctc | gcg | 192 |
| Arg | Val | Glu | Ser | Ala | Ala | Asp | Ala | Asp | Thr | Thr | Lys | Asn | Gln | Leu | Ala | |
| | 50 | | | | | 55 | | | | | 60 | | | | | |
| ttc | gct | ggc | gtt | ggc | gtt | tat | atc | gcg | caa | att | gtg | gcg | ttt | ttc | atg | 240 |
| Phe | Ala | Gly | Val | Gly | Val | Tyr | Ile | Ala | Gln | Ile | Val | Ala | Phe | Phe | Met | |
| 65 | | | | | 70 | | | | | 75 | | | | | 80 | |
| ctt | gcc | gtc | tcc | gcg | atg | cag | gct | ttt | ggt | ttc | tct | ctc | gcg | ggc | gct | 288 |
| Leu | Ala | Val | Ser | Ala | Met | Gln | Ala | Phe | Gly | Phe | Ser | Leu | Ala | Gly | Ala | |
| | | | | 85 | | | | | 90 | | | | | 95 | | |
| gcg | att | ccg | gca | acc | att | gcg | tca | gct | gcc | att | ggt | ctt | ggt | gcg | cag | 336 |
| Ala | Ile | Pro | Ala | Thr | Ile | Ala | Ser | Ala | Ala | Ile | Gly | Leu | Gly | Ala | Gln | |
| | | | 100 | | | | | 105 | | | | | 110 | | | |
| tcg | att | gtt | gcg | gac | ttc | ttg | gcc | gga | ttt | ttc | atc | ctg | acg | gaa | aag | 384 |
| Ser | Ile | Val | Ala | Asp | Phe | Leu | Ala | Gly | Phe | Phe | Ile | Leu | Thr | Glu | Lys | |
| | | 115 | | | | | 120 | | | | | 125 | | | | |
| caa | ttc | ggc | gtg | ggt | gac | tgg | gtg | cgc | ttt | gag | ggc | aac | ggc | atc | gtt | 432 |
| Gln | Phe | Gly | Val | Gly | Asp | Trp | Val | Arg | Phe | Glu | Gly | Asn | Gly | Ile | Val | |
| | 130 | | | | | 135 | | | | | 140 | | | | | |
| gtt | gaa | ggc | acc | gtc | att | gag | atc | acc | atg | cgc | gcg | acc | aaa | att | cgc | 480 |
| Val | Glu | Gly | Thr | Val | Ile | Glu | Ile | Thr | Met | Arg | Ala | Thr | Lys | Ile | Arg | |
| 145 | | | | | 150 | | | | | 155 | | | | | 160 | |
| acg | att | gca | caa | gag | acc | gtg | atc | atc | ccg | aac | tcc | acg | gcg | aaa | gtg | 528 |
| Thr | Ile | Ala | Gln | Glu | Thr | Val | Ile | Ile | Pro | Asn | Ser | Thr | Ala | Lys | Val | |
| | | | | 165 | | | | | 170 | | | | | 175 | | |
| tgc | atc | aac | aat | tct | aat | aac | tgg | tcg | cgt | gcg | gtt | gtc | gtt | att | ccg | 576 |
| Cys | Ile | Asn | Asn | Ser | Asn | Asn | Trp | Ser | Arg | Ala | Val | Val | Val | Ile | Pro | |
| | | | 180 | | | | | 185 | | | | | 190 | | | |
| atc | ccc | atg | ttg | ggt | tct | gaa | aac | atc | aca | gat | gtc | atc | gcg | cgc | tct | 624 |
| Ile | Pro | Met | Leu | Gly | Ser | Glu | Asn | Ile | Thr | Asp | Val | Ile | Ala | Arg | Ser | |
| | | | 195 | | | | | 200 | | | | | 205 | | | |
| gaa | gct | gcg | act | cgt | cgc | gca | ctt | ggc | cag | gag | aaa | atc | gca | ccg | gaa | 672 |
| Glu | Ala | Ala | Thr | Arg | Arg | Ala | Leu | Gly | Gln | Glu | Lys | Ile | Ala | Pro | Glu | |
| | 210 | | | | | 215 | | | | | 220 | | | | | |

```
atc ctc ggt gaa ctc gat gtg cac cca gcc acg gaa gtc aca ccg cca      720
Ile Leu Gly Glu Leu Asp Val His Pro Ala Thr Glu Val Thr Pro Pro
225                 230                 235                 240 acg gtg gtc ggc atg ccg tgg atg gtc acc atg cgt ttc ctc gtg caa      768
Thr Val Val Gly Met Pro Trp Met Val Thr Met Arg Phe Leu Val Gln
            245                 250                 255 gtc acc gcc ggc aat caa tgg ctg gtc gaa cgc gcc atc cgc aca gaa      816
Val Thr Ala Gly Asn Gln Trp Leu Val Glu Arg Ala Ile Arg Thr Glu
    260                 265                 270 atc atc aac gaa ttc tgg gaa gaa tac ggc agc gca acc act aca tcg      864
Ile Ile Asn Glu Phe Trp Glu Glu Tyr Gly Ser Ala Thr Thr Thr Ser
275                 280                 285 gga acc ctc att gat tcc tta cac gtt gag cat gaa gag cca aag acc      912
Gly Thr Leu Ile Asp Ser Leu His Val Glu His Glu Glu Pro Lys Thr
        290                 295                 300 tcg ctt atc gac gcc tcc ccc cag gct ctt aag gaa ccg aag ccg gag      960
Ser Leu Ile Asp Ala Ser Pro Gln Ala Leu Lys Glu Pro Lys Pro Glu
305                 310                 315                 320 gct gcg gcg acg gtt gca tcg cta gct gca tcg tct aac gac gat gca     1008
Ala Ala Ala Thr Val Ala Ser Leu Ala Ala Ser Ser Asn Asp Asp Ala
                325                 330                 335 gac aat gca gac gcc tcg gcg atc aat gca ggc aat cca gag aag gaa     1056
Asp Asn Ala Asp Ala Ser Ala Ile Asn Ala Gly Asn Pro Glu Lys Glu
            340                 345                 350 ctt gat tcc gat gtg ctg gaa caa gaa ctc tcc agc gaa gaa ccg gaa     1104
Leu Asp Ser Asp Val Leu Glu Gln Glu Leu Ser Ser Glu Glu Pro Glu
        355                 360                 365 gaa aca gca aaa cca gat cac tct ctc cga ggc ttc ttc cgc act gat     1152
Glu Thr Ala Lys Pro Asp His Ser Leu Arg Gly Phe Phe Arg Thr Asp
370                 375                 380 tac tac cca aat cgg tgg cag aag atc ctg tcg ttt ggc gga cgt gtc     1200
Tyr Tyr Pro Asn Arg Trp Gln Lys Ile Leu Ser Phe Gly Gly Arg Val
385                 390                 395                 400 cgc atg agc act tcc ctg ttg ttg ggt gcg ctg ctc ttg ctg tca cta     1248
Arg Met Ser Thr Ser Leu Leu Leu Gly Ala Leu Leu Leu Leu Ser Leu
                405                 410                 415 ttt aag ggg ctc ttc ctg ttt tagagtgcat tgatcttatg gaccaactgc        1299
Phe Lys Gly Leu Phe Leu Phe
            420 cctgaatgga taaggcaccg cagaatgtag tggttcaaat tacggaaacc tagagcaatc   1359 ccacgcaaat gctccaaccg tccgttgatc gcttcgaccg gaccgttgga gacaccaaca   1419 tcgaaatacg ccaacacatc accaagtcgt ttaaacaaac tacgacccaa ctgcgcgagt   1479 tccttattcg gccccttcaa cacccgaagc tgatcaataa tggtccgcat tttcttcttc   1539 gcttcacgct tattacccat ctgataacaa tcaataatcg cctgatacgc aagccacgca   1599 agctttaaca ccccgtagtc tttgtcatac gcccacaact gctccaagct ttcttgctga   1659 cgaggactca accacttgtg cgtggtcaac aaggtcttcc ggtttttata caacggatcc   1719 tggcttaaac cacgacgctg gtatttctcc cgctggagcg gttgccggca ggcggtgagc   1779 ttgtcaccag caagccgcac aacatggaat ggatccatca cgcgacgagc agaaggaatg   1839 agttctttac ttgctgtggc gtagccttgg aacccatcca tggacacgat ccgtatctga   1899 ttgcggaact gttcaccgcg ggaaccaagc caggaccgta agcatcagc actacgacct    1959 gggacgacat ctaataaccg ggcaggacac cgtgagtcat accgatgccc ggtcatatcg   2019 acaatcacgg tgacaaaccc atcaccatgc ttagccctat tatgtgacca cttatgctca   2079 tccaccccaa tgacatacac tccatcaaga tggtgaggat cgttatagac cagctcacgg   2139
```

```
cacatatcga gggctagttg gcaggttaaa tcccaccta gcccaagtgc tttcgcggtt    2199
gcgtgaacac tcatccggtc aatagcaagg cgttgcaaaa tccagcgggt gacccggtgg    2259
gtgaccttt taccgtggtc agcgcagctt agttctgctt ggaaatactt ttgcttacat     2319
gtcgggttgg tgcagcggta gcgaggtaga cggataaaca gtttggtggg aaacccgacg    2379
atgggtaaat caatgagcat ccggtgggtg tgatgacgaa acaccccagg ttgggagcat    2439
tctgggcagg tggaggtata gtcgagtgcg tctgcttcga tcagggtgta atcacctgca    2499
tcggaagcgc cggtgatggt gagtcctagt tccgcagtgc ggcagatggt gtcagcgatg    2559
atgttgccgg tagacttcat gggtagagcc ttttgttggt gtttggttag cttagatacc    2619
taaaccttaa ccctgacaaa aggctcgttt attttcgggt ctacaccgct agcccaggtt    2679
ctgtgatgta cccaaaaacc ggaagggcca tttaaggtca tgactgtgga accaagtgag    2739
aattggcaaa actccagtgg atggctgtca ccaagcactg ccacctcaac tgcggtgacc    2799
acctccgaaa cttccgcgcc agcaagcacg ccttcgatga cagtgcccac tacggtggag    2859
gagaccccaa cgatggaatc tagcgtcgaa acgcagcagg aaacctcaac ccctgcaacc    2919
gcaacgcccc agcgagccga caccatcgaa ccgaccgagg aagccacgtc gcaggaggaa    2979
acgactgcat cgcagacgca gtctccagca gtggaagcac caaccgcggt ccaagaaaca    3039
gttgcgccga cgtccacccc ttag                                           3063

<210> SEQ ID NO 12
<211> LENGTH: 423
<212> TYPE: PRT
<213> ORGANISM: Corynebacterium glutamicum

<400> SEQUENCE: 12

Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Gln
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
        195                 200                 205
```

```
Glu Ala Ala Thr Arg Arg Ala Leu Gly Gln Glu Lys Ile Ala Pro Glu
    210                 215                 220
Ile Leu Gly Glu Leu Asp Val His Pro Ala Thr Glu Val Thr Pro Pro
225                 230                 235                 240
Thr Val Val Gly Met Pro Trp Met Val Thr Met Arg Phe Leu Val Gln
                245                 250                 255
Val Thr Ala Gly Asn Gln Trp Leu Val Glu Arg Ala Ile Arg Thr Glu
            260                 265                 270
Ile Ile Asn Glu Phe Trp Glu Glu Tyr Gly Ser Ala Thr Thr Thr Ser
        275                 280                 285
Gly Thr Leu Ile Asp Ser Leu His Val Glu His Glu Glu Pro Lys Thr
    290                 295                 300
Ser Leu Ile Asp Ala Ser Pro Gln Ala Leu Lys Glu Pro Lys Pro Glu
305                 310                 315                 320
Ala Ala Ala Thr Val Ala Ser Leu Ala Ala Ser Ser Asn Asp Ala
                325                 330                 335
Asp Asn Ala Asp Ala Ser Ala Ile Asn Ala Gly Asn Pro Glu Lys Glu
            340                 345                 350
Leu Asp Ser Asp Val Leu Glu Gln Glu Leu Ser Ser Glu Glu Pro Glu
        355                 360                 365
Glu Thr Ala Lys Pro Asp His Ser Leu Arg Gly Phe Phe Arg Thr Asp
    370                 375                 380
Tyr Tyr Pro Asn Arg Trp Gln Lys Ile Leu Ser Phe Gly Gly Arg Val
385                 390                 395                 400
Arg Met Ser Thr Ser Leu Leu Leu Gly Ala Leu Leu Leu Leu Ser Leu
                405                 410                 415
Phe Lys Gly Leu Phe Leu Phe
            420

<210> SEQ ID NO 13
<211> LENGTH: 2478
<212> TYPE: DNA
<213> ORGANISM: Bifidobacterium longum

<400> SEQUENCE: 13
atgacgagtc ctgttattgg cacccctggg aagaagctca acgctccggt ttccgaggaa      60
gccctcgaag gcgttgacaa gtactggcgc gttgccaact accttccat cggccagatt     120
tatctgcgtt ccaacccgct gatgaaggag cccttcaccc gcgaagatgt gaagcaccgt     180
ctggtgggcc actggggcac tacccctggc ctgaacttcc tcatcggcca catcaaccgt     240
ttcattgctg accacggcca gaacaccgtg atcatcatgg gcccgggcca cggtggcccg     300
gccggtacct cccagtccta cctggacggc acctacaccg agaccttccc gaagatcacc     360
aaggacgaag ctggtctgca gaagttcttc cgtcagttct cttacccggg cggcattccg     420
tcccacttcg ctccggagac cccgggctcc atccacgagg tggtgagct gggttacgct     480
ctgtcccacg cttacggcgc catcatggac aacccgagcc tgtttgtccc ggccatcgtc     540
ggcgacggcg aggctgagac cggcccgctg ctaccggct ggcagtccaa caagctcgtg     600
aacccgcgca ccgacggtat cgtgctgccg atcctgcacc tcaacggcta caagatcgcc     660
aacccgacca tcctgtcccg catctccgac gaagagctcc acgagttctt ccacggcatg     720
ggttacgagc cctacgagtt cgtcgctggc ttcgatgatg aggaccacat gtccatccac     780
cgtcgcttcg ccgagctgtg ggagaccatc tgggacgaga tctgcgacat caaggccacc     840
```

```
gctcagaccg acaacgtgca ccgtccgttc tacccgatgc tgatcttccg caccccgaag    900
ggctggacct gcccgaagta catcgacggc aagaagaccg agggctcctg gcgttcccac    960
caggtgccgc tggcttccgc ccgcgacacc gaggcccact tcgaggttct caagaactgg   1020
ctcgagtcct acaagccgga agagctgttc gacgccaacg tgctgtcaa ggacgacgtc    1080
cttgccttca tgccgaaggg cgagctgcgt atcggtgcca acccgaacgc caacggtggt   1140
gtgatccgca acgacctgaa gctgccgaac ctcgaggact acgaggtcaa ggaagtggct   1200
gagtacggcc acggctgggg ccagctcgag gccacccgta ccctgggtgc ctacactcgc   1260
gacatcatca gaacaacccc gcgcgacttc cgcatcttcg accggatga accgcttcc    1320
aaccgtctgc aggcttccta cgaagtcacc aacaagcagt gggatgccgg ctacatctcc   1380
gacgaggtcg acgagcacat gcacgtctcc ggccaggtcg ttgagcagct gtccgagcac   1440
cagatggaag gcttcctcga ggcttacctg ctgaccggtc gtcacggcat ctggagctcc   1500
tacgagtcct tcgtccacgt gatcgactcc atgctgaacc agcacgccaa gtggcttgag   1560
gctaccgtcc gcgagattcc gtggcgcaag ccgattgcct ccatgaacct gctggtctcc   1620
tcccacgttt ggcgtcagga ccacaacggc ttctcccacc aggatccggg tgtcacctcc   1680
gtcctgctga acaagtgctt ccacaacgac cacgtcatcg gcatctactt cgccaccgat   1740
gcgaacatgc tgctggccat cgccgagaag tgctacaagt ccaccaacaa gatcaacgcc   1800
atcatcgctg gtaagcagcc tgctgccacc tggctgaccc tggacgaggc tcgtgccgag   1860
ctcgagaagg gtgccgccgc ttgggattgg gcttccaccg ccaagaacaa cgatgaggcc   1920
gaggtcgtgc ttgccgccgc cggcgatgtc ccgactcagg agatcatggc tgcttccgac   1980
aagctgaagg aactgggcat caagttcaag gttgtgaacg ttgccgacct gctctccctg   2040
cagtccgcca aggagaacga cgaggctctg accgacgagg agttcgccga catcttcacc   2100
gccgacaagc cggtgctgtt cgcgtaccac tcctacgctc acgacgtgcg tggcctgatc   2160
tacgaccgtc cgaaccacga caacttcaac gtccacggct acgaggagga gggctccacc   2220
accacccccgt acgacatggt tcgtgtcaac cgcatcgacc gctacgagct gaccgctgag   2280
gctctgcgca tgatcgacgc cgacaagtac gccgacaaga tcgacgagct cgagaagttc   2340
cgtgatgagg ccttccagtt cgccgtcgac aacggctacg atcacccgga ctacaccgac   2400
tgggtgtact ccggcgtgaa caccgacaag aagggtgccg tcaccgctac cgccgctacc   2460
gctggcgaca acgagtga                                                 2478
```

<210> SEQ ID NO 14
<211> LENGTH: 825
<212> TYPE: PRT
<213> ORGANISM: Bifidobacterium longum

<400> SEQUENCE: 14

```
Met Thr Ser Pro Val Ile Gly Thr Pro Trp Lys Lys Leu Asn Ala Pro
1               5                   10                  15

Val Ser Glu Glu Ala Leu Glu Gly Val Asp Lys Tyr Trp Arg Val Ala
            20                  25                  30

Asn Tyr Leu Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
    50                  55                  60

Trp Gly Thr Thr Pro Gly Leu Asn Phe Leu Ile Gly His Ile Asn Arg
65                  70                  75                  80
```

-continued

Phe Ile Ala Asp His Gly Gln Asn Thr Val Ile Met Gly Pro Gly
                85                  90                  95

His Gly Gly Pro Ala Gly Thr Ser Gln Ser Tyr Leu Asp Gly Thr Tyr
            100                 105                 110

Thr Glu Thr Phe Pro Lys Ile Thr Lys Asp Glu Ala Gly Leu Gln Lys
        115                 120                 125

Phe Phe Arg Gln Phe Ser Tyr Pro Gly Gly Ile Pro Ser His Phe Ala
130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
                165                 170                 175

Pro Ala Ile Val Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ser Arg Ile Ser Asp Glu Glu Leu His Glu Phe Phe His Gly Met
225                 230                 235                 240

Gly Tyr Glu Pro Tyr Glu Phe Val Ala Gly Phe Asp Asp Glu Asp His
                245                 250                 255

Met Ser Ile His Arg Arg Phe Ala Glu Leu Trp Glu Thr Ile Trp Asp
            260                 265                 270

Glu Ile Cys Asp Ile Lys Ala Thr Ala Gln Thr Asp Asn Val His Arg
        275                 280                 285

Pro Phe Tyr Pro Met Leu Ile Phe Arg Thr Pro Lys Gly Trp Thr Cys
290                 295                 300

Pro Lys Tyr Ile Asp Gly Lys Lys Thr Glu Gly Ser Trp Arg Ser His
305                 310                 315                 320

Gln Val Pro Leu Ala Ser Ala Arg Asp Thr Glu Ala His Phe Glu Val
                325                 330                 335

Leu Lys Asn Trp Leu Glu Ser Tyr Lys Pro Glu Glu Leu Phe Asp Ala
            340                 345                 350

Asn Gly Ala Val Lys Asp Val Leu Ala Phe Met Pro Lys Gly Glu
        355                 360                 365

Leu Arg Ile Gly Ala Asn Pro Asn Ala Asn Gly Gly Val Ile Arg Asn
    370                 375                 380

Asp Leu Lys Leu Pro Asn Leu Glu Asp Tyr Glu Val Lys Glu Val Ala
385                 390                 395                 400

Glu Tyr Gly His Gly Trp Gly Gln Leu Glu Ala Thr Arg Thr Leu Gly
                405                 410                 415

Ala Tyr Thr Arg Asp Ile Ile Lys Asn Asn Pro Arg Asp Phe Arg Ile
            420                 425                 430

Phe Gly Pro Asp Glu Thr Ala Ser Asn Arg Leu Gln Ala Ser Tyr Glu
        435                 440                 445

Val Thr Asn Lys Gln Trp Asp Ala Gly Tyr Ile Ser Asp Glu Val Asp
    450                 455                 460

Glu His Met His Val Ser Gly Gln Val Val Glu Gln Leu Ser Glu His
465                 470                 475                 480

Gln Met Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu

-continued

```
                500             505             510
Asn Gln His Ala Lys Trp Leu Glu Ala Thr Val Arg Glu Ile Pro Trp
                515                 520                 525
Arg Lys Pro Ile Ala Ser Met Asn Leu Leu Val Ser Ser His Val Trp
            530                 535                 540
Arg Gln Asp His Asn Gly Phe Ser His Gln Asp Pro Gly Val Thr Ser
545                 550                 555                 560
Val Leu Leu Asn Lys Cys Phe His Asn Asp His Val Ile Gly Ile Tyr
                565                 570                 575
Phe Ala Thr Asp Ala Asn Met Leu Leu Ala Ile Ala Glu Lys Cys Tyr
                580                 585                 590
Lys Ser Thr Asn Lys Ile Asn Ala Ile Ile Ala Gly Lys Gln Pro Ala
                595                 600                 605
Ala Thr Trp Leu Thr Leu Asp Glu Ala Arg Ala Glu Leu Glu Lys Gly
            610                 615                 620
Ala Ala Ala Trp Asp Trp Ala Ser Thr Ala Lys Asn Asn Asp Glu Ala
625                 630                 635                 640
Glu Val Val Leu Ala Ala Gly Asp Val Pro Thr Gln Glu Ile Met
                645                 650                 655
Ala Ala Ser Asp Lys Leu Lys Glu Leu Gly Ile Lys Phe Lys Val Val
                660                 665                 670
Asn Val Ala Asp Leu Leu Ser Leu Gln Ser Ala Lys Glu Asn Asp Glu
                675                 680                 685
Ala Leu Thr Asp Glu Glu Phe Ala Asp Ile Phe Thr Ala Asp Lys Pro
            690                 695                 700
Val Leu Phe Ala Tyr His Ser Tyr Ala His Asp Val Arg Gly Leu Ile
705                 710                 715                 720
Tyr Asp Arg Pro Asn His Asp Asn Phe Asn Val His Gly Tyr Glu Glu
                725                 730                 735
Glu Gly Ser Thr Thr Thr Pro Tyr Asp Met Val Arg Val Asn Arg Ile
                740                 745                 750
Asp Arg Tyr Glu Leu Thr Ala Glu Ala Leu Arg Met Ile Asp Ala Asp
                755                 760                 765
Lys Tyr Ala Asp Lys Ile Asp Glu Leu Glu Lys Phe Arg Asp Glu Ala
                770                 775                 780
Phe Gln Phe Ala Val Asp Asn Gly Tyr Asp His Pro Asp Tyr Thr Asp
785                 790                 795                 800
Trp Val Tyr Ser Gly Val Asn Thr Asp Lys Lys Gly Ala Val Thr Ala
                805                 810                 815
Thr Ala Ala Thr Ala Gly Asp Asn Glu
                820                 825
```

<210> SEQ ID NO 15
<211> LENGTH: 1341
<212> TYPE: DNA
<213> ORGANISM: Corynebacterium glutamicum

<400> SEQUENCE: 15

| | | | | | |
|---|---|---|---|---|---|
| atggattcaa | acacagaatc | ttcaagtgtt | gaggtcaaaa | acgaacacat | taaagttcaa | 60 |
| aagccgccga | agaaggaccg | cactcactgg | ctctacattg | cggtcattat | cgcattgatt | 120 |
| ggcggtatta | ccctaggcct | gatttcaccg | gagttgggca | agaattcaa | gattttgggc | 180 |
| accatgtttg | tgtccttgat | caagatgatt | atcgctccag | ttattttctg | caccatcgtc | 240 |
| atcggaatcg | gttcagtcaa | ggcagcggca | acagtcggac | gcgctggtgg | catcgccctt | 300 |

```
gcgtacttca tcacgatgtc cacattcgca ctcgcagttg gcctgctagt cggtaacttc    360
atccagccag gtagcggact gaacatctca gttgatgaag aatcttcatt cgcatccaca    420
gagagcagcc ctgaaggact cttgggattc atccactcga tcatccctga aacgttcttc    480
tctgcattta ctgatggttc ggtgctgcag gtactgttca tcgccatcct cgtgggcttt    540
gcagctcagt cgatgggtga aaagggacag cccatccttg atttcgtatc ccatctgcag    600
aagctcatct tcaagatttt gaactggatt ctgtggctcg ccccagtcgg tgcattcggt    660
gcaatggccg gcgtcgttgg cgaaacaggc tttgatgccg ttgttcagct cggtattttg    720
atcctcgcct tttacgtcac ctgcgtgatc ttcatctttg gcgtgctggg cgccgtactg    780
aaggtgttca ccggcgtgaa tatcttcaag ctggtcaagt accttgccaa ggaattcctg    840
ctgatctttg ctacctcatc ctctgaatct gccttgccaa acctcatgcg caagatggaa    900
cacatcggtg tggctaaacc aaccgtcgga atcgtggtcc caaccggcta ttccttcaac    960
ttggacggca ccgcaattta cctcaccatg gcatctatct tcattgccga cgcgatgaat   1020
atgccgatga gcctcggcga gcaggtcggt ctgcttgtct tcatgatcat cgcatccaag   1080
ggcgctgctg gtgtctcggg tgccggtatt gcaacgttgg ctgccggatt gtcttcacac   1140
cgcccagaac ttctgcacgg cgttgacgtg attgtgggca tcgataaatt catgtctgaa   1200
gcccgcgcac taaccaactt cgccggaaac tccgtggcaa cactgctggt cggcaagtgg   1260
actggcaccg tggacatgaa ccaagtccat gacgttttga atggaaaatc tccatttgtg   1320
gagttagaag aagaccacta g                                              1341
```

```
<210> SEQ ID NO 16
<211> LENGTH: 446
<212> TYPE: PRT
<213> ORGANISM: Corynebacterium glutamicum

<400> SEQUENCE: 16

Met Asp Ser Asn Thr Glu Ser Ser Val Glu Val Lys Asn Glu His
1               5                   10                  15

Ile Lys Val Gln Lys Pro Pro Lys Lys Asp Arg Thr His Trp Leu Tyr
            20                  25                  30

Ile Ala Val Ile Ile Ala Leu Ile Gly Gly Ile Thr Leu Gly Leu Ile
        35                  40                  45

Ser Pro Glu Leu Gly Lys Glu Phe Lys Ile Leu Gly Thr Met Phe Val
    50                  55                  60

Ser Leu Ile Lys Met Ile Ile Ala Pro Val Ile Phe Cys Thr Ile Val
65                  70                  75                  80

Ile Gly Ile Gly Ser Val Lys Ala Ala Ala Thr Val Gly Arg Ala Gly
                85                  90                  95

Gly Ile Ala Leu Ala Tyr Phe Ile Thr Met Ser Thr Phe Ala Leu Ala
            100                 105                 110

Val Gly Leu Leu Val Gly Asn Phe Ile Gln Pro Gly Ser Gly Leu Asn
        115                 120                 125

Ile Ser Val Asp Glu Glu Ser Ser Phe Ala Ser Thr Glu Ser Ser Pro
    130                 135                 140

Glu Gly Leu Leu Gly Phe Ile His Ser Ile Ile Pro Glu Thr Phe Phe
145                 150                 155                 160

Ser Ala Phe Thr Asp Gly Ser Val Leu Gln Val Leu Phe Ile Ala Ile
                165                 170                 175

Leu Val Gly Phe Ala Ala Gln Ser Met Gly Glu Lys Gly Gln Pro Ile
```

```
                    180                185                190
Leu Asp Phe Val Ser His Leu Gln Lys Leu Ile Phe Lys Ile Leu Asn
            195                200                205

Trp Ile Leu Trp Leu Ala Pro Val Gly Ala Phe Gly Ala Met Ala Gly
        210                215                220

Val Val Gly Glu Thr Gly Phe Asp Ala Val Val Gln Leu Gly Ile Leu
225                230                235                240

Ile Leu Ala Phe Tyr Val Thr Cys Val Ile Phe Ile Phe Gly Val Leu
                245                250                255

Gly Ala Val Leu Lys Val Phe Thr Gly Val Asn Ile Phe Lys Leu Val
                260                265                270

Lys Tyr Leu Ala Lys Glu Phe Leu Leu Ile Phe Ala Thr Ser Ser Ser
            275                280                285

Glu Ser Ala Leu Pro Asn Leu Met Arg Lys Met Glu His Ile Gly Val
        290                295                300

Ala Lys Pro Thr Val Gly Ile Val Val Pro Thr Gly Tyr Ser Phe Asn
305                310                315                320

Leu Asp Gly Thr Ala Ile Tyr Leu Thr Met Ala Ser Ile Phe Ile Ala
                325                330                335

Asp Ala Met Asn Met Pro Met Ser Leu Gly Glu Gln Val Gly Leu Leu
                340                345                350

Val Phe Met Ile Ile Ala Ser Lys Gly Ala Ala Gly Val Ser Gly Ala
            355                360                365

Gly Ile Ala Thr Leu Ala Ala Gly Leu Ser Ser His Arg Pro Glu Leu
        370                375                380

Leu His Gly Val Asp Val Ile Val Gly Ile Asp Lys Phe Met Ser Glu
385                390                395                400

Ala Arg Ala Leu Thr Asn Phe Ala Gly Asn Ser Val Ala Thr Leu Leu
                405                410                415

Val Gly Lys Trp Thr Gly Thr Val Asp Met Asn Gln Val His Asp Val
                420                425                430

Leu Asn Gly Lys Ser Pro Phe Val Glu Leu Glu Glu Asp His
            435                440                445

<210> SEQ ID NO 17
<211> LENGTH: 1287
<212> TYPE: DNA
<213> ORGANISM: Escherichia coli

<400> SEQUENCE: 17
atgaaaacct ctctgtttaa aagcctttac tttcaggtcc tgacagcgat agccattggt      60
attctccttg ccatttctca tcctgaaata ggcgagcaaa tgaaaccgct tggcgacggc     120
ttcgttaagc tcattaagat gatcatcgct cctgtcatct tttgtaccgt cgtaacgggc     180
attgcgggca tggaaagcat gaaggcggtc ggtcgtaccg cgcagtcgc actgctttac     240 tttgaaattg tcagtaccat cgcgctgatt attggtctta tcatcgttaa cgtcgtgcag     300
cctggtgccg gaatgaacgt cgatccggca acgcttgatg cgaaagcggt agcggtttac     360
gccgatcagg cgaaagacca gggcattgtc gccttcatta tggatgtcat cccggcgagc     420
gtcattggcg catttgccag cggtaacatt ctgcaggtgc tgctgtttgc cgtactgttt     480
ggttttgcgc tccaccgtct gggcagcaaa ggccaactga ttttaacgt catcgaaagt     540 ttctcgcagg tcatccttcg catcatcaat atgatcatgc gtctggcacc tattggtgcg     600
ttcggggcaa tggcgtttac catcggtaaa tacggcgtcg gcacactggt gcaactgggg     660
```

-continued

```
cagctgatta tctgtttcta cattacctgt atcctgtttg tggtgctggt attgggttca    720
atcgctaaag cgactggttt cagtatcttc aaatttatcc gctacatccg tgaagaactg    780
ctgattgtac tggggacttc atcttccgag tcggcgctgc cgcgtatgct cgacaagatg    840
gagaaactcg gctgccgtaa atcggtggtg gggctggtca tcccgacagg ctactcgttt    900
aaccttgatg gcacatcgat atacctgaca atggcggcgg tgtttatcgc ccaggccact    960
aacagtcaga tggatatcgt ccaccaaatc acgctgttaa tcgtgttgct gctttcttct   1020 aaagggcgg caggggtaac gggtagtggc tttatcgtgc tggcggcgac gctctctgcg   1080
gtgggccatt tgccggtagc gggtctggcg ctgatcctcg gtatcgaccg ctttatgtca   1140
gaagctcgtg cgctgactaa cctggtcggt aacggcgtag cgaccattgt cgttgctaag   1200
tgggtgaaag aactggacca caaaaaactg gacgatgtgc tgaataatcg tgcgccggat   1260
ggcaaaacgc acgaattatc ctcttaa                                        1287
```

<210> SEQ ID NO 18
<211> LENGTH: 428
<212> TYPE: PRT
<213> ORGANISM: Escherichia coli

<400> SEQUENCE: 18

```
Met Lys Thr Ser Leu Phe Lys Ser Leu Tyr Phe Gln Val Leu Thr Ala
1               5                   10                  15

Ile Ala Ile Gly Ile Leu Leu Gly His Phe Tyr Pro Glu Ile Gly Glu
            20                  25                  30

Gln Met Lys Pro Leu Gly Asp Gly Phe Val Lys Leu Ile Lys Met Ile
        35                  40                  45

Ile Ala Pro Val Ile Phe Cys Thr Val Val Thr Gly Ile Ala Gly Met
    50                  55                  60

Glu Ser Met Lys Ala Val Gly Arg Thr Gly Ala Val Ala Leu Leu Tyr
65                  70                  75                  80

Phe Glu Ile Val Ser Thr Ile Ala Leu Ile Ile Gly Leu Ile Ile Val
                85                  90                  95

Asn Val Val Gln Pro Gly Ala Gly Met Asn Val Asp Pro Ala Thr Leu
            100                 105                 110

Asp Ala Lys Ala Val Ala Val Tyr Ala Asp Gln Ala Lys Asp Gln Gly
        115                 120                 125

Ile Val Ala Phe Ile Met Asp Val Ile Pro Ala Ser Val Ile Gly Ala
    130                 135                 140

Phe Ala Ser Gly Asn Ile Leu Gln Val Leu Leu Phe Ala Val Leu Phe
145                 150                 155                 160

Gly Phe Ala Leu His Arg Leu Gly Ser Lys Gly Gln Leu Ile Phe Asn
                165                 170                 175

Val Ile Glu Ser Phe Ser Gln Val Ile Phe Gly Ile Ile Asn Met Ile
            180                 185                 190

Met Arg Leu Ala Pro Ile Gly Ala Phe Gly Ala Met Ala Phe Thr Ile
        195                 200                 205

Gly Lys Tyr Gly Val Gly Thr Leu Val Gln Leu Gly Gln Leu Ile Ile
    210                 215                 220

Cys Phe Tyr Ile Thr Cys Ile Leu Phe Val Val Leu Val Leu Gly Ser
225                 230                 235                 240

Ile Ala Lys Ala Thr Gly Phe Ser Ile Phe Lys Phe Ile Arg Tyr Ile
                245                 250                 255
```

```
Arg Glu Glu Leu Leu Ile Val Leu Gly Thr Ser Ser Glu Ser Ala
            260                 265                 270

Leu Pro Arg Met Leu Asp Lys Met Glu Lys Leu Gly Cys Arg Lys Ser
        275                 280                 285

Val Val Gly Leu Val Ile Pro Thr Gly Tyr Ser Phe Asn Leu Asp Gly
    290                 295                 300

Thr Ser Ile Tyr Leu Thr Met Ala Ala Val Phe Ile Ala Gln Ala Thr
305                 310                 315                 320

Asn Ser Gln Met Asp Ile Val His Gln Ile Thr Leu Leu Ile Val Leu
                325                 330                 335

Leu Leu Ser Ser Lys Gly Ala Ala Gly Val Thr Gly Ser Gly Phe Ile
            340                 345                 350

Val Leu Ala Ala Thr Leu Ser Ala Val Gly His Leu Pro Val Ala Gly
        355                 360                 365

Leu Ala Leu Ile Leu Gly Ile Asp Arg Phe Met Ser Glu Ala Arg Ala
    370                 375                 380

Leu Thr Asn Leu Val Gly Asn Gly Val Ala Thr Ile Val Val Ala Lys
385                 390                 395                 400

Trp Val Lys Glu Leu Asp His Lys Lys Leu Asp Asp Val Leu Asn Asn
                405                 410                 415

Arg Ala Pro Asp Gly Lys Thr His Glu Leu Ser Ser
            420                 425
```

<210> SEQ ID NO 19
<211> LENGTH: 1302
<212> TYPE: DNA
<213> ORGANISM: Escherichia coli

<400> SEQUENCE: 19

```
atgctagttg tagaactcat catagttttg ctggcgatct tcttgggcgc cagattgggg    60
ggaataggta ttggttttgc aggcggattg ggggtgctgg ttcttgccgc tattggcgtt   120
aaacccggta acatcccgtt cgatgtcatc tccattatca tggcggttat cgccgctatt   180
tctgccatgc aggttgctgg cggtctggac tatctggttc atcagacaga aaagctgctg   240
cgccgtaacc cgaaatacat cacgatcctc gcaccgatcg tgacctattt cctgactatc   300
tttgctggta ctggcaacat ctctctggcg acactgccag ttatcgctga agttgcgaag   360
gaacaaggcg ttaaaccttg ccgtccgctg tctactgcag tggtatccgc gcagattgcg   420
atcaccgcat cgccaatctc agcggcagtg gtttacatgt cttccgtgat ggaaggtcat   480
ggcatcagct acctccatct gctctccgtg gtcatcccgt ccaccctgct ggcggttctg   540
gtgatgtcct tcctggtcac tatgctgttc aactccaaac tctctgacga tccgatttat   600
cgcaagcgtc tggaagaggg cctggttgaa ctgcgcggtg aaaagcagat tgaaatcaaa   660
tccggtgcaa aaacgtccgt ctggctgttc ctgctgggcg tagttggcgt ggttatctat   720
gcaatcatca cagcccaag catgggtctg gttgaaaaac cgctgatgaa caccaccaac   780
gcaatcctga tcatcatgct cagcgttgca actctgacca ccgttatctg taaagtcgat   840
accgacaaca tcctcaactc cagcaccttc aaagcaggta tgagcgcctg tatttgtatc   900
ctgggtgttg cgtggctggg cgatactttc gtttccaaca acatcgactg gatcaaagat   960
accgctggtg aagtgattca gggtcatccg tggctgctgg ccgtcatctt cttctttgct  1020
tctgctctgc tgtactctca ggctgcaacc gcaaaagcac tgatgccgat ggctctggca  1080
ctgaacgttt caccgctgac cgctgttgct ctttcgctg cggtgtctgg tctgttcatt  1140
```

```
ctgccgacct acccgacgct ggttgctgcg gtacagatgg atgacacggg tactacccgt   1200
atcggtaaat tcgtcttcaa ccatccgttc ttcatcccgg gtactctggg tgttgccctg   1260
gccgtttgct tcggcttcgt gctgggtagc ttcatgctgt aa                      1302
```

<210> SEQ ID NO 20
<211> LENGTH: 433
<212> TYPE: PRT
<213> ORGANISM: Escherichia coli

<400> SEQUENCE: 20

```
Met Leu Val Val Glu Leu Ile Ile Val Leu Leu Ala Ile Phe Leu Gly
1               5                   10                  15

Ala Arg Leu Gly Gly Ile Gly Ile Gly Phe Ala Gly Gly Leu Gly Val
            20                  25                  30

Leu Val Leu Ala Ala Ile Gly Val Lys Pro Gly Asn Ile Pro Phe Asp
        35                  40                  45

Val Ile Ser Ile Ile Met Ala Val Ile Ala Ile Ser Ala Met Gln
 50                  55                  60

Val Ala Gly Gly Leu Asp Tyr Leu Val His Gln Thr Glu Lys Leu Leu
65                  70                  75                  80

Arg Arg Asn Pro Lys Tyr Ile Thr Ile Leu Ala Pro Ile Val Thr Tyr
                85                  90                  95

Phe Leu Thr Ile Phe Ala Gly Thr Gly Asn Ile Ser Leu Ala Thr Leu
            100                 105                 110

Pro Val Ile Ala Glu Val Ala Lys Glu Gln Gly Val Lys Pro Cys Arg
        115                 120                 125

Pro Leu Ser Thr Ala Val Val Ser Ala Gln Ile Ala Ile Thr Ala Ser
    130                 135                 140

Pro Ile Ser Ala Ala Val Val Tyr Met Ser Ser Val Met Glu Gly His
145                 150                 155                 160

Gly Ile Ser Tyr Leu His Leu Leu Ser Val Val Ile Pro Ser Thr Leu
                165                 170                 175

Leu Ala Val Leu Val Met Ser Phe Leu Val Thr Met Leu Phe Asn Ser
            180                 185                 190

Lys Leu Ser Asp Asp Pro Ile Tyr Arg Lys Arg Leu Glu Glu Gly Leu
        195                 200                 205

Val Glu Leu Arg Gly Glu Lys Gln Ile Glu Ile Lys Ser Gly Ala Lys
    210                 215                 220

Thr Ser Val Trp Leu Phe Leu Leu Gly Val Val Gly Val Val Ile Tyr
225                 230                 235                 240

Ala Ile Ile Asn Ser Pro Ser Met Gly Leu Val Glu Lys Pro Leu Met
                245                 250                 255

Asn Thr Thr Asn Ala Ile Leu Ile Ile Met Leu Ser Val Ala Thr Leu
            260                 265                 270

Thr Thr Val Ile Cys Lys Val Asp Thr Asp Asn Ile Leu Asn Ser Ser
        275                 280                 285

Thr Phe Lys Ala Gly Met Ser Ala Cys Ile Cys Ile Leu Gly Val Ala
    290                 295                 300

Trp Leu Gly Asp Thr Phe Val Ser Asn Ile Asp Trp Ile Lys Asp
305                 310                 315                 320

Thr Ala Gly Glu Val Ile Gln Gly His Pro Trp Leu Leu Ala Val Ile
                325                 330                 335

Phe Phe Phe Ala Ser Ala Leu Leu Tyr Ser Gln Ala Ala Thr Ala Lys
            340                 345                 350
```

```
Ala Leu Met Pro Met Ala Leu Ala Leu Asn Val Ser Pro Leu Thr Ala
        355                 360                 365

Val Ala Ser Phe Ala Ala Val Ser Gly Leu Phe Ile Leu Pro Thr Tyr
    370                 375                 380

Pro Thr Leu Val Ala Ala Val Gln Met Asp Asp Thr Gly Thr Thr Arg
385                 390                 395                 400

Ile Gly Lys Phe Val Phe Asn His Pro Phe Phe Ile Pro Gly Thr Leu
                405                 410                 415

Gly Val Ala Leu Ala Val Cys Phe Gly Phe Val Leu Gly Ser Phe Met
                420                 425                 430

Leu
```

```
<210> SEQ ID NO 21
<211> LENGTH: 1341
<212> TYPE: DNA
<213> ORGANISM: Escherichia coli

<400> SEQUENCE: 21
atgttattta ctatccaact tatcataata ctgatatgtc tgttttatgg tgccagaaag      60
ggtggtatcg cgctgggttt attaggcggt atcggtctgg tcattctggt cttcgtcttc     120
caccttcagc caggtaaacc accagttgat gtcatgctgg ttatcattgc ggtggtggcg     180
gcatcggcga ccttgcaagc ttcgggcggt cttgatgtca tgctgcaaat tgccgagaag     240
ctgctgcgcc gcaacccgaa atatgtctca attgtcgcgc cgtttgtgac ctgtacactg     300
accattcttt gcggtacggg tcatgtggtt tacaccattc tgccgatcat ctacgacgtc     360
gccattaaga caacatccg tccggaacgt ccgatggcgg caagttctat cggtgcacag     420
atggggatta cgccagtcc ggtgtcggtt gcggtcgtgt ctctggttgc gatgctgggt     480
aatgtcacct ttgatggtcg ccatcttgag ttcctcgatc tgctggcaat caccattcca     540
tcgacgttaa tcgtatcct ggcgatcggt atcttcagct ggttccgcgg taaagatctg     600
gataaagacg aagagttcca gaaattcatc tccgtaccgg aaaaccgtga gtatgtttac     660
ggtgataccg cgacgctgct ggataaaaaa ctgccgaaaa gcaactggct ggcaatgtgg     720
attttcctcg gggcaatcgc tgtagtcgcc cttcttggtg ctgattcgga cctgcgtcca     780
tccttcggcg gcaaaccgct gtcgatggta ctggttattc agatgtttat gctgctgacc     840 gggggcgctga ttattatcct gaccaaaacc aatcccgcgt ctatctcaaa aaacgaagtc     900
ttccgttccg gtatgatcgc catcgtggcg gtgtacggta tcgcatggat ggcagaaacc     960
atgttcggtg cgcatatgtc tgaaattcag ggcgtactgg gtgaaatggt gaaagagtat    1020
ccgtgggcct atgccattgt tctgctgctg gtttccaagt ttgtaaactc tcaggctgcg    1080
gcgctggcgg cgattgttcc ggtcgcgctg gcgatcggcg ttgatccggc atacatcgtg    1140
gcttcagcac cggcttgcta cggttattac atcctgccga cttatccgag cgatctggca    1200
gcgattcagt tgaccgttc cggcaccacc cacatcggtc gcttcgtcat caaccacagc    1260
tttattctgc cggggttgat tggtgtgagc gtatcgtgcg tcttcggctg gatcttcgcc    1320
gcgatgtacg ggttcttata a                                              1341
```

```
<210> SEQ ID NO 22
<211> LENGTH: 446
<212> TYPE: PRT
<213> ORGANISM: Escherichia coli

<400> SEQUENCE: 22
```

-continued

```
Met Leu Phe Thr Ile Gln Leu Ile Ile Leu Ile Cys Leu Phe Tyr
 1               5                  10                  15

Gly Ala Arg Lys Gly Gly Ile Ala Leu Gly Leu Leu Gly Ile Gly
                20                  25                  30

Leu Val Ile Leu Val Phe Val Phe His Leu Gln Pro Gly Lys Pro
             35                  40                  45

Val Asp Val Met Leu Val Ile Ile Ala Val Ala Ala Ser Ala Thr
 50                  55                  60

Leu Gln Ala Ser Gly Gly Leu Asp Val Met Leu Gln Ile Ala Glu Lys
 65                  70                  75                  80

Leu Leu Arg Arg Asn Pro Lys Tyr Val Ser Ile Val Ala Pro Phe Val
                85                  90                  95

Thr Cys Thr Leu Thr Ile Leu Cys Gly Thr His Val Val Tyr Thr
                100                 105                 110

Ile Leu Pro Ile Ile Tyr Asp Val Ala Ile Lys Asn Asn Ile Arg Pro
             115                 120                 125

Glu Arg Pro Met Ala Ala Ser Ser Ile Gly Ala Gln Met Gly Ile Ile
     130                 135                 140

Ala Ser Pro Val Ser Val Ala Val Val Ser Leu Val Ala Met Leu Gly
145                 150                 155                 160

Asn Val Thr Phe Asp Gly Arg His Leu Glu Phe Leu Asp Leu Leu Ala
                165                 170                 175

Ile Thr Ile Pro Ser Thr Leu Ile Gly Ile Leu Ala Ile Gly Ile Phe
                180                 185                 190

Ser Trp Phe Arg Gly Lys Asp Leu Asp Lys Asp Glu Gly Phe Gln Lys
                195                 200                 205

Phe Ile Ser Val Pro Glu Asn Arg Glu Tyr Val Tyr Gly Asp Thr Ala
     210                 215                 220

Thr Leu Leu Asp Lys Lys Leu Pro Lys Ser Asn Trp Leu Ala Met Trp
225                 230                 235                 240

Ile Phe Leu Gly Ala Ile Ala Val Val Ala Leu Leu Gly Ala Asp Ser
                245                 250                 255

Asp Leu Arg Pro Ser Phe Gly Gly Lys Pro Leu Ser Met Val Leu Val
     260                 265                 270

Ile Gln Met Phe Met Leu Leu Thr Gly Ala Leu Ile Ile Ile Leu Thr
     275                 280                 285

Lys Thr Asn Pro Ala Ser Ile Ser Lys Asn Glu Val Phe Arg Ser Gly
     290                 295                 300

Met Ile Ala Ile Val Ala Val Tyr Gly Ile Ala Trp Met Ala Glu Thr
305                 310                 315                 320

Met Phe Gly Ala His Met Ser Glu Ile Gln Gly Val Leu Gly Glu Met
                325                 330                 335

Val Lys Glu Tyr Pro Trp Ala Tyr Ala Ile Val Leu Leu Val Ser
     340                 345                 350

Lys Phe Val Asn Ser Gln Ala Ala Leu Ala Ala Ile Val Pro Val
     355                 360                 365

Ala Leu Ala Ile Gly Val Asp Pro Ala Tyr Ile Val Ala Ser Ala Pro
370                 375                 380

Ala Cys Tyr Gly Tyr Tyr Ile Leu Pro Thr Tyr Pro Ser Asp Leu Ala
385                 390                 395                 400

Ala Ile Gln Phe Asp Arg Ser Gly Thr Thr His Ile Gly Arg Phe Val
                405                 410                 415
```

-continued

```
Ile Asn His Ser Phe Ile Leu Pro Gly Leu Ile Gly Val Ser Val Ser
            420                 425                 430

Cys Val Phe Gly Trp Ile Phe Ala Ala Met Tyr Gly Phe Leu
            435                 440                 445
```

METHOD FOR PRODUCING L-AMINO ACID

This application claims priority therethrough under 35 U.S.C. § 119 to Japanese Patent Application No. 2016-195818, filed Oct. 23, 2016, the entirety of which is incorporated by reference herein. Also, the Sequence Listing filed electronically herewith is hereby incorporated by reference (File name: 2017-09-27T_US-566 _Seq_List; File size: 51 KB; Date recorded: Sep. 27, 2017).

BACKGROUND OF THE INVENTION

Field of the Invention

The present invention relates to a method for producing an L-amino acid such as L-glutamic acid by fermentation using a bacterium. L-Amino acids are industrially useful as raw materials of seasonings and so forth.

Brief Description of the Related Art

L-Amino acids are industrially produced by, for example, fermentation using microorganisms such as bacteria having an L-amino acid-producing ability (Akashi, K. et al., Amino Acid Fermentation. Japan Scientific Societies Press, p. 195 to 215, 1986). For example, bacterial strains isolated from nature, or mutant strains thereof have been used. Also, the ability of microorganisms to produce L-amino acids can be improved by using recombinant DNA techniques. For example, the ability of bacteria to produce L-glutamic acid has been enhanced by increasing the phosphoketolase activity (WO2006/016705) or utilizing a mutant yggB gene (WO2006/070944).

Various C4-dicarboxylic acid-uptake carriers have been found in bacteria. Bacteria can uptake and metabolize C4-dicarboxylic acids via C4-dicarboxylic acid-uptake carriers. For example, it is known that the proteins encoded by the dctA gene, dcuA gene, and dcuB gene all have uptake ability for a C4-dicarboxylic acid such as aspartic acid (Karinou E. et al., The *Escherichia coli* SLC26 homologue YchM (DauA) is a C4-dicarboxylic acid transporter. Mol Microbiol. 2013 February; 87(3):623-40 and Janausch I G. et al., C4-dicarboxylate carriers and sensors in bacteria. Biochim Biophys Acta. 2002 January 17; 1553(1-2):39-56). It is also known that a protein encoded by dctA gene also has uptake ability for L-glutamic acid (Youn et al., Characterization of the Dicarboxylate Transporter DctA in *Corynebacterium glutamicum*. Journal Of Bacteriology. 2009 September 5480-5488).

In addition, a method for producing an L-amino acid using a coryneform bacterium having an increased expression of dctA gene has been reported (US2002-0106759), and includes an example in which L-lysine was produced with this bacterium. While L-amino acids other than L-lysine, such as L-glutamic acid, are also exemplified, it has not been reported whether other L-amino acids, such as L-glutamic acid, can be produced using this bacterium.

In addition, it is known that a protein encoded by the yggB gene has excretion ability for L-glutamic acid (WO2006/070944 and Nakamura et al., Mutations of the *Corynebacterium glutamicum* NCgl1221 Gene, Encoding a Mechanosensitive Channel Homolog, Induce 1-Glutamic Acid Production. Applied And Environmental Microbiology. 2007 July 4491-4498).

SUMMARY OF THE INVENTION

It is an aspect of the present invention to develop a novel technique for improving an L-amino acid-producing ability of a bacterium, and thereby provide a method for efficiently producing an L-amino acid.

It has been found that the ability of a bacterium to produce an L-amino acid can be improved by modifying the bacterium to increase the expression of the dctA gene, dcuA gene, or dcuB gene, each of which encode a C4-dicarboxylic acid-uptake carrier.

It is an aspect of the present invention to provide a method for producing an L-amino acid, the method comprising the steps of: A) culturing a bacterium having an L-amino acid-producing ability in a medium resulting in accumulation of an L-amino acid in the medium and/or cells of the bacterium; and B) collecting the L-amino acid from the medium and/or the cells, wherein the bacterium has been modified so that activity of a C4-dicarboxylic acid-uptake carrier is increased as compared with a non-modified bacterium, wherein the C4-dicarboxylic acid-uptake carrier is a protein encoded by a gene selected from the group consisting of a dctA gene, a dcuA gene, a dcuB gene, and combinations thereof, and wherein the L-amino acid is an L-amino acid other than L-aspartic acid, provided that the L-amino acid is L-glutamic acid when the C4-dicarboxylic acid-uptake carrier is a protein encoded by a dctA gene.

It is a further aspect of the present invention to provide the method as described above, wherein dctA gene encodes a protein selected from the group consisting of: (a) a protein comprising the amino acid sequence of SEQ ID NO: 16 or 18; (b) a protein comprising the amino acid sequence of SEQ ID NO: 16 or 18, but which includes substitution, deletion, insertion, and/or addition of 1 to 10 amino acid residues, and wherein said protein has L-aspartic acid-uptake activity; (c) a protein comprising an amino acid sequence having an identity of 90% or higher to the amino acid sequence of SEQ ID NO: 16 or 18, and wherein said protein has aspartic acid-uptake activity.

It is a further aspect of the present invention to provide the method as described above, wherein the dcuA gene encodes a protein selected from the group consisting of: (a) a protein comprising the amino acid sequence of SEQ ID NO: 20; (b) a protein comprising the amino acid sequence of SEQ ID NO: 20, but which includes substitution, deletion, insertion, and/or addition of 1 to 10 amino acid residues, and wherein said protein has aspartic acid-uptake activity; (c) a protein comprising an amino acid sequence having an identity of 90% or higher to the amino acid sequence of SEQ ID NO: 20, and wherein said protein has aspartic acid-uptake activity.

It is a further aspect of the present invention to provide the method as described above, wherein the dcuB gene encodes a protein selected from the group consisting of: (a) a protein comprising the amino acid sequence of SEQ ID NO: 22; (b) a protein comprising the amino acid sequence of SEQ ID NO: 22, but which includes substitution, deletion, insertion, and/or addition of 1 to 10 amino acid residues, and wherein said protein has aspartic acid-uptake activity; (c) a protein comprising an amino acid sequence having an identity of 90% or higher to the amino acid sequence of SEQ ID NO: 22, and wherein said protein has aspartic acid-uptake activity.

It is a further aspect of the present invention to provide the method as described above, wherein the activity of the C4-dicarboxylic acid-uptake carrier is increased by increasing expression of a gene encoding the C4-dicarboxylic acid-uptake carrier.

It is a further aspect of the present invention to provide the method as described above, wherein the expression of the gene is increased by increasing the copy number of the gene and/or modifying an expression control sequence of the gene.

It is a further aspect of the present invention to provide the method as described above, wherein the bacterium has further been modified so that activity of phosphoketolase is increased as compared with a non-modified bacterium.

It is a further aspect of the present invention to provide the method as described above, wherein the phosphoketolase is D-xylulose-5-phosphate phosphoketolase, and/or fructose-6-phosphate phosphoketolase.

It is a further aspect of the present invention to provide the method as described above, wherein the activity of the phosphoketolase is increased by increasing expression of a gene encoding the phosphoketolase.

It is a further aspect of the present invention to provide the method as described above, wherein the bacterium is a coryneform bacterium or a bacterium belonging to the family Enterobacteriaceae.

It is a further aspect of the present invention to provide the method as described above, wherein the bacterium is a bacterium belonging to the genus *Corynebacterium*.

It is a further aspect of the present invention to provide the method as described above, wherein the bacterium is *Corynebacterium glutamicum*.

It is a further aspect of the present invention to provide the method as described above, wherein the bacterium is a bacterium belonging to the genus *Pantoea* or *Escherichia*.

It is a further aspect of the present invention to provide the method as described above, wherein the bacterium is *Pantoea ananatis* or *Escherichia coli*.

It is a further aspect of the present invention to provide the method as described above, wherein the L-amino acid is an L-amino acid of the glutamate family and/or an L-amino acid of the aspartate family.

It is a further aspect of the present invention to provide the method as described above, wherein the L-amino acid of the glutamate family is selected from the group consisting of L-glutamic acid, L-glutamine, L-proline, L-arginine, L-citrulline, L-ornithine, and combinations thereof.

It is a further aspect of the present invention to provide the method as described above, wherein the L-amino acid of the glutamate family is L-glutamic acid.

It is a further aspect of the present invention to provide the method as described above, wherein the L-glutamic acid is monoammonium L-glutamate or monosodium L-glutamate.

It is a further aspect of the present invention to provide the method as described above, wherein the L-amino acid of the aspartate family is selected from the group consisting of L-lysine, L-threonine, L-isoleucine, L-methionine, and combinations thereof.

It is a further aspect of the present invention to provide the method as described above, wherein the L-amino acid is an L-amino acid of the glutamate family, and wherein the bacterium has further been modified so that the activity of α-ketoglutarate dehydrogenase and/or succinate dehydrogenase is reduced as compared with a non-modified bacterium.

It is a further aspect of the present invention to provide the method as described above,
wherein the bacterium is a coryneform bacterium, and wherein the bacterium has further been modified so as to harbor a mutant yggB gene.

It is a further aspect of the present invention to provide the method as described above, wherein the mutant yggB gene has a mutation that imparts improved L-glutamic acid-producing ability to the coryneform bacterium.

It is a further aspect of the present invention to provide the method as described above, wherein the mutant yggB gene has a mutation selected from the group consisting of: (1) a mutation in the region coding for the amino acid residues at positions 419 to 533 of a wild-type YggB protein, (2) a mutation in the region coding for a transmembrane region of a wild-type YggB protein, and (3) a combination thereof.

It is a further aspect of the present invention to provide the method as described above, wherein the wild-type YggB protein is selected from the group consisting of: (a) a protein comprising the amino acid sequence of SEQ ID NO: 10; (b) a protein comprising the amino acid sequence of SEQ ID NO: 10, but which includes substitution, deletion, insertion, and/or addition of 1 to 10 amino acid residues, and wherein said protein, when overexpressed in the coryneform bacterium, imparts improved L-glutamic acid-producing ability to the coryneform bacterium; (c) a protein comprising an amino acid sequence having an identity of 90% or higher to the amino acid sequence of SEQ ID NO: 10, and wherein said protein, when overexpressed in the coryneform bacterium, imparts improved L-glutamic acid-producing ability to the coryneform bacterium.

According to the present invention, an L-amino acid-producing ability of a bacterium can be improved, and an L-amino acid can be efficiently produced.

DETAILED DESCRIPTION OF THE PREFERRED EMBODIMENTS

Figure 1A:
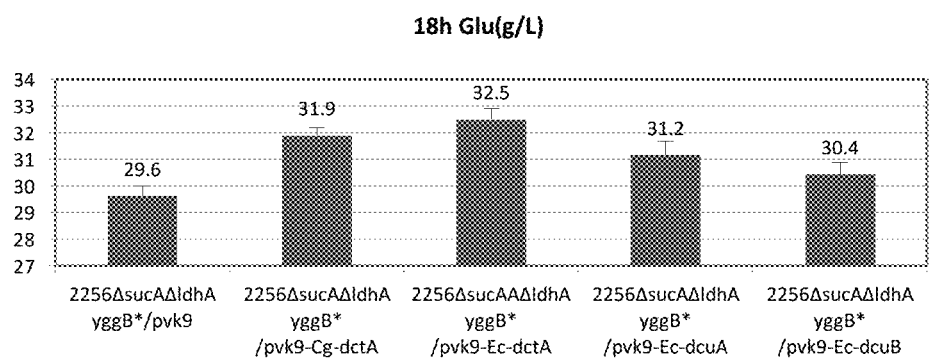
FIG. 1A shows the results of a glutamic acid production culture using a *C. glutamicum* strain having enhanced expression of a C4-dicarboxylic acid-uptake carrier gene (Cg-dctA, Ec-dctA, Ec-dcuA, or Ec-dcuB) for production and accumulation of. glutamic acid (Glu)

The method as described herein is a method for producing an L-amino acid that can include the steps of culturing a bacterium having an L-amino acid-producing ability in a medium to accumulate an L-amino acid in the medium and/or cells of the bacterium, and collecting the L-amino acid from the medium and/or cells of the bacterium, wherein the bacterium has been modified so that the activity of a C4-dicarboxylic acid-uptake carrier is increased. The bacterium used for this method can also be referred to as "bacterium of the present invention".

<1> Bacterium

The bacterium as described herein is a bacterium having an ability to produce an L-amino acid, which has been modified so that the activity of a C4-dicarboxylic acid-uptake carrier is increased.

<1-1> Bacterium Having L-Amino Acid-Producing Ability

The phrase "bacterium having an L-amino acid-producing ability" or "bacterium having an ability to produce an L-amino acid" can refer to a bacterium having an ability to generate and accumulate an objective L-amino acid in a medium and/or the cells of the bacterium to such a degree that the L-amino acid can be collected, when the bacterium is cultured in the medium. The bacterium having an L-amino acid-producing ability may be a bacterium that is able to accumulate an objective L-amino acid in a medium and/or the cells of the bacterium in an amount larger than that obtainable with a non-modified strain. The term "non-modified strain" can refer to a control strain that has not been modified so that the activity of a C4-dicarboxylic acid-uptake carrier is increased. That is, examples of the non-modified strain can include a wild-type strain and parental strain. The bacterium having an L-amino acid-producing ability may be a bacterium that is able to accumulate an objective L-amino acid in a medium in an amount of 0.5 g/L or more, or 1.0 g/L or more.

The L-amino acid produced in the method as described herein can be an L-amino acid other than L-aspartic acid. Examples of the L-amino acid other than L-aspartic acid can include basic amino acids such as L-lysine, L-ornithine, L-arginine, L-histidine, and L-citrulline; aliphatic amino acids such as L-isoleucine, L-alanine, L-valine, L-leucine, and glycine; amino acids which are hydroxy-monoaminocarboxylic acids such as L-threonine and L-serine; cyclic amino acids such as L-proline; aromatic amino acids such as L-phenylalanine, L-tyrosine, and L-tryptophan; sulfur-containing amino acids such as L-cysteine, L-cystine, and L-methionine; acidic amino acids such as L-glutamic acid; and amino acids having an amide group in the side chain such as L-glutamine and L-asparagine. Particular examples of the L-amino acid other than L-aspartic acid can include L-amino acid of glutamate family and L-amino acid of aspartate family. The term "L-amino acid of glutamate family" collectively can refer to L-glutamic acid and L-amino acids that are biosynthesized via L-glutamic acid as an intermediate. Examples of the L-amino acids that are biosynthesized via L-glutamic acid as an intermediate can include L-glutamine, L-proline, L-arginine, L-citrulline, and L-ornithine. The term "L-amino acid of aspartate family" collectively can refer to L-amino acids that are biosynthesized via L-aspartic acid as an intermediate, and does not include L-aspartic acid per se. Examples of the L-amino acids that are biosynthesized via L-aspartic acid as an intermediate can include L-lysine, L-threonine, L-isoleucine, and L-methionine. More particular examples of the L-amino acid other than L-aspartic acid can include L-glutamic acid. For example, at least when the C4-dicarboxylic acid-uptake carrier is a protein encoded by a dctA gene, the L-amino acid may be L-glutamic acid. The bacterium may have an ability to produce a single kind of L-amino acid, or two or more kinds of L-amino acids.

The term "amino acid" can refer to an L-amino acid, unless otherwise stated. The term "L-amino acid" can refer to an L-amino acid in a free form, a salt thereof, or a mixture thereof, unless otherwise stated. Examples of a salt are described herein.

Examples of the bacterium can include bacteria belonging to the family Enterobacteriaceae and coryneform bacteria.

Examples of bacteria belonging to the family Enterobacteriaceae can include bacteria belonging to the genus *Escherichia, Enterobacter, Pantoea, Klebsiella, Serratia, Erwinia, Photorhabdus, Providencia, Salmonella, Morganella*, or the like. Specifically, bacteria classified into the family Enterobacteriaceae according to the taxonomy used in the NCBI (National Center for Biotechnology Information) database (ncbi.nlm.nih.gov/Taxonomy/Browser/wwwtax.cgi?id=91347) can be used.

The *Escherichia* bacteria are not particularly limited, and examples thereof can include those classified into the genus *Escherichia* according to the taxonomy known to those skilled in the field of microbiology. Examples of the *Escherichia* bacteria can include, for example, those described in the work of Neidhardt et al. (Backmann B. J., 1996, Derivations and Genotypes of some mutant derivatives of *Escherichia coli* K-12, pp. 2460-2488, Table 1, In F. D. Neidhardt (ed.), *Escherichia coli* and *Salmonella* Cellular and Molecular Biology/Second Edition, American Society for Microbiology Press, Washington, D.C.). Examples of the *Escherichia* bacteria can include, for example, *Escherichia coli*. Specific examples of *Escherichia coli* can include, for example, *Escherichia coli* K-12 strains such as W3110 strain (ATCC 27325) and MG1655 strain (ATCC 47076); *Escherichia coli* K5 strain (ATCC 23506); *Escherichia coli* B strains such as BL21 (DE3) strain; and derivative strains thereof.

The *Enterobacter* bacteria are not particularly limited, and examples can include those classified into the genus *Enterobacter* according to the taxonomy known to those skilled in the field of microbiology. Examples the *Enterobacter* bacterium can include, for example, *Enterobacter agglomerans* and *Enterobacter aerogenes*. Specific examples of *Enterobacter agglomerans* can include, for example, the *Enterobacter agglomerans* ATCC 12287 strain. Specific examples of *Enterobacter aerogenes* can include, for example, the *Enterobacter aerogenes* ATCC 13048 strain, NBRC 12010 strain (Biotechnol. Bioeng., 2007, Mar. 27; 98(2):340-348), and AJ110637 strain (FERM BP-10955). Examples the *Enterobacter* bacteria also can include, for example, the strains described in European Patent Application Laid-open (EP-A) No. 0952221. In addition, *Enterobacter agglomerans* also can include some strains classified as *Pantoea agglomerans*.

The *Pantoea* bacteria are not particularly limited, and examples can include those classified into the genus *Pantoea* according to the taxonomy known to those skilled in the field of microbiology. Examples the *Pantoea* bacteria can include, for example, *Pantoea ananatis, Pantoea stewartii, Pantoea agglomerans*, and *Pantoea citrea*. Specific examples of *Pantoea ananatis* can include, for example, the *Pantoea ananatis* LMG20103 strain, AJ13355 strain (FERM BP-6614), AJ13356 strain (FERM BP-6615), AJ13601 strain (FERM BP-7207), SC17 strain (FERM BP-11091), SC17(0) strain (VKPM B-9246), and SC17sucA strain (FERM BP-8646). Some of *Enterobacter* bacteria and *Erwinia* bacteria were reclassified into the genus *Pantoea* (Int. J. Syst. Bacteriol., 39, 337-345 (1989); Int. J. Syst. Bacteriol., 43, 162-173 (1993)). For example, some strains of *Enterobacter agglomerans* were recently reclassified into *Pantoea agglomerans, Pantoea ananatis, Pantoea stewartii*, or the like on the basis of nucleotide sequence analysis of 16S rRNA etc. (Int. J. Syst. Bacteriol., 39, 337-345 (1989)). The *Pantoea* bacteria can include those reclassified into the genus *Pantoea* as described above.

Examples of the *Erwinia* bacteria can include *Erwinia amylovora* and *Erwinia carotovora*. Examples of the *Klebsiella* bacteria can include *Klebsiella planticola*.

Examples of the coryneform bacteria can include bacteria belonging to the genus *Corynebacterium, Brevibacterium, Microbacterium*, or the like.

Specific examples of the coryneform bacteria can include the following species:
*Corynebacterium acetoacidophilum*
*Corynebacterium acetoglutamicum*
*Corynebacterium alkanolyticum*
*Corynebacterium callunae*
*Corynebacterium crenatum*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum* (*Corynebacterium glutamicum*)
*Brevibacterium flavum* (*Corynebacterium glutamicum*)

*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Corynebacterium ammoniagenes* (*Corynebacterium stationis*)
*Brevibacterium album*
*Brevibacterium cerinum*
*Microbacterium ammoniaphilum*

Specific examples of the coryneform bacteria can include the following strains:
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium crenatum* AS1.542
*Corynebacterium glutamicum* ATCC 13020, ATCC 13032, ATCC 13060, ATCC 13869, FERM BP-734
*Corynebacterium lilium* ATCC 15990
*Corynebacterium melassecola* ATCC 17965
*Corynebacterium efficiens* (*Corynebacterium thermoaminogenes*) AJ12340 (FERM BP-1539)
*Corynebacterium herculis* ATCC 13868
*Brevibacterium divaricatum* (*Corynebacterium glutamicum*) ATCC 14020
*Brevibacterium flavum* (*Corynebacterium glutamicum*) ATCC 13826, ATCC 14067, AJ12418 (FERM BP-2205)
*Brevibacterium immariophilum* ATCC 14068
*Brevibacterium lactofermentum* (*Corynebacterium glutamicum*) ATCC 13869
*Brevibacterium roseum* ATCC 13825
*Brevibacterium saccharolyticum* ATCC 14066
*Brevibacterium thiogenitalis* ATCC 19240
*Corynebacterium ammoniagenes* (*Corynebacterium stationis*) ATCC 6871, ATCC 6872
*Brevibacterium album* ATCC 15111
*Brevibacterium cerinum* ATCC 15112
*Microbacterium ammoniaphilum* ATCC 15354

The *Corynebacterium* bacteria can include bacteria that had previously been classified into the genus *Brevibacterium*, but are presently united into the genus *Corynebacterium* (Int. J. Syst. Bacteriol., 41, 255 (1991)). Moreover, *Corynebacterium stationis* can include bacteria that had previously been classified as *Corynebacterium ammoniagenes*, but are presently re-classified into *Corynebacterium stationis* on the basis of nucleotide sequence analysis of 16S rRNA etc. (Int. J. Syst. Evol. Microbiol., 60, 874-879 (2010)).

These strains are available from, for example, the American Type Culture Collection (Address: P.O. Box 1549, Manassas, Va. 20108, United States of America). That is, registration numbers are given to the respective strains, and the strains can be ordered by using these registration numbers (refer to atcc.org). The registration numbers of the strains are listed in the catalogue of the American Type Culture Collection. These strains can also be obtained from, for example, the depositories at which the strains were deposited.

The bacterium may be a bacterium inherently having an L-amino acid-producing ability, or may be a bacterium modified so that it has an L-amino acid-producing ability. The bacterium having an L-amino acid-producing ability can be obtained by imparting an L-amino acid-producing ability to such a bacterium as described above, or by enhancing an L-amino acid-producing ability of such a bacterium as described above.

To impart or enhance an L-amino acid-producing ability, methods conventionally employed in the breeding of amino acid-producing strains of coryneform bacteria, *Escherichia* bacteria, and so forth (refer to "Amino Acid Fermentation", Gakkai Shuppan Center (Ltd.), 1st Edition, published May 30, 1986, pp. 77-100) can be used. Examples of such methods can include, for example, acquiring an auxotrophic mutant strain, acquiring an L-amino acid analogue-resistant strain, acquiring a metabolic regulation mutant strain, and constructing a recombinant strain in which the activity of an L-amino acid biosynthetic enzyme is enhanced. In the breeding of L-amino acid-producing bacteria, one of the above-described properties such as auxotrophy, analogue resistance, and metabolic regulation mutation may be imparted alone, or two or three or more of such properties may be imparted in combination. Also, in the breeding of L-amino acid-producing bacteria, the activity of one of L-amino acid biosynthetic enzymes may be enhanced alone, or the activities of two or three or more of such enzymes may be enhanced in combination. Furthermore, imparting property(s) such as auxotrophy, analogue resistance, and metabolic regulation mutation can be combined with enhancing the activity(s) of biosynthetic enzyme(s).

An auxotrophic mutant strain, analogue-resistant strain, or metabolic regulation mutant strain having an L-amino acid-producing ability can be obtained by subjecting a parental strain or wild-type strain to a usual mutagenesis treatment, and then selecting a strain exhibiting autotrophy, analogue resistance, or a metabolic regulation mutation, and having an L-amino acid-producing ability from the obtained mutant strains. Examples of the usual mutagenesis treatment can include irradiation of X-ray or ultraviolet and a treatment with a mutation agent such as N-methyl-N'-nitro-N-nitrosoguanidine (MNNG), ethyl methanesulfonate (EMS), and methyl methanesulfonate (MMS).

An L-amino acid-producing ability can also be imparted or enhanced by enhancing the activity of an enzyme involved in biosynthesis of an objective L-amino acid. An enzyme activity can be enhanced by, for example, modifying a bacterium so that the expression of a gene encoding the enzyme is enhanced. Methods for enhancing gene expression are described in WO00/18935, EP1010755A, and so forth. The detailed procedures for enhancing enzyme activity are described herein.

Furthermore, an L-amino acid-producing ability can also be imparted or enhanced by reducing the activity of an enzyme that catalyzes a reaction branching away from the biosynthetic pathway of an objective L-amino acid to generate a compound other than the objective L-amino acid. The "enzyme that catalyzes a reaction branching away from the biosynthetic pathway of an objective L-amino acid to generate a compound other than the objective L-amino acid" can include an enzyme involved in decomposition of the objective amino acid. The method for reducing an enzyme activity are described herein.

Hereinafter, L-amino acid-producing bacteria and methods for imparting or enhancing an L-amino acid-producing ability will be specifically exemplified. All of the properties of the L-amino acid-producing bacteria and modifications for imparting or enhancing an L-amino acid-producing ability may be used independently or in any appropriate combination.

<L-Glutamic Acid-Producing Bacteria>

Examples of methods for imparting or enhancing L-glutamic acid-producing ability can include, for example, a method of modifying a bacterium so that the bacterium has an increased activity or activities of one or more of the L-glutamic acid biosynthesis enzymes. Examples of such enzymes can include, but are not particularly limited to, glutamate dehydrogenase (gdhA), glutamine synthetase (glnA), glutamate synthase (gltBD), isocitrate dehydrogenase (icdA), aconitate hydratase (acnA, acnB), citrate synthase (OA), methylcitrate synthase (prpC), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), glucose phosphate isomerase (pgi), 6-phosphogluconate dehydratase (edd), 2-keto-3-deoxy-6-phosphogluconate aldolase (eda), and transhydrogenase. Shown in the parentheses after the names of the enzymes are examples of genes encoding the enzymes (the same shall apply throughout this specification). It is preferable to enhance the activity or activities of one or more kinds of enzymes such as, for example, glutamate dehydrogenase, citrate synthase, phosphoenol pyruvate carboxylase, and methylcitrate synthase.

Examples of strains belonging to the family Enterobacteriaceae and modified so that the expression of the citrate synthase gene, phosphoenolpyruvate carboxylase gene, and/or glutamate dehydrogenase gene are increased can include those disclosed in EP1078989A, EP955368A, and EP952221A. Furthermore, examples of strains belonging to the family Enterobacteriaceae and modified so that the expression of a gene of the Entner-Doudoroff pathway (edd, eda) is increased can include those disclosed in EP1352966B. Examples of coryneform bacteria modified so that the expression of the glutamate synthetase gene (gltBD) is increased can include those disclosed in WO99/07853.

Examples of methods for imparting or enhancing L-glutamic acid-producing ability also can include, for example, a method of modifying a bacterium so that the bacterium has a reduced activity or activities of one or more kinds of enzymes that catalyze a reaction branching away from the biosynthesis pathway of L-glutamic acid to generate a compound other than L-glutamic acid. Examples of such enzymes can include, but are not particularly limited to, isocitrate lyase (aceA), α-ketoglutarate dehydrogenase (sucA, odhA), acetolactate synthase WO, formate acetyltransferase (pfl), lactate dehydrogenase (ldh), alcohol dehydrogenase (adh), glutamate decarboxylase (gadAB), and succinate dehydrogenase (sdhABCD). It is a particular example to reduce or delete, for example, the α-ketoglutarate dehydrogenase activity.

*Escherichia* bacteria having a reduced α-ketoglutarate dehydrogenase activity or that are deficient in α-ketoglutarate dehydrogenase activity, and methods for obtaining them are described in U.S. Pat. Nos. 5,378,616 and 5,573,945. Furthermore, methods for reducing or deleting α-ketoglutarate dehydrogenase activity of Enterobacteriaceae bacteria such as *Pantoea* bacteria, *Enterobacter* bacteria, *Klebsiella* bacteria, and *Erwinia* bacteria are disclosed in U.S. Pat. Nos. 6,197,559, 6,682,912, 6,331,419, and 8,129,151, and WO2008/075483. Specific examples of *Escherichia* bacteria with reduced α-ketoglutarate dehydrogenase activity or deficient in the α-ketoglutarate dehydrogenase activity can include the following strains:

*E. coli* W3110sucA::Km$^r$
*E. coli* AJ12624 (FERM BP-3853)
*E. coli* AJ12628 (FERM BP-3854)
*E. coli* AJ12949 (FERM BP-4881)

*E. coli* W3110sucA::Km$^r$ is a strain obtained by disrupting the sucA gene encoding α-ketoglutarate dehydrogenase of *E. coli* W3110. This strain is completely deficient in α-ketoglutarate dehydrogenase activity.

Coryneform bacteria in which the α-ketoglutarate dehydrogenase activity is reduced or eliminated, and methods for obtaining such bacteria are disclosed in WO2008/075483. Specific examples of coryneform bacteria in which the α-ketoglutarate dehydrogenase activity is reduced or eliminated can include, for example, the following strains:

*Corynebacterium glutamicum* (*Brevibacterium lactofermentum*) L30-2 strain (Japanese Patent Laid-open (Kokai) No. 2006-340603)

*Corynebacterium glutamicum* (*Brevibacterium lactofermentum*) AS strain (WO95/34672)

*Corynebacterium glutamicum* (*Brevibacterium lactofermentum*) AJ12821 (FERM BP-4172, French Patent No. 9401748)

*Corynebacterium glutamicum* (*Brevibacterium flavum*) AJ12822 (FERM BP-4173, French Patent No. 9401748)

*Corynebacterium glutamicum* AJ12823 (FERM BP-4174, French Patent No. 9401748)

Examples of L-glutamic acid-producing bacteria and parental strains that can be used to derive them also can include *Pantoea* bacteria, such as the *Pantoea ananatis* AJ13355 strain (FERM BP-6614), *Pantoea ananatis* SC17 strain (FERM BP-11091), and *Pantoea ananatis* SC17(0) strain (VKPM B-9246). The AJ13355 strain is isolated from soil in Iwata-shi, Shizuoka-ken, Japan as a strain that can proliferate in a low pH medium containing L-glutamic acid and a carbon source. The SC17 strain is a strain selected as a low phlegm-producing mutant strain from the AJ13355 strain (U.S. Pat. No. 6,596,517). The SC17 strain was deposited at the independent administrative agency, National Institute of Advanced Industrial Science and Technology, International Patent Organism Depositary (currently independent administrative agency, National Institute of Technology and Evaluation, International Patent Organism Depositary, #120, 2-5-8 Kazusakamatari, Kisarazu-shi, Chiba-ken, 292-0818, Japan) on Feb. 4, 2009, and assigned an accession number of FERM BP-11091. The AJ13355 strain was deposited at the National Institute of Bioscience and Human Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 19, 1998 and assigned an accession number of FERM P-16644. Then, the deposit was converted to an international deposit under the provisions of Budapest Treaty on Jan. 11, 1999, and assigned an accession number of FERM BP-6614.

Furthermore, examples of L-glutamic acid-producing bacteria and parental strains that can be used to derive them also can include *Pantoea* bacteria with reduced α-ketoglutarate dehydrogenase activity or that are deficient in α-ketoglutarate dehydrogenase activity. Examples of such strains can include the AJ13356 strain (U.S. Pat. No. 6,331,419), which is an α-ketoglutarate dehydrogenase E1 subunit (sucA) gene-deficient strain of the AJ13355 strain, and the SC17sucA strain (U.S. Pat. No. 6,596,517), which is a sucA gene-deficient strain of the SC17 strain. The AJ13356 strain was deposited at the National Institute of Bioscience and Human-Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb.

19, 1998, and assigned an accession number of FERM P-16645. Then, the deposit was converted to an international deposit under the provisions of the Budapest Treaty on Jan. 11, 1999, and assigned an accession number of FERM BP-6616. The SC17sucA strain was assigned a private number of AJ417, and deposited at the independent administrative agency, National Institute of Advanced Industrial Science and Technology, International Patent Organism Depositary (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 26, 2004, under an accession number of FERM BP-8646.

The AJ13355 strain was identified as *Enterobacter agglomerans* when it was isolated, but it was recently reclassified as *Pantoea ananatis* on the basis of nucleotide sequencing of 16S rRNA and so forth. Therefore, although the AJ13355 and AJ13356 strains are deposited at the aforementioned depository as *Enterobacter agglomerans*, they are referred to as *Pantoea ananatis* in this specification.

Furthermore, examples of L-glutamic acid-producing bacteria and parental strains that can be used to derive them also can include *Pantoea* bacteria such as the *Pantoea ananatis* SC17sucA/RSFCPG+pSTVCB strain, *Pantoea ananatis* AJ13601 strain, *Pantoea ananatis* NP106 strain, and *Pantoea ananatis* NA1 strain. The SC17sucA/RSFCPG+pSTVCB strain was obtained by introducing the plasmid RSFCPG containing the citrate synthase gene (OA), phosphoenolpyruvate carboxylase gene (ppc), and glutamate dehydrogenase gene (gdhA) derived from *Escherichia coli*, and the plasmid pSTVCB containing the citrate synthase gene (OA) derived from *Brevibacterium lactofermentum*, into the SC17sucA strain. The AJ13601 strain was derived from the SC17sucA/RSFCPG+pSTVCB strain as a strain resistant to a high concentration of L-glutamic acid at a low pH. The NP106 strain was obtained from the AJ13601 strain by curing the RSFCPG and pSTVCB plasmids. The NA1 strain was obtained from the NP106 strain by introducing the plasmid RSFPPG thereinto (WO2010/027045). The plasmid RSFPPG has a structure corresponding to the plasmid RSFCPG except that gltA gene thereof has been replaced with a methylcitrate synthase gene (prpC), and hence, contains the prpC gene, ppc gene, and gdhA gene (WO2008/020654). The AJ13601 strain was deposited at the National Institute of Bioscience and Human Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Aug. 18, 1999, and assigned an accession number FERM P-17516. Then, the deposit was converted to an international deposit under the provisions of the Budapest Treaty on Jul. 6, 2000, and assigned an accession number FERM BP-7207.

Examples of L-glutamic acid-producing bacteria and parental strains that can be used to derive them also can include strains in which both the α-ketoglutarate dehydrogenase (sucA) activity and the succinate dehydrogenase (sdh) activity are reduced or deleted (Japanese Patent Laid-open (Kokai) No. 2010-041920). Specific examples of such strains can include, for example, a sucAsdhA double-deficient strain of the *Pantoea ananatis* NA1 strain and an odhAsdhA double-deficient strain of the *Corynebacterium glutamicum* ATCC 14067 strain, i.e. the *Corynebacterium glutamicum* 8L3GASDH strain (Japanese Patent Laid-open (Kokai) No. 2010-041920).

Examples of L-glutamic acid-producing bacteria and parental strains that can be used to derive them also can include auxotrophic mutant strains. Specific examples of auxotrophic mutant strains can include, for example, *E. coli* VL334thrC$^+$ (VKPM B-8961, EP1172433). *E. coli* VL334 (VKPM B-1641) is an L-isoleucine and L-threonine auxotrophic strain having mutations in the thrC and ilvA genes (U.S. Pat. No. 4,278,765). *E. coli* VL334thrC$^+$ is an L-isoleucine-auxotrophic L-glutamic acid-producing bacterium obtained by introducing a wild-type allele of the thrC gene into the VL334 strain. The wild-type allele of the thrC gene was introduced by the method of general transduction using a bacteriophage P1 grown on the wild-type *E. coli* K-12 strain (VKPM B-7) cells.

Examples of L-glutamic acid-producing bacteria and parental strains that can be used to derive them also can include strains having resistance to an aspartic acid analogue. Such strains can also be deficient in the α-ketoglutarate dehydrogenase activity. Specific examples of strains having resistance to an aspartic acid analogue and deficient in α-ketoglutarate dehydrogenase activity can include, for example, *E. coli* AJ13199 (FERM BP-5807, U.S. Pat. No. 5,908,768), *E. coli* FFRM P-12379, which additionally has a lowered L-glutamic acid-decomposing ability (U.S. Pat. No. 5,393,671), and *E. coli* AJ13138 (FERM BP-5565, U.S. Pat. No. 6,110,714).

Examples of methods for imparting or enhancing L-glutamic acid-producing ability also can include, for example, a method of enhancing the expression of an L-glutamic acid secretion gene, such as yhfK gene (WO2005/085419) or ybjL gene (WO2008/133161).

Furthermore, examples of methods for imparting or enhancing L-glutamic acid-producing ability to or in coryneform bacteria also can include methods of imparting resistance to an organic acid analogue, respiratory inhibitor, or the like, and methods of imparting sensitivity to a cell wall synthesis inhibitor. Specific examples of such methods can include, for example, imparting monofluoroacetic acid resistance (Japanese Patent Laid-open (Kokai) No. 50-113209), imparting adenine resistance or thymine resistance (Japanese Patent Laid-open (Kokai) No. 57-065198), attenuating urease (Japanese Patent Laid-open (Kokai) No. 52-038088), imparting malonic acid resistance (Japanese Patent Laid-open (Kokai) No. 52-038088), imparting resistance to benzopyrones or naphthoquinones (Japanese Patent Laid-open (Kokai) No. 56-1889), imparting HOQNO resistance (Japanese Patent Laid-open (Kokai) No. 56-140895), imparting α-ketomalonic acid resistance (Japanese Patent Laid-open (Kokai) No. 57-2689), imparting guanidine resistance (Japanese Patent Laid-open (Kokai) No. 56-35981), imparting sensitivity to penicillin (Japanese Patent Laid-open (Kokai) No. 4-88994), and so forth.

Specific examples of such resistant or sensitive bacteria can include the following strains:

*Corynebacterium glutamicum* (*Brevibacterium flavum*) AJ3949 (FERM BP-2632, Japanese Patent Laid-open (Kokai) No. 50-113209)

*Corynebacterium glutamicum* AJ11628 (FERM P-5736, Japanese Patent Laid-open (Kokai) No. 57-065198)

*Corynebacterium glutamicum* (*Brevibacterium flavum*) AJ11355 (FERM P-5007, Japanese Patent Laid-open (Kokai) No. 56-1889)

*Corynebacterium glutamicum* AJ11368 (FERM P-5020, Japanese Patent Laid-open (Kokai) No. 56-1889)

*Corynebacterium glutamicum* (*Brevibacterium flavum*) AJ11217 (FERM P-4318, Japanese Patent Laid-open (Kokai) No. 57-2869)

*Corynebacterium glutamicum* AJ11218 (FERM P-4319, Japanese Patent Laid-open (Kokai) No. 57-2869)

*Corynebacterium glutamicum* (*Brevibacterium flavum*) AJ11564 (FERM BP-5472, Japanese Patent Laid-open (Kokai) No. 56-140895)

*Corynebacterium glutamicum* (*Brevibacterium flavum*) AJ11439 (FERM BP-5136, Japanese Patent Laid-open (Kokai) No. 56-35981)

*Corynebacterium glutamicum* H7684 (FERM BP-3004, Japanese Patent Laid-open (Kokai) No. 04-88994)

*Corynebacterium glutamicum* (*Brevibacterium lactofermentum*) AJ11426 (FERM P-5123, Japanese Patent Laid-open (Kokai) No. 56-048890)

*Corynebacterium glutamicum* AJ11440 (FERM P-5137, Japanese Patent Laid-open (Kokai) No. 56-048890)

*Corynebacterium glutamicum* (*Brevibacterium lactofermentum*) AJ11796 (FERM P-6402, Japanese Patent Laid-open (Kokai) No. 58-158192)

Furthermore, examples of methods for imparting or enhancing L-glutamic acid-producing ability to or in coryneform bacteria also can include a method of enhancing the expression of a yggB gene and a method of introducing a mutant yggB gene having a mutation in the coding region (WO2006/070944). That is, the bacterium may have been modified so that the expression of yggB gene is increased, or may have been modified so as to harbor (have) a mutant yggB gene.

The yggB gene encodes a mechanosensitive channel. Examples of the yggB gene can include the yggB genes of coryneform bacteria. Specific examples of the yggB genes of coryneform bacteria can include, for example, yggB genes of *Corynebacterium glutamicum* ATCC13869, *Corynebacterium glutamicum* ATCC13032, *Corynebacterium glutamicum* ATCC14967, and *Corynebacterium melassecola* ATCC17965 (WO2006/070944). The yggB gene of *Corynebacterium glutamicum* ATCC 13032 corresponds to the sequence complementary to the sequence of the nucleotide numbers 1,336,091 to 1,337,692 in the genome sequence registered as Genbank Accession No. NC_003450 in the NCBI database, and is also called NCgl1221. The YggB protein encoded by the yggB gene of *Corynebacterium glutamicum* ATCC 13032 is registered as GenBank accession No. NP_600492. In addition, the nucleotide sequence of the yggB gene of *Corynebacterium glutamicum* 2256 (ATCC 13869) and the amino acid sequence of the YggB protein encoded by the gene are shown in SEQ ID NOS: 9 and 10, respectively.

A yggB gene having the "specific mutation" described herein can also be referred to as a "mutant yggB gene", and a protein encoded thereby can also be referred to as a "mutant YggB protein". Furthermore, a yggB gene not having the "specific mutation" described herein can also be referred to as a "wild-type yggB gene", and a protein encoded thereby can also be referred to as a "wild-type YggB protein". Incidentally, as for the YggB protein, a change of the amino acid sequence caused by the "specific mutation" in the yggB gene can also be referred to as a "specific mutation". The term "wild-type" is used for convenience to distinguish the "wild-type" yggB gene or YggB protein from the "mutant" yggB gene or YggB protein, and the "wild-type" yggB gene or YggB protein is not limited to those obtained as natural substances, so long as it does not have the "specific mutation". Examples of the wild-type YggB protein can include the YggB proteins exemplified above, such as YggB protein having the amino acid sequence of SEQ ID NO: 10. Examples of the wild-type YggB protein also can include conservative variants, that is, variants in which the original function thereof is maintained, of the YggB proteins exemplified above, provided that the conservative variants do not have the "specific mutation". The "original function" regarding the YggB protein may be, for example, a function as a mechanosensitive channel or a property that an increased expression thereof in a coryneform bacterium provides an improved L-glutamic acid-producing ability of the coryneform bacterium.

The "specific mutation" is not particularly limited, so long as it changes the amino acid sequence of the YggB protein as described above to thereby improve an L-glutamic acid-producing ability of a coryneform bacterium. Examples of the "specific mutation" can include a mutation on the C-terminus side and a mutation in a transmembrane region. The "specific mutation" may also be a combination of these.

(1) Mutation on C-Terminus Side

The mutation on the C-terminus side can be a mutation introduced into a region of the wild-type yggB gene coding for the amino acid residues at the positions 419 to 533 of the wild-type YggB protein. The mutation on the C-terminus side may be introduced at one or more sites in the region. The type of change of the amino acid sequence induced by the mutation on the C-terminus side is not particularly limited. The mutation on the C-terminus side may be an amino acid substitution (missense mutation), insertion of amino acid residue, deletion of amino acid residue, introduction of stop codon (nonsense mutation), frame shift mutation, or a combination of these. The mutation on the C-terminus side can be, for example, a mutation wherein a nucleotide sequence such as an insertion sequence (henceforth also referred to as "IS") or transposon is inserted.

(1-1) Insertion of Nucleotide Sequence

Examples of the mutation on the C-terminus side can include, for example, a mutation that results in the insertion of a nucleotide sequence at the site coding for the valine residue at the position 419 of the wild-type YggB protein (2A-1 type mutation). The 2A-1 type mutation may be, for example, a mutation that causes deletion or substitution of a part or all of the amino acid residues at the positions 419 to 533 of the wild-type YggB protein. Specific examples of the mutant yggB gene having the 2A-1 type mutation can include, for example, the yggB gene including IS inserted into the next of "G" at the position 1255 in SEQ ID NO: 9, and thereby coding for a mutant YggB protein having a full length of 423 amino residues, which is shorter than that of the original wild-type YggB protein (SEQ ID NO: 10). The nucleotide sequence of this mutant yggB gene (V419::IS) and the amino acid sequence of the mutant YggB protein encoded by the gene are shown in SEQ ID NOS: 11 and 12, respectively. In the SEQ ID NO: 11, the positions 1 to 1269 correspond to CDS for this mutant YggB protein (V419::IS). Specific examples of the L-glutamic acid-producing bacterium having the mutant yggB gene (V419::IS) can include, for example, the *C. glutamicum* 2256ΔsucAΔldhA yggB* strain (WO2014/185430).

(1-2) Substitution for Proline Residues

Examples of the mutation on the C-terminus side also can include, for example, a mutation that replaces a proline residue present within the positions 419 to 533 of the wild-type YggB protein with another amino acid residue. Examples of such a proline residue can include the proline residues at the positions 424, 437, 453, 457, 462, 469, 484, 489, 497, 515, 529, and 533 of the wild-type YggB protein. It is especially preferable to replace the proline residue(s) of the position(s) 424 and/or 437 with other amino acid residue(s). The "other amino acid" is not particularly limited so long as it is a naturally occurring amino acid other than proline. Examples of the "other amino acid" can include Lys, Glu, Thr, Val, Leu, Ile, Ser, Asp, Asn, Gln, Arg, Cys, Met, Phe, Trp, Tyr, Gly, Ala, and His. For example, the proline residue at the position 424 may be replaced with a hydrophobic amino acid, such as Ala, Gly, Val, Leu, or Ile, or a branched chain amino acid, such as Leu, Val, or Ile. Furthermore, for example, the proline residue at position 437 may be replaced with an amino acid having a hydroxyl group in the side chain, such as Thr, Ser, or Tyr, or with a Ser residue.

(2) Mutation in Transmembrane Region

The YggB protein is estimated to have five transmembrane regions. The transmembrane regions correspond to the amino acid residues at the positions 1 to 23 (first transmembrane region), the positions 25 to 47 (second transmembrane region), the positions 62 to 84 (third transmembrane region), the positions 86 to 108 (fourth transmembrane region), and the positions 110 to 132 (fifth transmembrane region) of the wild-type YggB protein. The mutation in a transmembrane region can be in the regions coding for these transmembrane regions of the wild-type yggB gene. The mutation in transmembrane region may be introduced into one or more sites in the regions. The mutation in transmembrane region can be a mutation that induces substitution, deletion, addition, insertion, or inversion of one or several amino acid residues, but does not include any frame shift mutation or nonsense mutation. The number meant by the term "one or several" can be 1 to 20, 1 to 10, 1 to 5, or 1 to 3. Examples of the mutation in a transmembrane region can include a mutation that inserts one or several amino acid residues, such as Cys-Ser-Leu, between the leucine residue at position 14 and the tryptophan residue at position 15; a mutation that replaces the alanine residue at position 100 with another amino acid residue, such as an amino acid having a hydroxyl group in the side chain (i.e. Thr, Ser, or Tyr), such as a Thr residue; a mutation that replaces the alanine residue at position 111 with another amino acid residue such as a residue of an amino acid having hydroxyl group in the side chain (i.e. Thr, Ser, or Tyr), such as a Thr residue; in the wild-type YggB protein.

The phrase "amino acid residue at the position X of the wild-type YggB protein" can mean the amino acid residue at position X in SEQ ID NO: 10, unless otherwise stated. The "position X" in an amino acid sequence is the X-th position counted from the N-terminus of the amino acid sequence, and the amino acid residue of the N-terminus is the amino acid residue of the position 1. That is, the aforementioned positions of amino acid residues indicate relative positions, and the absolute positions thereof may shift due to deletion, insertion, addition, or the like of an amino acid residue or residues. For example, the "amino acid residue at the position 419 of the wild-type YggB protein" can mean the amino acid residue corresponding to position 419 in SEQ ID NO: 10, and when one amino acid residue is deleted at a position on the N-terminus side of position 419, the 418th amino acid residue from the N-terminus is "the amino acid residue at position 419 of the wild-type YggB protein". Furthermore, when one amino acid residue is inserted at a position on the N-terminus side of position 419, the 420th amino acid residue from the N-terminus is "the amino acid residue at the position 419 of the wild-type YggB protein". Specifically, for example, amino acid residues of the positions 419 to 529 of the YggB protein of *Corynebacterium glutamicum* ATCC14967 correspond to amino acid residues at positions 419 to 533 of the wild-type YggB protein.

Which amino acid residue is "the amino acid residue corresponding to position X in SEQ ID NO: 10" in the amino acid sequence of an arbitrary YggB protein can be determined by alignment between the amino acid sequence of the arbitrary YggB protein and the amino acid sequence of SEQ ID NO: 10. The alignment can be performed by, for example, using known gene analysis software. Specific examples of such software can include DNASIS produced by Hitachi Solutions, GENETYX produced by Genetyx, and so forth (Elizabeth C. Tyler et al., Computers and Biomedical Research, 24 (1) 72-96, 1991; Barton G J et al., Journal of Molecular Biology, 198 (2), 327-37, 1987).

A mutant yggB gene can be obtained by modifying a wild-type yggB gene so as to have the aforementioned "specific mutation". The modification of DNA can be performed by a known method. For example, an objective mutation can be introduced into an objective site of DNA by the site-specific mutation method. Specific examples of the site-specific mutation method can include, for example, a method of using PCR (Higuchi, R., 61, in PCR Technology, Erlich, H. A. Eds., Stockton Press, 1989; Carter P., Meth. In Enzymol., 154, 382, 1987), and a method of using a phage (Kramer, W. and Frits, H. J., Meth. in Enzymol., 154, 350, 1987; Kunkel, T. A. et al., Meth. in Enzymol., 154, 367, 1987). Furthermore, a mutant yggB gene can also be obtained by chemical synthesis.

Modification of a bacterium to have a mutant yggB gene can be attained by introducing the mutant yggB gene into the bacterium. This modification can also be attained by introducing a mutation into the yggB gene of the bacterium through natural mutation or a treatment with a mutagen.

The methods for imparting or enhancing L-glutamic acid-producing ability can also be effective for imparting or enhancing an ability to produce L-amino acids that are biosynthesized via L-glutamic acid as an intermediate, such as L-glutamine, L-proline, L-arginine, L-citrulline, and L-ornithine. Hence, a bacterium having an ability to produce any of these L-amino acids that are biosynthesized via L-glutamic acid may have, as required, such a property possessed by an L-glutamic acid-producing bacterium as described above. For example, a bacterium having an ability to produce any of these L-amino acids that are biosynthesized via L-glutamic acid may have been modified so that the activity of α-ketoglutarate dehydrogenase and/or succinate dehydrogenase is reduced.

<L-Glutamine-Producing Bacteria>

Examples of the method for imparting or enhancing L-glutamine-producing ability can include, for example, a method of modifying a bacterium so that the activity or activities of one or more kinds of enzymes such as L-glutamine biosynthesis enzymes are enhanced. Examples of such enzymes can include, but are not particularly limited to, glutamate dehydrogenase (gdhA) and glutamine synthetase (glnA). The glutamine synthetase activity can also be enhanced by disruption of the glutamine adenylyltransferase gene (glnE) or disruption of the PII control protein gene (glnB) (EP1229121).

Examples of the method for imparting or enhancing L-glutamine-producing ability also can include, for example, a method of modifying a bacterium so that the activity or activities of one or more kinds of enzymes that catalyze a reaction branching away from the biosynthesis pathway of L-glutamine to generate a compound other than L-glutamine are reduced. Examples of such enzymes can include, but are not particularly limited to, glutaminase.

Specific examples of L-glutamine-producing bacteria and parent strains that can be used to derive them can include, for example, coryneform bacteria in which the activity or activities of glutamate dehydrogenase (gdhA) and/or glutamine synthetase (glnA) (EP1229121, EP1424398) are enhanced, and coryneform bacteria in which the glutaminase activity (Japanese Patent Laid-open (Kokai) No. 2004-187684) is reduced. Examples of L-glutamine-producing bacteria and parental strains that can be used to derive them can include a strain belonging to the genus *Escherichia* and having a mutant glutamine synthetase in which the tyrosine residue of the position 397 of glutamine synthetase has been replaced with another amino acid residue (US2003/0148474A).

Examples of the methods for imparting or enhancing L-glutamine-producing ability to or in coryneform bacteria also can include the method of imparting 6-diazo-5-oxo-norleucine resistance (Japanese Patent Laid-open (Kokai) No. 3-232497), the method of imparting purine analogue resistance and methionine sulfoxide resistance (Japanese Patent Laid-open (Kokai) No. 61-202694), and the method of imparting α-ketomalonic acid resistance (Japanese Patent Laid-open (Kokai) No. 56-151495). Specific examples of coryneform bacteria having L-glutamine-producing ability can include, for example, the following strains:

*Corynebacterium glutamicum* (*Brevibacterium flavum*) AJ11573 (FERM P-5492, Japanese Patent Laid-open (Kokai) No. 56-151495)

*Corynebacterium glutamicum* (*Brevibacterium flavum*) AJ11576 (FERM BP-10381, Japanese Patent Laid-open (Kokai) No. 56-151495)

*Corynebacterium glutamicum* (*Brevibacterium flavum*) AJ12212 (FERM P-8123, Japanese Patent Laid-open (Kokai) No. 61-202694)

<L-Proline-Producing Bacteria>

Examples of methods for imparting or enhancing L-proline-producing ability can include, for example, a method of modifying a bacterium so that the bacterium has an increased activity or activities of one or more of the L-proline biosynthesis enzymes. Examples of such enzymes can include glutamate-5-kinase (proB), γ-glutamylphosphate reductase, and pyroline-5-carboxylate reductase (putA). For enhancing the activity of such an enzyme, for example, the proB gene encoding a glutamate kinase desensitized to feedback inhibition by L-proline (German Patent No. 3127361) can be used.

Examples of methods for imparting or enhancing L-proline-producing ability also can include, for example, a method of modifying a bacterium so that the bacterium has a reduced activity of an enzyme involved in decomposition of L-proline. Examples of such an enzyme can include proline dehydrogenase and ornithine aminotransferase.

Specific examples of L-proline-producing bacteria and parental strains that can be used to derive them can include, for example, *E. coli* NRRL B-12403 and NRRL B-12404 (British Patent No. 2075056), *E. coli* VKPM B-8012 (Russian Patent Application No. 2000124295), *E. coli* plasmid mutant strains described in German Patent No. 3127361, *E. coli* plasmid mutant strains described by Bloom F. R. et al. (The 15th Miami winter symposium, 1983, p. 34), *E. coli* 702 strain (VKPM B-8011), which is a 3,4-dehydroxyproline and azetidine-2-carboxylate resistant strain, and *E. coli* 702ilvA strain (VKPM B-8012), which is an ilvA gene-deficient strain of the 702 strain (EP1172433).

<L-Threonine-Producing Bacteria>

Examples of methods for imparting or enhancing L-threonine-producing ability can include, for example, a method of modifying a bacterium so that the bacterium has an increased activity or activities of one or more of the L-threonine biosynthesis enzymes. Examples of such enzymes can include, but are not particularly limited to, aspartokinase III (lysC), aspartate semialdehyde dehydrogenase (asd), aspartokinase I (thrA), homoserine kinase (thrB), threonine synthase (thrC), and aspartate aminotransferase (aspartate transaminase) (aspC). Among these enzymes, it is preferable to enhance activity or activities of one or more of aspartokinase III, aspartate semialdehyde dehydrogenase, aspartokinase I, homoserine kinase, aspartate aminotransferase, and threonine synthase. Any of the genes encoding the L-threonine biosynthesis enzymes can be introduced into a bacterium having a reduced ability to decompose threonine. Examples of such a strain in which threonine decomposition is suppressed can include, for example, the *E. coli* TDH6 strain, which is deficient in threonine dehydrogenase activity (Japanese Patent Laid-open (Kokai) No. 2001-346578).

The activities of the L-threonine biosynthesis enzymes are inhibited by the end product, L-threonine. Therefore, when constructing L-threonine-producing strains, it is preferred that the genes of the L-threonine biosynthesis enzymes are modified so that the enzymes are desensitized to feedback inhibition by L-threonine. The aforementioned thrA, thrB, and thrC genes constitute the threonine operon, which forms an attenuator structure. The expression of the threonine operon is inhibited by isoleucine and threonine in the culture broth and also suppressed by attenuation. Therefore, expression of the threonine operon can be enhanced by removing the leader sequence or the attenuator in the attenuation region (Lynn, S. P., Burton, W. S., Donohue, T. J., Gould, R. M., Gumport, R. L, and Gardner, J. F., J. Mol. Biol. 194:59-69 (1987); WO02/26993; WO2005/049808; and WO2003/097839).

The native promoter of the threonine operon is present upstream of the threonine operon, and can be replaced with a non-native promoter (WO98/04715). Also, the threonine operon may be constructed so that the threonine biosynthesis genes are expressed under control of the repressor and promoter of λ-phage (EP0593792B). Furthermore, a bacterium modified so that it is desensitized to feedback inhibition by L-threonine can also be obtained by selecting a strain resistant to α-amino-β-hydroxyisovaleric acid (AHV), which is an L-threonine analogue.

The expression amount of the threonine operon that is modified so as to be desensitized to feedback inhibition by L-threonine as described above can be increased in a host by increasing the copy number thereof or by ligating it to a potent promoter. The copy number can be increased by introducing a plasmid containing the threonine operon into a host. The copy number can also be increased by transferring the threonine operon to the genome of a host using a transposon, Mu-phage, or the like.

Examples of methods for imparting or enhancing L-threonine-producing ability also can include, for example, a method of imparting L-threonine resistance to a host, and a method of imparting L-homoserine resistance to a host. Such resistance can be imparted by, for example, enhancing the expression of a gene that imparts L-threonine resistance or a gene that imparts L-homoserine resistance. Examples of the genes that impart the above-mentioned resistance can include the rhtA gene (Res. Microbiol. 154:123-135 (2003)), rhtB gene (EP0994190A), rhtC gene (EP1013765A), yfiK gene, and yeaS gene (EP1016710A). Methods for imparting L-threonine resistance to a host include the methods described in EP0994190A and WO90/04636.

Specific examples of L-threonine-producing bacteria and parental strains that can be used to derive them can include, for example, *E. coli* TDH-6/pVIC40 (VKPM B-3996, U.S. Pat. Nos. 5,175,107 and 5,705,371), *E. coli* 472T23/pYN7 (ATCC 98081, U.S. Pat. No. 5,631,157), *E. coli* NRRL-21593 (U.S. Pat. No. 5,939,307), *E. coli* FERM BP-3756

(U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP1149911A), and *E. coli* VKPM B-5318 (EP0593792B).

The VKPM B-3996 strain can be obtained by introducing the plasmid pVIC40 into the TDH-6 strain. The TDH-6 strain has sucrose-assimilating ability and is deficient in the thrC gene, and the ilvA gene thereof has a leaky mutation. The TDH-6 strain also has a mutation in the rhtA gene, which imparts resistance to high concentration of threonine or homoserine. The plasmid pVIC40 can be obtained by inserting the thrA*BC operon containing a mutant thrA gene encoding an aspartokinase-homoserine dehydrogenase I resistant to feedback inhibition by threonine and the wild-type thrBC genes into an RSF1010-derived vector (U.S. Pat. No. 5,705,371). This mutant thrA gene encodes an aspartokinase-homoserine dehydrogenase I which is substantially desensitized to feedback inhibition by threonine. The B-3996 strain was deposited on Nov. 19, 1987 at the All-Union Scientific Center of Antibiotics (Nagatinskaya Street 3-A, 117105 Moscow, Russia) under the accession number RIA 1867. This strain was also deposited at the Russian National Collection of Industrial Microorganisms (VKPM, FGUP GosNII Genetika, 1 Dorozhny proezd., 1 Moscow 117545, Russia) on Apr. 7, 1987 under the accession number VKPM B-3996.

The VKPM B-5318 strain is prototrophic with regard to isoleucine, and harbors the plasmid pPRT614, which corresponds to the plasmid pVIC40 of which the regulatory region of the threonine operon is replaced with the temperature-sensitive λ-phage Cl repressor and PR promoter. The VKPM B-5318 strain was deposited at the Russian National Collection of Industrial Microorganisms (VKPM, FGUP GosNII Genetika, 1 Dorozhny proezd., 1 Moscow 117545, Russia) on May 3, 1990 under the accession number of VKPM B-5318.

The thrA gene which encodes aspartokinase-homoserine dehydrogenase I of *E. coli* has been elucidated (nucleotide numbers 337 to 2799, GenBank accession NC 000913.2, gi: 49175990). The thrA gene is located between the thrL and thrB genes on the chromosome of *E. coli* K-12. The thrB gene which encodes homoserine kinase of *Escherichia coli* has been elucidated (nucleotide numbers 2801 to 3733, GenBank accession $NC_{13}$ 000913.2, gi: 49175990). The thrB gene is located between the thrA and thrC genes on the chromosome of *E. coli* K-12. The thrC gene which encodes threonine synthase of *E. coli* has been elucidated (nucleotide numbers 3734 to 5020, GenBank accession $NC_{13}$ 000913.2, gi: 49175990). The thrC gene is located between the thrB gene and the yaaX open reading frame on the chromosome of *E. coli* K-12. The thrA*BC operon containing a mutant thrA gene which encodes an aspartokinase-homoserine dehydrogenase I resistant to feedback inhibition by threonine and the wild-type thrBC genes can be obtained from the well-known plasmid pVIC40, which is present in the threonine-producing *E. coli* strain VKPM B-3996 (U.S. Pat. No. 5,705,371).

The rhtA gene of *E. coli* is located at 18 min on the *E. coli* chromosome close to the glnHPQ operon, which encodes components of the glutamine transport system. The rhtA gene is identical to ORF1 (ybiF gene, nucleotide numbers 764 to 1651, GenBank accession number AAA218541, gi:440181) and is located between the pexB and ompX genes. The unit expressing a protein encoded by the ORF1 has been designated rhtA gene (rht: resistance to homoserine and threonine). It has also been revealed that the rhtA23 mutation that imparts resistance to high concentration of threonine or homoserine is an A-for-G substitution at position-1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457; EP1013765A).

The asd gene of *E. coli* has been elucidated (nucleotide numbers 3572511 to 3571408, GenBank accession NC_000913.1, gi:16131307), and can be obtained by PCR (White, T. J., et al., Trends Genet, 5:185-189, 1989) utilizing primers prepared on the basis of the nucleotide sequence of the gene. The asd genes of other microorganisms can also be obtained in a similar manner.

The aspC gene of *E. coli* has also been elucidated (nucleotide numbers 983742 to 984932, GenBank accession NC_000913.1, gi:16128895), and can be obtained by PCR utilizing primers prepared on the basis of the nucleotide sequence of the gene. The aspC genes of other microorganisms can also be obtained in a similar manner.

Furthermore, examples of coryneform bacteria having L-threonine-producing ability can include, for example, *Corynebacterium acetoacidophilum* AJ12318 (FERM BP-1172, U.S. Pat. No. 5,188,949).

<L-Lysine-Producing Bacteria>

Examples of methods for imparting or enhancing L-lysine-producing ability can include, for example, a method of modifying a bacterium so that the bacterium has an increased activity or activities of one or more of the L-lysine biosynthesis enzymes. Examples of such enzymes can include, but are not particularly limited to, dihydrodipicolinate synthase (dapA), aspartokinase III (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenase (asd), aspartate aminotransferase (aspartate transaminase) (aspC), diaminopimelate epimerase (dapF), tetrahydrodipicolinate succinylase (dapD), succinyl diaminopimelate deacylase (dapE), and aspartase (aspA) (EP1253195A). It is preferable to enhance the activity or activities of one or more of, for example, dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, and succinyl diaminopimelate deacylase. Furthermore, L-lysine-producing bacteria and parental strains that can be used to derive them can express an increased level of the gene involved in energy efficiency (cyo) (EP1170376A), the gene encoding nicotinamide nucleotide transhydrogenase (pntAB) (U.S. Pat. No. 5,830, 716), the ybjE gene (WO2005/073390), or combinations of these. Since aspartokinase III (lysC) is subject to feedback inhibition by L-lysine, a mutant lysC gene encoding an aspartokinase III desensitized to feedback inhibition by L-lysine (U.S. Pat. No. 5,932,453) may be used for enhancing the activity of this enzyme. Examples of the aspartokinase III desensitized to feedback inhibition by L-lysine can include aspartokinase III derived from *Escherichia coli* and having one or more of the following mutations: replacing the methionine residue at position 318 with an isoleucine residue; replacing the glycine residue at position 323 with an aspartic acid residue; and replacing the threonine residue at position 352 with an isoleucine residue (U.S. Pat. Nos. 5,661,012 and 6,040,160). Furthermore, since dihydrodipicolinate synthase (dapA) is subject to feedback inhibition by L-lysine, a mutant dapA gene encoding a dihydrodipicolinate synthase desensitized to feedback inhibition by L-lysine may be used for enhancing the activity of this enzyme. Examples of the dihydrodipicolinate synthase desensitized to feedback inhibition by L-lysine can include dihydrodipicolinate synthase derived from *Escherichia coli* and wherein the histidine residue at position 118 is replaced with a tyrosine residue (U.S. Pat. No. 6,040,160).

Examples of methods for imparting or enhancing L-lysine-producing ability also can include, for example, a method of modifying a bacterium so that the bacterium has a reduced activity or activities of one or more of the enzymes that catalyze a reaction branching away from the biosynthetic pathway of L-lysine to generate a compound other than L-lysine. Examples of such enzymes can include, but are not particularly limited to, homoserine dehydrogenase, lysine decarboxylase (U.S. Pat. No. 5,827,698), and malic enzyme (WO2005/010175).

Furthermore, examples of methods for imparting or enhancing L-lysine-producing ability to or in coryneform bacteria also can include a method of modifying the bacteria so that the activity of a lysine excretion system (lysE) is increased (WO97/23597). The lysE gene of *Corynebacterium glutamicum* ATCC 13032 corresponds to a sequence complementary to the sequence of the nucleotide numbers 1,329,712 to 1,330,413 in the genome sequence registered as Genbank Accession No. NC_006958 (VERSION NC_006958.1 GI:62388892) in the NCBI database. The LysE protein of *Corynebacterium glutamicum* ATCC 13032 is registered as GenBank accession No. YP_225551 (YP_225551.1 GI:62390149).

Examples of L-lysine-producing bacteria and parental strains that can be used to derive them also can include mutant strains having resistance to an L-lysine analogue. L-Lysine analogues can inhibit the growth of bacteria such as bacteria of the family Enterobacteriaceae and coryneform bacteria, but this inhibition is fully or partially released when L-lysine is present in the medium. Examples of these L-lysine analogues can include, but are not particularly limited to, oxalysine, lysine hydroxamate, S-(2-aminoethyl)-L-cysteine (AEC), γ-methyllysine. and α-chlorocaprolactam. Mutant strains having resistance to these lysine analogues can be obtained by subjecting a bacterium to a conventional artificial mutagenesis treatment.

Specific examples of L-lysine-producing bacteria and parental strains that can be used to derive them can include *E. coli* AJ11442 (FERM BP-1543, NRRL B-12185, U.S. Pat. No. 4,346,170) and *E. coli* VL611. In these strains, aspartokinase is desensitized to feedback inhibition by L-lysine.

Specific examples of L-lysine-producing bacteria and parental strains that can be used to derive them also can include the *E. coli* WC196 strain. The WC196 strain was bred by imparting AEC resistance to the W3110 strain, which was derived from *E. coli* K-12 (U.S. Pat. No. 5,827,698). The WC196 strain was designated *E. coli* AJ13069 and deposited at the National Institute of Bioscience and Human-Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Dec. 6, 1994 and assigned an accession number of FERM P-14690. Then, the deposit was converted to an international deposit under the provisions of the Budapest Treaty on Sep. 29, 1995, and assigned an accession number of FERM BP-5252 (U.S. Pat. No. 5,827,698).

Examples of L-lysine-producing bacteria can include *E. coli* WC196ΔcadAΔldc and *E. coli* WC196ΔcadAΔldc/pCABD2 (WO2010/061890). The *E. coli* WC196ΔcadAΔldc is a strain constructed from the WC196 strain by disrupting the cadA and ldcC genes encoding lysine decarboxylase. The WC196ΔcadAΔldc/pCABD2 strain was constructed by introducing the plasmid pCABD2 containing the lysine biosynthesis enzyme genes (U.S. Pat. No. 6,040,160) into the WC196ΔcadAΔldc strain. The WC196ΔcadAΔldc strain, designated as AJ110692, was deposited at the independent administrative agency, National Institute of Advanced Industrial Science and Technology, International Patent Organism Depositary (currently, independent administrative agency, National Institute of Technology and Evaluation, International Patent Organism Depositary, #120, 2-5-8 Kazusakamatari, Kisarazu-shi, Chiba-ken, 292-0818, Japan) on Oct. 7, 2008 as an international deposit, and assigned an accession number of FERM BP-11027. The plasmid pCABD2 contains a mutant dapA gene derived from *Escherichia coli* and encoding a dihydrodipicolinate synthase (DDPS) having a mutation causing desensitization to feedback inhibition by L-lysine (H118Y), a mutant lysC gene derived from *Escherichia coli* and encoding aspartokinase III having a mutation causing desensitization to feedback inhibition by L-lysine (T352I), the dapB gene derived from *Escherichia coli* and encoding dihydrodipicolinate reductase, and the ddh gene derived from *Brevibacterium lactofermentum* and encoding diaminopimelate dehydrogenase.

Examples of L-lysine-producing bacteria also can include *E. coli* AJIK01 (NITE BP-01520). The AJIK01 strain was designated *E. coli* AJ111046, and deposited at the independent administrative agency, National Institute of Technology and Evaluation, International Patent Organism Depositary (#122, 2-5-8 Kazusakamatari, Kisarazu-shi, Chiba-ken, 292-0818, Japan) on Jan. 29, 2013. Then, it was converted to an international deposit under the provisions of the Budapest Treaty on May 15, 2014, and assigned an accession number of NITE BP-01520.

Examples of coryneform bacteria having L-lysine-producing ability can include, for example, the AEC-resistant mutant strains (*Corynebacterium glutamicum* (*Brevibacterium lactofermentum* AJ11082) (NRRL B-11470) strain etc., Japanese Patent Publication (Kokoku) Nos. 56-1914, 56-1915, 57-14157, 57-14158, 57-30474, 58-10075, 59-4993, 61-35840, 62-24074, 62-36673, 5-11958, 7-112437, and 7-112438); mutant strains requiring an amino acid such as L-homoserine for their growth (Japanese Patent Publication Nos. 48-28078 and 56-6499); mutant strains showing resistance to AEC and further requiring an amino acid such as L-leucine, L-homoserine, L-proline, L-serine, L-arginine, L-alanine, and L-valine (U.S. Pat. Nos. 3,708,395 and 3,825,472); mutant strains showing resistance to DL-α-amino-ε-caprolactam, α-amino-lauryllactam, aspartic acid analogue, sulfa drug, quinoid, and N-lauroylleucine; mutant strains showing resistance to an oxaloacetate decarboxylase inhibitor or a respiratory chain enzyme inhibitor (Japanese Patent Laid-open (Kokai) Nos. 50-53588, 50-31093, 52-102498, 53-9394, 53-86089, 55-9783, 55-9759, 56-32995, 56-39778, Japanese Patent Publication Nos. 53-43591 and 53-1833); mutant strains requiring inositol or acetic acid (Japanese Patent Laid-open (Kokai) Nos. 55-9784 and 56-8692); mutant strains that are susceptible to fluoropyruvic acid or a temperature of 34° C. or higher (Japanese Patent Laid-open (Kokai) Nos. 55-9783 and 53-86090); and mutant strains showing resistance to ethylene glycol (U.S. Pat. No. 4,411,997).

<L-Arginine-Producing Bacteria>

Examples of methods for imparting or enhancing L-arginine-producing ability can include, for example, a method of modifying a bacterium so that the bacterium has an increased activity or activities of one or more of the L-arginine biosynthesis enzymes. Examples of such enzymes can include, but are not particularly limited to, N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyl transferase (argF, argI), argininosuccinate synthetase (argG), argininosuccinate lyase (argH), ornithine acetyl transferase (argJ), and carbamoyl phosphate synthetase (carAB). As the N-acetylglutamate synthase gene (argA), for example, a gene encoding a mutant N-acetylglutamate synthase desensitized to feedback inhibition by L-arginine by substitution for the amino acid residues corresponding to the positions 15 to 19 of the wild type enzyme (EP1170361A) can be used.

Specific examples of L-arginine-producing bacteria and parental strains that can be used to derive them can include, for example, the *E. coli* 237 strain (VKPM B-7925, US2002/058315A1), derivative strains thereof introduced with the argA gene encoding a mutant N-acetyl glutamate synthase (Russian Patent Application No. 2001112869, EP1170361A1), *E. coli* 382 strain derived from the 237 strain and having an improved acetic acid-assimilating ability (VKPM B-7926, EP1170358A1), and *E. coli* 382ilvA+ strain, which is a strain obtained from the 382 strain by introducing the wild-type ilvA gene from *E. coli* K-12 strain thereto. The *E. coli* strain 237 was deposited at the Russian National Collection of Industrial Microorganisms (VKPM, FGUP GosNII Genetika, 1 Dorozhny proezd., 1 Moscow 117545, Russia) on Apr. 10, 2000 under an accession number of VKPM B-7925, and the deposit was converted to an international deposit under the provisions of Budapest Treaty on May 18, 2001. The *E. coli* 382 strain was deposited at the Russian National Collection of Industrial Microorganisms (VKPM, FGUP GosNII Genetika, 1 Dorozhny proezd., 1 Moscow 117545, Russia) on Apr. 10, 2000 under accession number of VKPM B-7926.

Examples of L-arginine-producing bacteria and parental strains that can be used to derive them also can include strains having resistance to amino acid analogues, and so forth. Examples of such strains can include *E. coli* mutant strains having resistance to α-methylmethionine, p-fluorophenylalanine, D-arginine, arginine hydroxamate, S-(2-aminoethyl)-cysteine, α-methylserine, β-2-thienylalanine, or sulfaguanidine (Japanese Patent Laid-open (Kokai) No. 56-106598).

Examples of L-arginine-producing bacteria and parent strains that can be used to derive them also can include such coryneform bacteria as a strain deficient in ArgR, which is an arginine repressor (US2002-0045223A), and a strain in which glutamine synthetase activity is increased (US2005-0014236A).

Examples of L-arginine-producing bacteria and parent strains that can be used to derive them also can include mutant strains of coryneform bacteria, the mutant strains having resistance to an amino acid analogue or the like. Examples of such strains can include, for example, strains having resistance to 2-thiazolealanine and further exhibiting auxotrophy for L-histidine, L-proline, L-threonine, L-isoleucine, L-methionine, or L-tryptophan (Japanese Patent Laid-open (Kokai) No. 54-44096); strains resistant to ketomalonic acid, fluoromalonic acid, or monofluoroacetic acid (Japanese Patent Laid-open (Kokai) No. 57-18989); strains resistant to argininol (Japanese Patent Publication No. 62-24075); strains resistant to X-guanidine (X represents an aliphatic chain or a derivative thereof, Japanese Patent Laid-open (Kokai) No. 2-186995); and strains resistant to arginine hydroxamate and 6-azauracil (Japanese Patent Laid-open (Kokai) No. 57-150381). Specific examples of coryneform bacteria having L-arginine-producing ability can include the following strains:

*Corynebacterium glutamicum* (*Brevibacterium flavum*) AJ11169 (FERM BP-6892)

*Corynebacterium glutamicum* (*Brevibacterium lactofermentum*) AJ12092 (FERM BP-6906)

*Corynebacterium glutamicum* (*Brevibacterium flavum*) AJ11336 (FERM BP-6893)

*Corynebacterium glutamicum* (*Brevibacterium flavum*) AJ11345 (FERM BP-6894)

*Corynebacterium glutamicum* (*Brevibacterium lactofermentum*) AJ12430 (FERM BP-2228)

<L-Citrulline-Producing Bacteria and L-Ornithine-Producing Bacteria>

L-citrulline and L-ornithine are intermediates of the biosynthetic pathway of L-arginine. Hence, examples of methods for imparting or enhancing an ability to produce L-citrulline and/or L-ornithine can include, for example, a method of modifying a bacterium so that the bacterium has an increased activity or activities of one or more of the L-arginine biosynthesis enzymes. Examples of such enzymes can include, but are not particularly limited to, N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyl transferase (argF, argI), ornithine acetyl transferase (argJ), and carbamoyl phosphate synthetase (carAB), for L-citrulline. Furthermore, Examples of such enzymes can include, but not particularly limited to, N-acetylglutamate synthase (argA), N-acetylglutamate kinase (argB), N-acetylglutamyl phosphate reductase (argC), acetylornithine transaminase (argD), acetylornithine deacetylase (argE), and ornithine acetyl transferase (argJ), for L-ornithine.

An L-citrulline-producing bacterium can be easily obtained from, for example, an L-arginine bacterium such as the *E. coli* 382 strain (VKPM B-7926) by decreasing the activity of argininosuccinate synthetase encoded by argG gene. Also, an L-ornithine-producing bacterium can be easily obtained from, for example, an L-arginine bacterium such as the *E. coli* 382 strain (VKPM B-7926) by decreasing the activity of ornithine carbamoyl transferase encoded by argF and argI genes.

Specific examples of L-citrulline-producing bacteria and parental strains that can be used to derive them can include, for example, strains belonging to the genus *Escherichia*, such as the *E. coli* strains 237/pMADS11, 237/pMADS12, and 237/pMADS13, which have a mutant N-acetylglutamate synthase (Russian patent No. 2,215,783, U.S. Pat. No. 6,790,647, and EP1170361B1), *E. coli* strains 333 (VKPM B-8084) and 374 (VKPM B-8086), which have carbamoyl phosphate synthetase resistant to feedback inhibition (Russian patent No. 2,264,459), *E. coli* strains having an increased activity of α-ketoglutarate synthase and having a modified activity of ferredoxin NADP$^+$ reductase, pyruvate synthase, and/or α-ketoglutarate dehydrogenase (EP2133417A); and the *P. ananatis* NA1sucAsdhA strain, which has a reduced activity of succinate dehydrogenase and α-ketoglutarate dehydrogenase (US2009-286290A1).

<L-Histidine-Producing Bacteria>

Examples of methods for imparting or enhancing L-histidine-producing ability can include, for example, a method of modifying a bacterium so that the bacterium has an increased activity or activities of one or more of the L-histidine biosynthesis enzymes. Examples of such enzymes can include, but are not particularly limited to, ATP phosphoribosyltransferase (hisG), phosphoribosyl AMP cyclohydrolase (hisI), phosphoribosyl-ATP pyrophosphohydrolase (hisI), phosphoribosylformimino-5-aminoimidazole carboxamide ribotide isomerase (hisA), amidotransferase (hisH), histidinol phosphate aminotransferase (hisC), histidinol phosphatase (hisB), and histidinol dehydrogenase (hisD).

Among these enzymes, the L-histidine biosynthesis enzymes encoded by hisG and hisBHAFI are known to be inhibited by L-histidine. Therefore, the ability to produce L-histidine can be imparted or enhanced by, for example, introducing a mutation for conferring resistance to feedback inhibition into the gene encoding ATP phosphoribosyltransferase (hisG) (Russian Patent Nos. 2,003,677 and 2,119,536).

Specific examples of L-histidine-producing bacteria and parental strains that can be used to derive them can include, for example, strains belonging to the genus *Escherichia*, such as the *E. coli* 24 strain (VKPM B-5945, RU2003677), *E. coli* NRRL B-12116 to B-12121 (U.S. Pat. No. 4,388,405), *E. coli* H-9342 (FERM BP-6675) and H-9343 (FERM BP-6676, U.S. Pat. No. 6,344,347), *E. coli* H-9341 (FERM BP-6674, EP1085087), *E. coli* AI80/pFM201 (U.S. Pat. No. 6,258,554), *E. coli* FERM P-5038 and FERM P-5048, which have been introduced with a vector carrying a DNA encoding an L-histidine-biosynthesis enzyme (Japanese Patent Laid-open (Kokai) No. 56-005099), *E. coli* strains introduced with a gene for amino acid transport (EP1016710A), and *E. coli* 80 strain, which has been imparted with resistance to sulfaguanidine, DL-1,2,4-triazole-3-alanine, and streptomycin (VKPM B-7270, Russian Patent No. 2119536).

<L-Cysteine-Producing Bacteria>

Examples of methods for imparting or enhancing L-cysteine-producing ability can include, for example, a method of modifying a bacterium so that the bacterium has an increased activity or activities of one or more of the L-cysteine biosynthesis enzymes. Examples of such enzymes can include, but are not particularly limited to, serine acetyltransferase (cysE) and 3-phosphoglycerate dehydrogenase (serA). The serine acetyltransferase activity can be enhanced by, for example, introducing a mutant cysE gene encoding a mutant serine acetyltransferase resistant to feedback inhibition by cysteine into a bacterium. Such a mutant serine acetyltransferase is disclosed in, for example, Japanese Patent Laid-open (Kokai) No. 11-155571 and US2005-0112731A. Furthermore, the 3-phosphoglycerate dehydrogenase activity can be enhanced by, for example, introducing a mutant serA gene encoding a mutant 3-phosphoglycerate dehydrogenase resistant to feedback inhibition by serine into a bacterium. Such a mutant 3-phosphoglycerate dehydrogenase is disclosed in, for example, U.S. Pat. No. 6,180,373.

Furthermore, examples of methods for imparting or enhancing L-cysteine-producing ability also can include, for example, a method of modifying a bacterium so that the bacterium has a reduced activity or activities of one or more of the enzymes that catalyze a reaction branching away from the biosynthesis pathway of L-cysteine to generate a compound other than L-cysteine. Examples of such enzymes can include, for example, enzymes involved in decomposition of L-cysteine. Examples of the enzymes involved in decomposition of L-cysteine can include, but are not particularly limited to, cystathionine-β-lyase (metC, Japanese Patent Laid-open (Kokai) No. 11-155571; Chandra et al., Biochemistry, 21 (1982) 3064-3069), tryptophanase (tnaA, Japanese Patent Laid-open (Kokai) No. 2003-169668; Austin Newton et al., J. Biol. Chem., 240 (1965) 1211-1218), 0-acetylserine sulfhydrylase B (cysM, Japanese Patent Laid-open (Kokai) No. 2005-245311), the malY gene product (Japanese Patent Laid-open (Kokai) No. 2005-245311), the d0191 gene product of *Pantoea ananatis* (Japanese Patent Laid-open (Kokai) No. 2009-232844), and cysteine desulfhydrase (aecD, Japanese Patent Laid-open (Kokai) No. 2002-233384.

Furthermore, examples of methods for imparting or enhancing L-cysteine-producing ability also can include, for example, a method of enhancing the L-cysteine excretory system, and a method of enhancing the sulfate/thiosulfate transport system. Examples of proteins of the L-cysteine excretory system can include the protein encoded by the ydeD gene (Japanese Patent Laid-open (Kokai) No. 2002-233384), the protein encoded by the yfiK gene (Japanese Patent Laid-open (Kokai) No. 2004-49237), the proteins encoded by the emrAB, emrKY, yojIH, acrEF, bcr, and cusA genes (Japanese Patent Laid-open (Kokai) No. 2005-287333), and the protein encoded by the yeaS gene (Japanese Patent Laid-open (Kokai) No. 2010-187552). Examples of the proteins of the sulfate/thiosulfate transport system can include the proteins encoded by the cysPTWAM gene cluster.

Specific examples of L-cysteine-producing bacteria and parental strains that can be used to derive them can include, for example, *E. coli* JM15 transformed with different cysE alleles encoding feedback-resistant serine acetyltransferases (U.S. Pat. No. 6,218,168, Russian patent application 2003121601), *E. coli* W3110 having an over-expressed gene encoding a protein suitable for secretion of a cytotoxic substance (U.S. Pat. No. 5,972,663), *E. coli* strains having a reduced cysteine desulfohydrase activity (Japanese Patent Laid-open (Kokai) No. 11-155571), and *E. coli* W3110 having an increased activity of a positive transcriptional regulator for cysteine regulon encoded by the cysB gene (WO01/27307A1).

Furthermore, examples of coryneform bacteria having L-cysteine-producing ability can include coryneform bacteria having serine acetyltransferase desensitized to feedback inhibition by L-cysteine thereby to show enhanced intracellular serine acetyltransferase activity (Japanese Patent Laid-open (Kokai) No. 2002-233384).

<L-Serine-Producing Bacteria>

Examples of methods for imparting or enhancing L-serine-producing ability can include, for example, a method of modifying a bacterium so that the bacterium has an increased activity or activities of one or more of the L-serine biosynthesis enzymes. Examples of such enzymes can include, but are not particularly limited to, 3-phosphoglycerate dehydrogenase (serA), phosphoserine transaminase (serf), and phosphoserine phosphatase (serB) (Japanese Patent Laid-open (Kokai) No. 11-253187). 3-phosphoglycerate dehydrogenase activity can be increased by, for example, introducing a mutant serA gene encoding a mutant 3-phosphoglycerate dehydrogenase resistant to feedback inhibition by L-serine into a bacterium. The mutant 3-phosphoglycerate dehydrogenase is disclosed in, for example, U.S. Pat. No. 6,180,373.

Examples of L-serine-producing bacteria and parental strains that can be used to derive them can include, for example, coryneform bacteria resistant to azaserine or β-(2- thienyl)-DL-alanine and deficient in L-serine decomposition ability (Japanese Patent Laid-open (Kokai) No. 10-248588). Specific examples of such coryneform bacteria can include, for example, *Corynebacterium glutamicum* (*Brevibacterium flavum*) AJ13324 (FERM P-16128), which is resistant to azaserine and deficient in L-serine decomposition ability, and *Corynebacterium glutamicum* (*Brevibacterium flavum*) AJ13325 (FERM P-16129), which is resistant to β-(2-thienyl)-DL-alanine and deficient in L-serine decomposition ability (Japanese Patent Laid-open (Kokai) No. 10-248588).

<L-Methionine-Producing Bacteria>

Examples of L-methionine-producing bacteria and parental strains that can be used to derive them can include L-threonine auxotrophic strains and mutant strains resistant to norleucine (Japanese Patent Laid-open (Kokai) No. 2000-139471). Examples of L-methionine-producing bacteria and parental strains that can be used to derive them also can include a strain containing a mutant homoserine transsuccinylase resistant to feedback inhibition by L-methionine (Japanese Patent Laid-open (Kokai) No. 2000-139471, US2009-0029424A). Since L-methionine is biosynthesized via L-cysteine as an intermediate, L-methionine-producing ability can also be improved by improving L-cysteine-producing ability (Japanese Patent Laid-open (Kokai) No. 2000-139471, US2008-0311632A).

Specific examples of L-methionine-producing bacteria and parental strains that can be used to derive them can include, for example, *E. coli* AJ11539 (NRRL B-12399), *E. coli* AJ11540 (NRRL B-12400), *E. coli* AJ11541 (NRRL B-12401), *E. coli* AJ11542 (NRRL B-12402, British Patent No. 2075055), the *E. coli* 218 strain (VKPM B-8125, Russian Patent No. 2209248) and the 73 strain (VKPM B-8126, Russian Patent No. 2215782), which are resistant to norleucine, which is an analogue of L-methionine, and *E. coli* AJ13425 (FERMP-16808, Japanese Patent Laid-open (Kokai) No. 2000-139471). The AJ13425 strain is an L-threonine auxotrophic strain derived from the *E. coli* W3110, in which the methionine repressor is deleted, the intracellular S-adenosylmethionine synthetase activity is attenuated, and the intracellular homoserine transsuccinylase activity, cystathionine γ-synthase activity, and aspartokinase-homoserine dehydrogenase II activity are enhanced.

<L-Leucine-Producing Bacteria>

Examples of methods for imparting or enhancing L-leucine-producing ability can include, for example, a method of modifying a bacterium so that the bacterium has an increased activity or activities of one or more of the L-leucine biosynthesis enzymes. Examples of such enzymes can include, but are not particularly limited to, the enzymes encoded by the genes of the leuABCD operon. Furthermore, for enhancing the activity of such an enzyme, for example, the mutant leuA gene encoding an isopropyl maleate synthase desensitized to feedback inhibition by L-leucine (U.S. Pat. No. 6,403,342) can be used.

Specific examples of L-leucine-producing bacteria and parental strains that can be used to derive them can include, for example, strains belonging to the genus *Escherichia*, such as *E. coli* strains resistant to leucine (for example, the 57 strain (VKPM B-7386, U.S. Pat. No. 6,124,121)), *E. coli* strains resistant to an leucine analogue such as β-2-thienylalanine, 3-hydroxyleucine, 4-azaleucine, and 5,5,5-trifluoroleucine (Japanese Patent Publication (Kokoku) No. 62-34397 and Japanese Patent Laid-open (Kokai) No. 8-70879), *E. coli* strains obtained by a gene engineering technique described in WO96/06926, and *E. coli* H-9068 (Japanese Patent Laid-open (Kokai) No. 8-70879).

Examples of coryneform bacteria having L-leucine-producing ability can include, for example, *Corynebacterium glutamicum* (*Brevibacterium lactofermentum*) AJ3718 (FERM P-2516), which is resistant to 2-thiazole alanine and β-hydroxyleucine and auxotrophic for isoleucine and methionine.

<L-Isoleucine-Producing Bacteria>

Examples of methods for imparting or enhancing L-isoleucine-producing ability can include, for example, a method of modifying a bacterium so that the bacterium has increased activity or activities of one or more of the L-isoleucine biosynthesis enzymes. Examples of such enzymes can include, but are not particularly limited to, threonine deaminase and acetohydroxy acid synthase (Japanese Patent Laid-open (Kokai) No. 2-458, EP0356739A, U.S. Pat. No. 5,998,178).

Specific examples of L-isoleucine-producing bacteria and parental strains that can be used to derive them can include, for example, *Escherichia* bacteria such as mutant strains having resistance to 6-dimethylaminopurine (Japanese Patent Laid-open (Kokai) No. 5-304969), mutant strains having resistance to an isoleucine analogue such as thiaisoleucine and isoleucine hydroxamate, and mutant strains having resistance to such an isoleucine analogue and further having resistance to DL-ethionine and/or arginine hydroxamate (Japanese Patent Laid-open (Kokai) No. 5-130882).

Examples of coryneform bacteria having L-isoleucine-producing ability can include, for example, the coryneform bacterium in which brnE gene encoding a branched chain amino acid excretion protein is amplified (Japanese Patent Laid-open (Kokai) No. 2001-169788), the coryneform bacterium to which L-isoleucine-producing ability is imparted by protoplast fusion with an L-lysine-producing bacterium (Japanese Patent Laid-open (Kokai) No. 62-74293), the coryneform bacterium in which homoserine dehydrogenase is enhanced (Japanese Patent Laid-open (Kokai) No. 62-91193), the threonine hydroxamate resistant strain (Japanese Patent Laid-open (Kokai) No 62-195293), the α-ketomalonic acid resistant strain (Japanese Patent Laid-open (Kokai) No. 61-15695), the methyllysine resistant strain (Japanese Patent Laid-open (Kokai) No. 61-15696), and *Corynebacterium glutamicum* (*Brevibacterium flavum*) AJ12149 (FERM BP-759, U.S. Pat. No. 4,656,135).

<L-Valine-Producing Bacteria>

Examples of methods for imparting or enhancing L-valine-producing ability can include, for example, a method of modifying a bacterium so that the bacterium has an increased activity or activities of one or more of the L-valine biosynthesis enzymes. Examples of such enzymes can include, but are not particularly limited to, the enzymes encoded by the genes of the ilvGMEDA operon and the enzymes encoded by the ilvBNC operon. The ilvBN gene encodes acetohydroxy acid synthase, and the iivC gene encodes isomeroreductase (WO00/50624). Expression of the ilvGMEDA operon and the ilvBNC operon are suppressed (attenuated) by L-valine, L-isoleucine, and/or L-leucine. Therefore, when enhancing the activity of such an enzyme, the suppression of expression by the produced L-valine can be reversed by removing or modifying a region required for the attenuation. Furthermore, the threonine deaminase encoded by the ilvA gene is an enzyme that catalyzes the deamination reaction of L-threonine resulting 2-ketobutyric acid, which is the rate-limiting step of the L-isoleucine biosynthesis system. Therefore, when producing L-valine, the ilvA gene can be, for example, disrupted, and thereby the threonine deaminase activity is decreased.

Examples of methods for imparting or enhancing L-valine-producing ability also can include, for example, a method of modifying a bacterium so that the bacterium has a reduced activity or activities of one or more of the enzymes that catalyze a reaction branching away from the biosynthesis pathway of L-valine to generate a compound other than L-valine. Examples of such enzymes can include, but are not particularly limited to, threonine dehydratase involved in the L-leucine synthesis, and the enzymes involved in the D-pantothenic acid synthesis (WO00/50624).

Specific examples of L-valine-producing bacteria and parental strains that can be used to derive them can include, for example, E. coli strains modified so as to overexpress the ilvGMEDA operon (U.S. Pat. No. 5,998,178).

Examples of L-valine-producing bacteria and parental strains that can be used to derive them also can include mutant strains having a mutation in amino-acyl t-RNA synthetase (U.S. Pat. No. 5,658,766). Examples of such strains can include, for example, E. coli VL1970, which has a mutation in the ileS gene encoding isoleucine t-RNA synthetase. E. coli VL1970 was deposited at the Russian National Collection of Industrial Microorganisms (VKPM, FGUP GosNII Genetika, 1 Dorozhny Proezd, 1 Moscow 117545, Russia) on Jun. 24, 1988 under the accession number of VKPM B-4411. Examples of L-valine-producing bacteria and parental strains that can be used to derive them also can include mutant strains requiring lipoic acid for growth and/or lacking $H^+$-ATPase (WO96/06926).

Examples of L-valine-producing bacteria and parent strains that can be used to derive them also can include strains resistant to an amino acid analogue or the like. Examples of such strains can include, for example, the coryneform bacterium strains which are auxotrophic for L-isoleucine and L-methionine, and resistant to D-ribose, purine ribonucleoside, or pyrimidine ribonucleoside, and have an ability to produce L-valine (FERM P-1841, FERM P-29) (Japanese Patent Publication No. 53-025034), coryneform bacterium strains resistant to polyketides (FERM P-1763, FERM P-1764) (Japanese Patent Publication No. 06-065314), and coryneform bacterium strains resistant to L-valine in a medium containing acetic acid as the sole carbon source and sensitive to pyruvic acid analogues (fluoropyruvic acid etc.) in a medium containing glucose as the sole carbon source (FERM BP-3006, BP-3007) (Japanese Patent No. 3006929).

<L-Alanine-Producing Bacteria>

Examples of L-alanine-producing bacteria and parent strains that can be used to derive them can include the coryneform bacteria deficient in the $H^+$-ATPase (Appl. Microbiol. Biotechnol., 2001 November, 57(4):534-40) and coryneform bacteria in which the aspartate β-decarboxylase activity is enhanced (Japanese Patent Laid-open (Kokai) No. 07-163383).

<L-Tryptophan-Producing Bacteria, L-Phenylalanine-Producing Bacteria, and L-Tyrosine-Producing Bacteria>

Examples of methods for imparting or enhancing L-tryptophan-producing ability, L-phenylalanine-producing ability, and/or L-tyrosine-producing ability can include, for example, a method of modifying a bacterium so that the bacterium has an increased activity or activities of one or more of the L-tryptophan, L-phenylalanine, and/or L-tyrosine biosynthesis enzymes.

Examples of enzymes common to the biosynthesis systems of these aromatic amino acids can include, but are not particularly limited to, 3-deoxy-D-arabinoheptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), and chorismate synthase (aroC) (EP763127B). The expressions of the genes encoding these enzymes are controlled by the tyrosine repressor (tyrR), and the activities of these enzymes may be enhanced by deleting the tyrR gene (EP763127B).

Examples of the L-tryptophan biosynthesis enzymes can include, but are not particularly limited to, anthranilate synthase (trpE), tryptophan synthase (trpAB), and phosphoglycerate dehydrogenase (serA). For example, by introducing a DNA containing the tryptophan operon, L-tryptophan-producing ability can be imparted or enhanced. Tryptophan synthase consists of α and β subunits encoded by the trpA and trpB genes, respectively. Since the anthranilate synthase is subject to feedback inhibition by L-tryptophan, a gene encoding this enzyme that has had a mutation introduced that causes desensitization to feedback inhibition may be used for enhancing the activity of that enzyme. Since the phosphoglycerate dehydrogenase is subject to feedback inhibition by L-serine, a gene encoding this enzyme having a mutation that causes desensitization to feedback inhibition may be used for enhancing the activity of that enzyme. Furthermore, by increasing the expression of the operon (ace operon) that includes the maleate synthase gene (aceB), isocitrate lyase gene (aceA), and isocitrate dehydrogenase kinase/phosphatase gene (aceK), L-tryptophan-producing ability may be imparted or enhanced (WO2005/103275).

Examples of the L-phenylalanine biosynthesis enzymes can include, but are not particularly limited to, chorismate mutase and prephenate dehydratase. The chorismate mutase and prephenate dehydratase are encoded by the pheA gene as a bifunctional enzyme. Since the chorismate mutase and prephenate dehydratase are subject to feedback inhibition by L-phenylalanine, genes encoding these enzymes that have had a mutation introduced that causes desensitization to feedback inhibition may be used for enhancing the activities of these enzymes.

Examples of the L-tyrosine biosynthesis enzymes can include, but are not particularly limited to, chorismate mutase and prephenate dehydrogenase. The chorismate mutase and prephenate dehydrogenase are encoded by the tyrA gene as a bifunctional enzyme. Since the chorismate mutase and prephenate dehydrogenase are subject to feedback inhibition by L-tyrosine, genes encoding these enzymes that have had a mutation introduced that causes desensitization to feedback inhibition may be used for enhancing the activities of these enzymes.

The L-tryptophan, L-phenylalanine, and/or L-tyrosine-producing bacteria may be modified so that biosynthesis of an aromatic amino acid other than the objective aromatic amino acid is reduced. Furthermore, the L-tryptophan, L-phenylalanine, and/or L-tyrosine-producing bacteria may be modified so that a by-product uptake system is enhanced. Examples of the by-product can include aromatic amino acids other than the objective aromatic amino acid. Examples of the gene encoding such a by-product uptake system can include, for example, tnaB and mtr, which are genes encoding the L-tryptophan uptake system, pheP, which is a gene encoding the L-phenylalanine uptake system, and tyrP, which is a gene encoding the L-tyrosine uptake system (EP1484410).

Specific examples of L-tryptophan-producing bacteria and parental strains that can be used to derive them can include, for example, E. coli JP4735/pMU3028 (DSM10122) and JP6015/pMU91 (DSM10123), which have a mutant trpS gene encoding a partially inactivated tryptophanyl-tRNA synthetase (U.S. Pat. No. 5,756,345), E.

coli SV164, which has a trpE allele encoding an anthranilate synthase desensitized to feedback inhibition by tryptophan, *E. coli* SV164 (pGH5), which has a serA allele encoding a phosphoglycerate dehydrogenase desensitized to feedback inhibition by serine and a trpE allele encoding an anthranilate synthase desensitized to feedback inhibition by tryptophan (U.S. Pat. No. 6,180,373), a strain introduced with a tryptophan operon containing a trpE allele encoding an anthranilate synthase desensitized to feedback inhibition by tryptophan (Japanese Patent Laid-open (Kokai) Nos. 57-71397 and 62-244382, U.S. Pat. No. 4,371,614), *E. coli* AGX17(pGX44) (NRRL B-12263) and AGX6(pGX50)aroP (NRRL B-12264), which are deficient tryptophanase (U.S. Pat. No. 4,371,614), *E. coli* AGX17/pGX50, pACKG4-pps, which has an increased phosphoenolpyruvate-producing ability (WO97/08333, U.S. Pat. No. 6,319,696), and strains belonging to the genus *Escherichia* having an increased activity of the protein encoded by the yedA or yddG gene (U52003-0148473A1 and U52003-0157667A1).

Examples of coryneform bacteria having L-tryptophan-producing ability can include, for example, *Corynebacterium glutamicum* AJ12118 (FERM BP-478, Japanese Patent No. 1681002), which is resistant to sulfaguanidine, a strain in which the tryptophan operon has been introduced (Japanese Patent Laid-open (Kokai) No. 63-240794), and a strain in which a gene encoding shikimate kinase derived from a coryneform bacterium has been introduced (Japanese Patent No. 1994749).

Specific examples of L-phenylalanine-producing bacteria and parental strains that can be used to derive them can include, for example, *E. coli* AJ12739 (tyrA::Tn10, tyrR) (VKPM B-8197), which is deficient in the chorismate mutase-prephenate dehydrogenase and the tyrosine repressor (WO03/044191), *E. coli* HW1089 (ATCC 55371), which contains a mutant pheA34 gene encoding a chorismate mutase-prephenate dehydratase desensitized to feedback inhibition (U.S. Pat. No. 5,354,672), *E. coli* MWEC101-b (KR8903681), *E. coli* NRRL B-12141, NRRL B-12145, NRRL B-12146, and NRRL B-12147 (U.S. Pat. No. 4,407,952). Specific examples of L-phenylalanine-producing bacteria and parental strains that can be used to derive them also can include, for example, *E. coli* K-12<W3110(tyrA)/pPHAB> (FERM BP-3566), *E. coli* K-12<W3110(tyrA)/pPHAD> (FERM BP-12659), *E. coli* K-12<W3110(tyrA)/pPHATerm> (FERM BP-12662), and *E. coli* K-12 AJ12604<W3110(tyrA)/pBR-aroG4, pACMAB> (FERM BP-3579), which contains a gene encoding a chorismate mutase-prephenate dehydratase desensitized to feedback inhibition (EP488424B1). Specific examples of L-phenylalanine-producing bacteria and parental strains that can be used to derive them further can include, for example, strains belonging to the genus *Escherichia* having an increased activity of the protein encoded by the yedA gene or the yddG gene (US2003-0148473A, US2003-0157667A, WO03/044192).

Examples of coryneform bacteria having L-phenylalanine-producing ability can include, for example, the *Corynebacterium glutamicum* strains BPS-13 (FERM BP-1777), K77 (FERM BP-2062), and K78 (FERM BP-2063) (EP331145A, Japanese Patent Laid-open (Kokai) No. 02-303495), in which phosphoenolpyruvate carboxylase or pyruvate kinase activity is reduced, and the tyrosine-auxotrophic strain (Japanese Patent Laid-open (Kokai) No. 05-049489).

Examples of coryneform bacteria having L-tyrosine-producing ability can include, for example, *Corynebacterium glutamicum* AJ11655 (FERM P-5836, Japanese Patent Publication No. 2-6517), and *Corynebacterium glutamicum* (*Brevibacterium lactofermentum*) AJ12081 (FERM P-7249, Japanese Patent Laid-open (Kokai) No. 60-70093).

Furthermore, examples of methods for imparting or enhancing an L-amino acid-producing ability can include, for example, a method of modifying a bacterium so that the bacterium has an increased activity for secreting an L-amino acid from a bacterial cell. Such an activity for secreting an L-amino acid can be increased by, for example, increasing the expression of a gene encoding a protein responsible for secretion of the L-amino acid. Examples of genes encoding the proteins responsible for secretion of various amino acids can include, for example, b2682 gene (ygaZ), b2683 gene (ygaH), b1242 gene (ychE), and b3434 gene (yhgN) (Japanese Patent Laid-open (Kokai) No. 2002-300874).

Furthermore, examples of methods for imparting or enhancing an L-amino acid-producing ability also can include, for example, a method of modifying a bacterium so that the bacterium has an increased activity or activities of one or more proteins selected from proteins involved in the glycometabolism and proteins involved in the energy metabolism.

Examples of the proteins involved in the glycometabolism can include proteins involved in uptake of saccharides and the glycolysis system enzymes. Examples of genes encoding a protein involved in the glycometabolism can include glucose-6-phosphate isomerase gene (pgi, WO01/02542), pyruvate carboxylase gene (pyc, WO99/18228, EP1092776A), phosphoglucomutase gene (pgm, WO03/04598), fructose bisphosphate aldolase gene (pfkB, fbp, WO03/04664), transaldolase gene (talB, WO03/008611), fumarase gene (fum, WO01/02545), non-PTS sucrose uptake gene (csc, EP1149911A), and sucrose assimilation gene (scrAB operon, U.S. Pat. No. 7,179,623).

Examples of genes encoding the proteins involved in the energy metabolism can include the transhydrogenase gene (pntAB, U.S. Pat. No. 5,830,716) and cytochrome bo-type oxidase gene (cyoB, EP1070376A).

Furthermore, examples of methods for imparting or enhancing an ability to produce useful substances such as L-amino acids can include, for example, a method of modifying a bacterium so that the activity of phosphoketolase is increased (WO2006/016705). Hence, the bacterium may have been modified so that the activity of phosphoketolase is increased. This method may be effective particularly for imparting or enhancing an ability to produce an L-amino acid of the glutamate family such as L-glutamic acid. Examples of phosphoketolase can include D-xylulose-5-phosphate phosphoketolase and fructose-6-phosphate phosphoketolase. Either one of the D-xylulose-5-phosphate phosphoketolase activity and the fructose-6-phosphate phosphoketolase activity may be enhanced, or both may be enhanced.

The term "D-xylulose-5-phosphate phosphoketolase activity" can refer to an activity of converting xylulose-5-phosphate into glycelaldehyde-3-phosphate and acetyl phosphate while consuming phosphoric acid to release one molecule of $H_2O$. This activity can be measured by the method described by Goldberg, M. et al. (Methods Enzymol., 9, 515-520, 1996) or the method described by L. Meile (J. Bacteriol., 183:2929-2936, 2001). Examples of D-xylulose-5-phosphate phosphoketolase can include those of bacteria belonging to the genera *Acetobacter, Bifidobacterium, Lactobacillus, Thiobacillus, Streptococcus, Methylococcus, Butyrivibrio*, and *Fibrobacter*, and yeast belonging to the genera *Candida, Rhodotorula, Rhodosporidium, Pichia, Yarrowia, Hansenula, Kluyveromyces, Saccharomyces*,

*Trichosporon*, and *Wingea*. Specific examples of D-xylulose-5-phosphate phosphoketolase and genes encoding them are disclosed in WO2006/016705.

The term "fructose-6-phosphate phosphoketolase activity" can refer to an activity of converting fructose-6-phosphate into erythrose-4-phosphate and acetyl phosphate with consuming phosphoric acid to release one molecule of $H_2O$. This activity can be measured by the method described by Racker, E. (Methods Enzymol., 5, 276-280, 1962) or the method described by L. Meile (J. Bacteriol., 183:2929-2936, 2001). Examples of fructose-6-phosphate phosphoketolase can include those of bacteria belonging to the genera *Acetobacter, Bifidobacterium, Chlorobium, Brucella, Methylococcus*, and *Gardnerella*, and yeast belonging to the genera *Rhodotorula, Candida*, and *Saccharomyces*. Specific examples of fructose-6-phosphate phosphoketolase and genes encoding them are disclosed in WO2006/016705.

Both the D-xylulose-5-phosphate phosphoketolase activity and the fructose-6-phosphate phosphoketolase activity may also be retained by a single enzyme (i.e. D-xylulose-5-phosphate phosphoketolase/fructose-6-phosphate phosphoketolase).

The nucleotide sequence of the phosphoketolase gene (xfp gene) of *Bifidobacterium longum* JCM1217 and the amino acid sequence of the phosphoketolase encoded by the gene (Xfp protein) are shown in SEQ ID NOS: 13 and 14, respectively.

The genes and proteins used for breeding L-amino acid-producing bacteria may have, for example, the nucleotide sequences and amino acid sequences of known genes and proteins, such as those exemplified above, respectively. Also, the genes and proteins used for breeding L-amino acid-producing bacteria may be conservative variants of known genes and proteins, such as those exemplified above, respectively. Specifically, for example, the genes used for breeding L-amino acid-producing bacteria may each be a gene encoding a protein having an amino acid sequence of a known protein, but including substitution, deletion, insertion, or addition of one or several amino acid residues at one or several positions, so long as the original function thereof is maintained. For the conservative variants of genes and proteins, the descriptions concerning conservative variants of the C4-dicarboxylic acid-uptake carrier gene and C4-dicarboxylic acid-uptake carrier mentioned later can be applied, mutatis mutandis.

<1-2> Enhancement of C4-Dicarboxylic Acid-Uptake Carrier Activity

The bacterium can be modified so that the activity of a C4-dicarboxylic acid-uptake carrier is increased. The bacterium can be modified specifically so that the activity of a C4-dicarboxylic acid-uptake carrier is increased as compared with a non-modified strain. The bacterium can be obtained by modifying a bacterium having an L-amino acid-producing ability so that the activity of a C4-dicarboxylic acid-uptake carrier is increased. The bacterium can also be obtained by modifying a bacterium so that the activity of a C4-dicarboxylic acid-uptake carrier is increased, and then imparting or enhancing an L-amino acid-producing ability. The bacterium may also be a bacterium that has acquired an L-amino acid-producing ability by being modified so that the activity of a C4-dicarboxylic acid-uptake carrier is increased. The bacterium may have, as required, such a property possessed by an L-amino acid-producing bacterium as mentioned above, as well as being modified so that the activity of a C4-dicarboxylic acid-uptake carrier is increased. For example, the bacterium may have been modified so that the activity of phosphoketolase is increased. The modifications for constructing the bacterium can be performed in an arbitrary order.

By modifying a bacterium so that the activity of a C4-dicarboxylic acid-uptake carrier is increased, an L-amino acid-producing ability of the bacterium can be improved, and that is, production of an L-amino acid by using the bacterium can be increased. Particularly, it is expected that, by modifying a bacterium so that the activity of a C4-dicarboxylic acid-uptake carrier is increased, an L-amino acid-producing ability of the bacterium under conditions where L-aspartic acid is produced as a by-product can be improved, and that is, production of an L-amino acid by using the bacterium can be increased. Examples of the "increase in production of an L-amino acid" can include an improvement (increase) in the accumulation amount of the L-amino acid in a medium. That is, due to an increase in the activity of a C4-dicarboxylic acid-uptake carrier such as a DctA protein, more specifically, due to an increase in the expression of a C4-dicarboxylic acid-uptake carrier gene such as a dctA gene, for example, the accumulation amount of an L-amino acid such as L-glutamic acid in a medium may be improved, that is, increased. Furthermore, particularly, it is expected that, by modifying a bacterium so that the activity of a C4-dicarboxylic acid-uptake carrier is increased, by-production of L-aspartic acid can be decreased.

Hereinafter, C4-dicarboxylic acid-uptake carriers and genes encoding them will be explained.

The term "C4-dicarboxylic acid-uptake carrier" can refer to a protein having a C4-dicarboxylic acid-uptake activity. The term "C4-dicarboxylic acid-uptake activity" can refer to an activity to uptake a C4-dicarboxylic acid, that is, a carboxylic acid having 4 carbons, from outside of a cell to inside of the cell. Examples of the C4-dicarboxylic acid can include aspartic acid. A gene encoding a C4-dicarboxylic acid-uptake carrier is also referred to as "C4-dicarboxylic acid-uptake carrier gene".

Examples of the C4-dicarboxylic acid-uptake carrier gene can include a dctA gene, dcuA gene, and dcuB gene. Proteins encoded by a dctA gene, dcuA gene, and dcuB gene can also be referred to as a "DctA protein", "DcuA protein", and "DcuB protein", respectively. All these proteins have aspartic acid-uptake activity. The activity of one kind of C4-dicarboxylic acid-uptake carrier may be increased, or the activities of two or more kinds of C4-dicarboxylic acid-uptake carriers may be increased. That is, the C4-dicarboxylic acid-uptake carrier with increased activity may specifically be one or more of the DctA protein, DcuA protein, and DcuB protein. The activity of a C4-dicarboxylic acid-uptake carrier can be increased by, for example, increasing the expression of a C4-dicarboxylic acid-uptake carrier gene. That is, the expression "the activity of a C4-dicarboxylic acid-uptake carrier is increased" can mean that, for example, the expression of a C4-dicarboxylic acid-uptake carrier gene is increased. The expression "the activity of a C4-dicarboxylic acid-uptake carrier is increased" can also mean that, specifically, for example, the expression of one or more of the dctA gene, dcuA gene, and dcuB gene is increased.

Examples of the C4-dicarboxylic acid-uptake carrier gene can include genes of various organisms such as bacteria belonging to the family Enterobacteriaceae and coryneform bacteria. The nucleotide sequences of the C4-dicarboxylic acid-uptake carrier genes derived from various organisms and the amino acid sequences of the C4-dicarboxylic acid-uptake carriers encoded thereby can be obtained from, for example, public databases such as NCBI. Specific examples of a dctA gene can include, for example, the dctA gene (NCgl2506) of *C. glutamicum* and dctA gene of *E. coli*. Specific examples of a dcuA gene can include, for example, the dcuB gene of *E. coli*. Specific examples of a dcuB gene can include, for example, the dcuB gene of *E. coli*. The nucleotide sequence of the dctA gene (NCgl2506) of *C. glutamicum* 2256 (ATCC 13869) and the amino acid sequence of the protein encoded by the gene are shown in SEQ ID NOS: 15 and 16, respectively. The nucleotide sequence of the dctA gene (NCBI GeneID: 948039) of *E. coli* K-12 MG1655 and the amino acid sequence of the protein encoded by the gene are shown in SEQ ID NOS: 17 and 18, respectively. The nucleotide sequence of the dcuA gene (NCBI GeneID: 948659) of *E. coli* K-12 MG1655 and the amino acid sequence of the protein encoded by the gene are shown in SEQ ID NOS: 19 and 20, respectively. The nucleotide sequence of the dcuB gene (NCBI GeneID: 948641) of *E. coli* K-12 MG1655 and the amino acid sequence of the protein encoded by the gene are shown in SEQ ID NOS: 21 and 22, respectively. That is, the C4-dicarboxylic acid-uptake carrier gene may be, for example, a gene having the nucleotide sequence of any of the C4-dicarboxylic acid-uptake carrier genes exemplified above, such as the nucleotide sequence shown as SEQ ID NO: 15, 17, 19, or 21. Also, the C4-dicarboxylic acid-uptake carrier may be, for example, a protein having the amino acid sequence of any of the C4-dicarboxylic acid-uptake carriers exemplified above, such as the amino acid sequence shown as SEQ ID NO: 16, 18, 20, or 22. The expression "a gene or protein has a nucleotide or amino acid sequence" can mean that a gene or protein includes the nucleotide or amino acid sequence unless otherwise stated, and also includes when a gene or protein includes only the nucleotide or amino acid sequence.

The C4-dicarboxylic acid-uptake carrier gene may be a variant of any of the C4-dicarboxylic acid-uptake carrier genes exemplified above, that is, for example, a gene having the nucleotide sequence shown as SEQ ID NO: 15, 17, 19, or 21, so long as the original function thereof is maintained. Similarly, the C4-dicarboxylic acid-uptake carrier may be a variant of any of the C4-dicarboxylic acid-uptake carriers exemplified above, such as, for example, a protein having the amino acid sequence shown as SEQ ID NO: 16, 18, 20, or 22, so long as the original function thereof is maintained. Such a variant that maintains the original function thereof can also be referred to as a "conservative variant". The terms "dctA gene", "dcuA gene", and "dcuB gene" can include not only the dctA gene, dcuA gene, and dcuB gene exemplified above, respectively, but also can include conservative variants thereof. Similarly, the terms "DctA protein", "DcuA protein", and "DcuB protein" can include not only the DctA protein, DcuA protein, and DcuB protein exemplified above, respectively, but also can include conservative variants thereof. Examples of the conservative variants can include, for example, homologues and artificially modified versions of the C4-dicarboxylic acid-uptake carrier genes and C4-dicarboxylic acid-uptake carriers exemplified above.

The expression "the original function is maintained" can mean that a variant of gene or protein has a function, such as activity or property, corresponding to the function, such as activity or property, of the original gene or protein. The expression "the original function is maintained" when referring to a gene can mean that a variant of the gene encodes a protein that maintains the original function. That is, the expression "the original function is maintained" when referring to the C4-dicarboxylic acid-uptake carrier gene can mean that a variant of the gene encodes a protein having a C4-dicarboxylic acid-uptake activity, such as aspartic acid-uptake activity. Furthermore, the expression "the original function is maintained" when referring to the C4-dicarboxylic acid-uptake carrier can mean that a variant of the protein has a C4-dicarboxylic acid-uptake activity, such as aspartic acid-uptake activity.

The C4-dicarboxylic acid-uptake activity of a protein can be measured by, for example, incubating bacterial cells expressing the protein with a C4-dicarboxylic acid, and measuring the protein-dependent uptake of the C4-dicarboxylic acid into the cells.

Hereinafter, examples of the conservative variants will be explained.

Homologues of the C4-dicarboxylic acid-uptake carrier genes or homologues of the C4-dicarboxylic acid-uptake carriers can be easily obtained from public databases by, for example, a BLAST search or FASTA search using any of the nucleotide sequences of the C4-dicarboxylic acid-uptake carrier genes exemplified above or any of the amino acid sequences of the C4-dicarboxylic acid-uptake carriers exemplified above as a query sequence. Furthermore, homologues of the C4-dicarboxylic acid-uptake carrier genes can be obtained by, for example, PCR using a chromosome of various organisms as the template, and oligonucleotides prepared on the basis of any of the nucleotide sequences of these known C4-dicarboxylic acid-uptake carrier genes as primers.

The C4-dicarboxylic acid-uptake carrier gene may be a gene encoding a protein having any of the aforementioned amino acid sequences, for example, the amino acid sequences shown as SEQ ID NO: 16, 18, 20, or 22, but which includes substitution, deletion, insertion, and/or addition of one or several amino acid residues at one or several positions, so long as the original function is maintained. For example, the N-terminus and/or the C-terminus of the encoded protein may be elongated or shortened. Although the number meant by the term "one or several" may differ depending on the positions of amino acid residues in the three-dimensional structure of the protein or the types of amino acid residues, specifically, it is, for example, 1 to 50, 1 to 40, 1 to 30, 1 to 20, 1 to 10, 1 to 5, or 1 to 3.

The aforementioned substitution, deletion, insertion, and/or addition of one or several amino acid residues are/is a conservative mutation that maintains the normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions can include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, or addition of amino acid residues can include a naturally occurring mutation due to an individual difference, or a difference of species of the organism from which the gene is derived (mutant or variant).

The C4-dicarboxylic acid-uptake carrier gene may be a gene encoding a protein having an amino acid sequence showing a homology of, for example, 50% or more, 65% or more, 80% or more, 90% or more, 95% or more, 97% or more, or 99% or more, to the total amino acid sequence of any of the aforementioned amino acid sequences, so long as the original function is maintained. In this description, "homology" can mean "identity".

The C4-dicarboxylic acid-uptake carrier gene may also be a DNA that is able to hybridize under stringent conditions with a probe that can be prepared from any of the aforementioned nucleotide sequences, for example, the nucleotide sequence shown as SEQ ID NO: 15, 17, 19, or 21, such as a sequence complementary to a partial or entire sequence of any of the aforementioned nucleotide sequences, so long as the original function is maintained. The term "stringent conditions" can refer to conditions under which a so-called specific hybrid is formed, and a non-specific hybrid is not formed. Examples of the stringent conditions can include those under which highly homologous DNAs hybridize to each other, for example, DNAs not less than 50%, 65%, 80%, 90%, 95%, 97%, or 99% homologous, hybridize to each other, and DNAs less homologous than the above do not hybridize to each other, or can include washing conditions typical for Southern hybridization, that is, washing 1, 2, or 3 times, at a salt concentration and temperature of 1×SSC, 0.1% SDS at 60° C.; 0.1×SSC, 0.1% SDS at 60° C.; or 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of a known gene sequence as primers and a DNA fragment containing any of the aforementioned genes as a template. As the probe, for example, a DNA fragment having a length of about 300 bp can be used. When a DNA fragment having a length of about 300 bp is used as the probe, the washing conditions of the hybridization may be, for example, 50° C., 2×SSC and 0.1% SDS.

Furthermore, since the degeneracy of codons differs depending on the host, arbitrary codons in the C4-dicarboxylic acid-uptake carrier gene may be replaced with respective equivalent codons. That is, the C4-dicarboxylic acid-uptake carrier gene may be a variant of any of the C4-dicarboxylic acid-uptake carrier genes exemplified above due to the degeneracy of the genetic code. For example, the C4-dicarboxylic acid-uptake carrier gene may be a gene modified so that it has optimal codons according to codon frequencies in a host to be used.

The percentage of the sequence identity between two sequences can be determined by, for example, using a mathematical algorithm. Non-limiting examples of such a mathematical algorithm can include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and an modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison, for example, alignment, for determining the sequence identity can be performed. The program can be appropriately executed by a computer. Examples of such a program can include, but are not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244 (1988), Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other.

The aforementioned descriptions concerning conservative variants of the genes and proteins can be applied mutatis mutandis to variants of arbitrary proteins such as L-amino acid biosynthesis system enzymes and genes encoding them.

<1-3> Methods for Increasing Activity of Protein

Hereinafter, the methods for increasing the activity of a protein such as the C4-dicarboxylic acid-uptake carrier will be explained.

The expression "the activity of a protein is increased" can mean that the activity of the protein is increased as compared with a non-modified strain. Specifically, the expression "the activity of a protein is increased" can mean that the activity of the protein per cell is increased as compared with that of a non-modified strain. The term "non-modified strain" or "non-modified bacterium" can refer to a control strain that has not been modified so that the activity of an objective protein is increased. Examples of the non-modified strain can include a wild-type strain and parent strain. Specific examples of the non-modified strain can include the respective type strains of the species of bacteria. Specific examples of the non-modified strain also can include strains exemplified above in relation to the description of bacteria. That is, in an embodiment, the activity of a protein may be increased as compared with a type strain, for example, the type strain of the species to which the bacterium belongs. In another embodiment, the activity of a protein may also be increased as compared with the C. glutamicum ATCC 13032 strain. In another embodiment, the activity of a protein may also be increased as compared with the C. glutamicum 2256 strain (ATCC 13869). In another embodiment, the activity of a protein may also be increased as compared with the E. coli K-12 MG1655 strain. In another embodiment, the activity of a protein may also be increased as compared with the P. ananatis AJ13355 strain. The state that "the activity of a protein is increased" may also be expressed as "the activity of a protein is enhanced". More specifically, the expression "the activity of a protein is increased" may mean that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but may also mean the transcription amount of a gene, that is, the amount of mRNA, encoding the protein, or the translation amount of the protein, that is the amount of the protein. Furthermore, the state that "the activity of a protein is increased" can include not only when the activity of an objective protein is increased in a strain inherently having the activity of the objective protein, but also when the activity of an objective protein is imparted to a strain not inherently having the activity of the objective protein. Furthermore, so long as the activity of the protein is eventually increased, the activity of an objective protein inherently present in a host may be attenuated and/or eliminated, and then an appropriate type of the objective protein may be imparted to the host.

The degree of the increase in the activity of a protein is not particularly limited, so long as the activity of the protein is increased as compared with a non-modified strain. The activity of the protein may be increased to, for example, 1.5 times or more, 2 times or more, or 3 times or more of that of a non-modified strain. Furthermore, when the non-modified strain does not have the activity of the objective protein, it is sufficient that the protein is produced as a result of introduction of the gene encoding the protein, and for example, the protein may be produced to such an extent that the activity thereof can be measured.

The modification for increasing the activity of a protein can be attained by, for example, increasing the expression of a gene encoding the protein. The expression "the expression of a gene is increased" can mean that the expression of the gene is increased as compared with a non-modified strain such as a wild-type strain and parent strain. Specifically, the expression "the expression of a gene is increased" can mean that the expression amount of the gene per cell is increased as compared with that of a non-modified strain. More specifically, the expression "the expression of a gene is increased" may mean that the transcription amount of the gene (i.e. the amount of mRNA) is increased, and/or the translation amount of the gene (i.e. the amount of the protein expressed from the gene) is increased. The state that "the expression of a gene is increased" may also be referred to as "the expression of a gene is enhanced". The expression of a gene may be increased to, for example, 1.5 times or more, 2 times or more, or 3 times or more of that of a non-modified strain. Furthermore, the state that "the expression of a gene is increased" includes not only when the expression amount of an objective gene is increased in a strain that inherently expresses the objective gene, but also when the gene is introduced into a strain that does not inherently express the objective gene, and expressed therein. That is, the phrase "the expression of a gene is increased" may also mean, for example, that an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination can include, for example, a method of using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome can include repetitive DNAs, and inverted repeats located at the both ends of a transposon. Alternatively, homologous recombination may be performed by using an appropriate sequence on a chromosome such as a gene unnecessary for production of an objective substance as a target. Furthermore, a gene can also be randomly introduced into a chromosome by using a transposon or Mini-Mu (Japanese Patent Laid-open (Kokai) No. 2-109985, U.S. Pat. No. 5,882,888, EP805867B1).

Introduction of a target gene into a chromosome can be confirmed by Southern hybridization using a probe having a sequence complementary to the whole gene or a part thereof, PCR using primers prepared on the basis of the sequence of the gene, or the like.

Furthermore, the copy number of a gene can also be increased by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment containing the target gene can be obtained by, for example, PCR using the genomic DNA of a microorganism having the target gene as the template. As the vector, a vector autonomously replicable in the cell of the host can be used. The vector can be a multi-copy vector. Furthermore, the vector can have a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vectors autonomously replicable in Enterobacteriaceae bacteria such as Escherichia coli can include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pCold TF DNA (Takara Bio), pACYC series vectors, and the broad host spectrum vector RSF1010. Specific examples of vectors autonomously replicable in coryneform bacteria can include, for example, pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 (Japanese Patent Laid-open (Kokai) No. 3-210184); plasmids pCRY21, pCRY2KE, pCRY2KX, pCRY31, pCRY3KE, and pCRY3KX (Japanese Patent Laid-open (Kokai) No. 2-72876 and U.S. Pat. No. 5,185,262); plasmids pCRY2 and pCRY3 (Japanese Patent Laid-open (Kokai) No. 1-191686); pAJ655, pAJ611, and pAJ1844 (Japanese Patent Laid-open (Kokai) No. 58-192900); pCG1 (Japanese Patent Laid-open (Kokai) No. 57-134500); pCG2 (Japanese Patent Laid-open (Kokai) No. 58-35197); pCG4 and pCG11 (Japanese Patent Laid-open (Kokai) No. 57-183799); pVK7 (Japanese Patent Laid-open (Kokai) No. 10-215883); pVK9 (US2006-0141588); pVC7 (Japanese Patent Laid-open (Kokai) No. 9-070291); pVS7 (WO2013/069634).

When a gene is introduced, it is sufficient that the gene is able to be expressed by a host. Specifically, it is sufficient that the gene is expressed under control by a promoter that functions in the host. The promoter is not particularly limited so long as it functions in the host. The term "promoter that functions in a host" can refer to a promoter that shows a promoter activity in the host. The promoter may be a promoter derived from the host, or a heterogenous promoter. The promoter may be the native promoter of the gene to be introduced, or a promoter of another gene. As the promoter, for example, such a stronger promoter as mentioned later may also be used.

A terminator for termination of gene transcription may be located downstream of the gene. The terminator is not particularly limited so long as it functions in the host. The terminator may be a terminator derived from the host, or a heterogenous terminator. The terminator may be the native terminator of the gene to be introduced, or a terminator of another gene. Specific examples of the terminator can include, for example, T7 terminator, T4 terminator, fd phage terminator, tet terminator, and trpA terminator.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Furthermore, when two or more of genes are introduced, it is sufficient that the genes each are able to be expressed by the host. For example, all the genes may be present in a single expression vector or a chromosome. Furthermore, the genes may be separately present in two or more expression vectors, or separately present in a single or two or more expression vectors and a chromosome. An operon containing two or more genes may also be introduced. The case of "introducing two or more genes" can include, for example, cases of introducing respective genes encoding two or more kinds of proteins (such as enzymes), introducing respective genes encoding two or more subunits constituting a single protein complex (such as enzyme complex), and a combination of the foregoing cases.

The gene to be introduced is not particularly limited so long as it encodes a protein that functions in the host. The gene to be introduced may be a gene derived from the host, or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as a template. The gene to be introduced may also be totally synthesized, for example, on the basis of the nucleotide sequence of the gene (Gene, 60(1), 115-127 (1987)). The obtained gene can be used as it is, or after being modified as required. A gene can be modified by a known technique. For example, an objective mutation can be introduced into an objective site of DNA by the site-specific mutation method. That is, the coding region of a gene can be modified by the site-specific mutation method so that a specific site of the encoded protein can include substitution, deletion, insertion, and/or addition of amino acid residues. Examples of the site-specific mutation method can include the method utilizing PCR (Higuchi, R., 61, in PCR Technology, Erlich, H. A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)).

Incidentally, when a protein functions as a complex made up of a plurality of subunits, a part or all of the subunits may be modified, so long as the activity of the protein is eventually increased. That is, for example, when the activity of a protein is increased by increasing the expression of a gene, the expression of a part or all of the genes that encode the subunits may be enhanced. It is usually preferable to enhance the expression of all of the genes encoding the subunits. Furthermore, the subunits making up the complex may be derived from a single kind of organism or two or more kinds of organisms, so long as the complex has a function of the objective protein. That is, for example, genes of the same organism encoding a plurality of subunits may be introduced into a host, or genes of different organisms encoding a plurality of subunits may be introduced into a host.

Furthermore, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively can refer to sites that affect the expression of a gene. Examples of the expression control sequence can include, for example, promoter, Shine-Dalgarno (SD) sequence (also referred to as ribosome binding site (RBS)), and spacer region between RBS and the start codon. Expression control sequences can be identified by using a promoter search vector or gene analysis software such as GENETYX. These expression control sequences can be modified by, for example, a method of using a temperature sensitive vector, or the Red driven integration method (WO2005/010175).

The transcription efficiency of a gene can be improved by, for example, replacing the promoter of the gene on a chromosome with a stronger promoter. The term "stronger promoter" can refer to a promoter providing an improved transcription of a gene compared with an inherently present wild-type promoter of the gene. Examples of stronger promoters can include, for example, the known high expression promoters such as T7 promoter, trp promoter, lac promoter, thr promoter, tac promoter, trc promoter, tet promoter, araBAD promoter, rpoH promoter, msrA promoter, Pm1 promoter (derived from the genus *Bifidobacterium*), PR promoter, and PL promoter. Examples of stronger promoters usable in coryneform bacteria can include, for example, the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, cspB, SOD, and tuf (EF-Tu) promoters, which are potent promoters capable of providing a large expression amount in coryneform bacteria (Journal of Biotechnology, 104 (2003) 311-323; Appl. Environ. Microbiol., 2005 December; 71 (12): 8587-96), as well as lac promoter, tac promoter, and trc promoter. Furthermore, as the stronger promoter, a highly-active type of an existing promoter may also be obtained by using various reporter genes. For example, by making the −35 and −10 regions in a promoter region closer to the consensus sequence, the activity of the promoter can be enhanced (WO00/18935). Examples of highly active-type promoter can include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The translation efficiency of a gene can be improved by, for example, replacing the Shine-Dalgarno (SD) sequence, also referred to as ribosome binding site (RBS), for the gene on a chromosome with a stronger SD sequence. The "stronger SD sequence" can mean a SD sequence that provides an improved translation of mRNA as compared with the inherently present wild-type SD sequence of the gene. Examples of stronger SD sequences can include, for example, RBS of the gene 10 derived from phage T7 (Olins P. O. et al, Gene, 1988, 73, 227-235). Furthermore, it is known that substitution, insertion, or deletion of several nucleotides in a spacer region between RBS and the start codon, especially in a sequence immediately upstream of the start codon (5'-UTR), significantly affects the stability and translation efficiency of mRNA, and hence, the translation efficiency of a gene can also be improved by modifying them.

The translation efficiency of a gene can also be improved by, for example, modifying codons. For example, the translation efficiency of the gene can be improved by replacing a rare codon present in the gene with a more frequently used synonymous codon. That is, the gene to be introduced may be modified, for example, so as to contain optimal codons according to the frequencies of codons observed in the chosen host. Codons can be replaced by, for example, the site-specific mutation method. Alternatively, a gene fragment in which objective codons are replaced may be totally synthesized. Frequencies of codons in various organisms are disclosed in the "Codon Usage Database" (kazusa.or.jp/codon; Nakamura, Y. et al, Nucl. Acids Res., 28, 292 (2000)).

Furthermore, the expression of a gene can also be increased by amplifying a regulator that increases the expression of the gene, or deleting or attenuating a regulator that reduces the expression of the gene.

Such methods for increasing the gene expression as mentioned above may be used independently or in an arbitrary combination.

Furthermore, the modification that increases the activity of a protein can also be attained by, for example, enhancing the specific activity of the enzyme. Enhancement of the specific activity can also include desensitization to feedback inhibition. That is, when a protein is subject to feedback inhibition by a metabolite, the activity of the protein can be increased by making the bacterium harbor a gene encoding a mutant protein that has been desensitized to the feedback inhibition. The term "desensitization to feedback inhibition" can include complete elimination of the feedback inhibition, and attenuation of the feedback inhibition, unless otherwise stated. Also, the state of "being desensitized to feedback inhibition", that is, the state that feedback inhibition is eliminated or attenuated, may also be referred to as "tolerant to feedback inhibition". A protein showing an enhanced specific activity can be obtained by, for example, searching various organisms. Furthermore, a highly-active type of an existing protein may also be obtained by introducing a mutation into the existing protein. The mutation to be introduced may be, for example, substitution, deletion, insertion, or addition of one or several amino acid residues at one or several positions of the protein. The mutation can be introduced by, for example, such a site-specific mutation method as mentioned above. The mutation may also be introduced by, for example, a mutagenesis treatment. Examples of the mutagenesis treatment can include irradiation of X-ray, irradiation of ultraviolet, and a treatment with a mutation agent such as N-methyl-N'-nitro-N-nitrosoguanidine (MNNG), ethyl methanesulfonate (EMS), and methyl methanesulfonate (MMS). Furthermore, a random mutation may be induced by directly treating DNA in vitro with hydroxylamine. Enhancement of the specific activity may be independently used, or may be used in an arbitrary combination with such methods for enhancing gene expression as mentioned above.

The method for the transformation is not particularly limited, and conventionally known methods can be used. There can be used, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and a method of preparing competent cells from cells which are in the growth phase, followed by transformation with DNA, which has been reported for *Bacillus subtilis* (Duncan, C. H., Wilson, G. A. and Young, F. E., Gene, 1977, 1:153-167). Alternatively, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Furthermore, the electric pulse method reported for coryneform bacteria (Japanese Patent Laid-open (Kokai) No. 2-207791) can also be used.

An increase in the activity of a protein can be confirmed by measuring the activity of the protein.

An increase in the activity of a protein can also be confirmed by confirming an increase in the expression of a gene encoding the protein. An increase in the expression of a gene can be confirmed by confirming an increase in the transcription amount of the gene, or by confirming an increase in the amount of a protein expressed from the gene.

An increase of the transcription amount of a gene can be confirmed by comparing the amount of mRNA transcribed from the gene with that of a non-modified strain such as a wild-type strain or parent strain. Examples of the method for evaluating the amount of mRNA can include Northern hybridization, RT-PCR, and so forth (Sambrook, J., et al., Molecular Cloning A Laboratory Manual/Third Edition, Cold Spring Harbor Laboratory Press, Cold Spring Harbor (USA), 2001). The amount of mRNA may increase to, for example, 1.5 times or more, 2 times or more, or 3 times or more of that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein, such as the number of molecules of the protein per cell, may increase to, for example, 1.5 times or more, 2 times or more, or 3 times or more of that of a non-modified strain.

The aforementioned methods for increasing the activity of a protein can be used for enhancement of the activities of arbitrary proteins such as L-amino acid biosynthesis enzymes, and enhancement of the expression of arbitrary genes such as genes encoding those arbitrary proteins, besides enhancement of C4-dicarboxylic acid-uptake carrier activity.

<1-4> Method for Reducing Activity of Protein

Hereinafter, the methods for reducing the activity of a protein will be explained.

The expression "the activity of a protein is reduced" can mean that the activity of the protein is reduced as compared with a non-modified strain. Specifically, the expression "the activity of a protein is reduced" can mean that the activity of the protein per cell is reduced as compared with that of a non-modified strain. The term "non-modified strain" can refer to a control strain that has not been modified so that the activity of an objective protein is reduced. Examples of the non-modified strain can include a wild-type strain and parent strain. Specific examples of the non-modified strain can include the respective type strains of the species of bacteria. Specific examples of the non-modified strain also can include strains exemplified above in relation to the description of bacteria. That is, in an embodiment, the activity of a protein may be reduced as compared with a type strain, that is, the type strain of the species to which the chosen bacterium belongs. In another embodiment, the activity of a protein may also be reduced as compared with the *C. glutamicum* ATCC 13032 strain. In another embodiment, the activity of a protein may also be reduced as compared with the *C. glutamicum* 2256 strain (ATCC 13869). In another embodiment, the activity of a protein may also be reduced as compared with the *E. coli* K-12 MG1655 strain. In another embodiment, the activity of a protein may also be reduced as compared with the *P. ananatis* AJ13355 strain. The state that "the activity of a protein is reduced" also can include a state that the activity of the protein has completely disappeared. More specifically, the expression "the activity of a protein is reduced" may mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene, that is, the amount of mRNA, encoding the protein or the translation amount of the protein, that is, the amount of the protein. The state that "the number of molecules of the protein per cell is reduced" also can include when the protein does not exist at all. The state that "the function of each molecule of the protein is reduced" also can include when the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The expression "the expression of a gene is reduced" can mean that the expression of the gene is reduced as compared with a non-modified strain such as a wild-type strain and parent strain. Specifically, the expression "the expression of a gene is reduced" can mean that the expression of the gene per cell is reduced as compared with that of a non-modified strain. More specifically, the expression "the expression of a gene is reduced" may mean that the transcription amount of the gene, that is, the amount of mRNA, is reduced, and/or the translation amount of the gene, that is, the amount of the protein expressed from the gene, is reduced. The state that "the expression of a gene is reduced" also can include a state that the gene is not expressed at all. The state that "the expression of a gene is reduced" can also be referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of these. The expression of a gene can be reduced by modifying an expression control sequence of the gene such as a promoter, Shine-Dalgarno (SD) sequence, also referred to as ribosome-binding site (RBS), and spacer region between RBS and the start codon of the gene. When an expression control sequence is modified, one or more nucleotides, two or more nucleotides, or three or more nucleotides, of the expression control sequence can be modified. For example, the transcription efficiency of a gene can be reduced by, for example, replacing the promoter of the gene on a chromosome with a weaker promoter. The term "weaker promoter" can mean a promoter providing an attenuated transcription of a gene compared with an inherently present wild-type promoter of the gene. Examples of weaker promoters can include, for example, inducible promoters. That is, an inducible promoter may function as a weaker promoter under a non-induced condition, such as in the absence of the corresponding inducer. Furthermore, a part or the entire expression control sequence may be deleted. The expression of a gene can also be reduced by, for example, manipulating a factor responsible for expression control. Examples of the factor responsible for expression control can include low molecules responsible for transcription or translation control, such as inducers, inhibitors, etc., proteins responsible for transcription or translation control, such as transcription factors etc., nucleic acids responsible for transcription or translation control, such as siRNA etc., and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described later.

The modification for reducing the activity of a protein can also be attained by, for example, disrupting a gene encoding the protein. The expression "a gene is disrupted" can mean that a gene is modified so that a protein that can normally function is not produced. The state that "a protein that normally functions is not produced" can include when the protein is not produced at all from the gene, and also when the protein of which the function, such as activity or property per molecule is reduced or eliminated is produced from the gene.

Disruption of a gene can be attained by, for example, deleting the gene on a chromosome. The term "deletion of a gene" can refer to deletion of a partial or entire region of the coding region of the gene. Furthermore, the whole of a gene including sequences upstream and downstream from the coding region of the gene on a chromosome may be deleted. The region to be deleted may be any region such as an N-terminal region, that is, a region encoding an N-terminal region of a protein, an internal region, or a C-terminal region, that is, a region encoding a C-terminal region of a protein, so long as the activity of the protein can be reduced. Deletion of a longer region can usually more surely inactivate the gene. The region to be deleted may be, for example, a region having a length of 10% or more, 20% or more, 30% or more, 40% or more, 50% or more, 60% or more, 70% or more, 80% or more, 90% or more, or 95% or more of the total length of the coding region of the gene. Furthermore, it is preferred that reading frames of the sequences upstream and downstream from the region to be deleted are not the same. Inconsistency of reading frames may cause a frameshift downstream of the region to be deleted.

Disruption of a gene can also be attained by, for example, introducing a mutation for an amino acid substitution (missense mutation), a stop codon (nonsense mutation), addition or deletion of one or two nucleotide residues (frame shift mutation), or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another nucleotide sequence into a coding region of the gene on a chromosome. The site of the insertion may be in any region of the gene, and insertion of a longer nucleotide sequence can usually more surely inactivate the gene. It is preferred that reading frames of the sequences upstream and downstream from the insertion site are not the same. Inconsistency of reading frames may cause a frameshift downstream of the region to be deleted. The other nucleotide sequence is not particularly limited so long as a sequence that reduces or eliminates the activity of the encoded protein is chosen, and examples thereof can include, for example, a marker gene such as antibiotic resistance genes, and a gene useful for production of an objective substance.

Particularly, disruption of a gene may be carried out so that the amino acid sequence of the encoded protein is deleted. In other words, the modification for reducing the activity of a protein can be attained by, for example, deleting the amino acid sequence of the protein, specifically, modifying a gene so as to encode a protein of which the amino acid sequence is deleted. The term "deletion of the amino acid sequence of a protein" can refer to deletion of a partial or entire region of the amino acid sequence of the protein. In addition, the term "deletion of the amino acid sequence of a protein" can mean that the original amino acid sequence disappears in the protein, and also includes when the original amino acid sequence is changed to another amino acid sequence. That is, for example, a region that was changed to another amino acid sequence by frameshift may be regarded as a deleted region. When the amino acid sequence of a protein is deleted, the total length of the protein is typically shortened, but there can also be cases where the total length of the protein is not changed or is extended. For example, by deletion of a partial or entire region of the coding region of a gene, a region encoded by the deleted region can be deleted in the encoded protein. In addition, for example, by introduction of a stop codon into the coding region of a gene, a region encoded by the downstream region of the introduction site can be deleted in the encoded protein. In addition, for example, by frameshift in the coding region of a gene, a region encoded by the frameshift region can be deleted in the encoded protein. The aforementioned descriptions concerning the position and length of the region to be deleted in deletion of a gene can be applied mutatis mutandis to the position and length of the region to be deleted in deletion of the amino acid sequence of a protein.

Such modification of a gene on a chromosome as described above can be attained by, for example, preparing a disruption-type gene modified so that it is unable to produce a protein that functions normally, and transforming a host with a recombinant DNA containing the disruption-type gene to cause homologous recombination between the disruption-type gene and the wild-type gene on a chromosome and thereby substitute the disruption-type gene for the wild-type gene on the chromosome. In this procedure, if a marker gene selected according to the characteristics of the host such as auxotrophy is included in the recombinant DNA, the operation becomes easier. Examples of the disruption-type gene can include a gene of which a partial or the entire coding region is deleted, gene including a missense mutation, gene including a nonsense mutation, gene including a frame shift mutation, and gene introduced with an insertion sequence such as a transposon or marker gene. The protein encoded by the disruption-type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

Modification for reducing activity of a protein can also be attained by, for example, a mutagenesis treatment. Examples of the mutagenesis treatment can include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

Such methods for reducing the activity of a protein as mentioned above may be used independently or in an arbitrary combination.

When a protein functions as a complex made up of a plurality of subunits, a part or all of the subunits may be modified, so long as the activity of the protein is eventually reduced. That is, for example, a part or all of the genes that encode the respective subunits may be disrupted or the like. Furthermore, when there is a plurality of isozymes of a protein, a part or all of the activities of the plurality of isozymes may be reduced, so long as the activity of the protein is eventually reduced. That is, for example, a part or all of a plurality of genes that encode the respective isozymes may be disrupted or the like.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA can include Northern hybridization, RT-PCR, and so forth (Molecular Cloning, Cold Spring Harbor Laboratory Press, Cold Spring Harbor (USA), 2001). The amount of mRNA is preferably reduced to, for example, 50% or less, 20% or less, 10% or less, 5% or less, or 0% of that of a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein (such as the number of molecules of the protein per cell) is preferably reduced to, for example, 50% or less, 20% or less, 10% or less, 5% or less, or 0% of that of a non-modified strain.

Disruption of a gene can be confirmed by determining nucleotide sequence of a part or the whole gene, restriction enzyme map, full length, or the like of the gene depending on the means used for the disruption.

The aforementioned methods for reducing the activity of a protein as mentioned above can be applied to reduction in the activities of arbitrary proteins such as an enzyme that catalyzes a reaction branching away from the biosynthesis pathway of an objective L-amino acid to generate a compound other than the objective L-amino acid, and reduction in the expression of arbitrary genes such as genes encoding those arbitrary proteins.

<2> Method for Producing L-Amino Acid of the Present Invention

The method as described herein is a method for producing an L-amino acid that includes the steps of culturing the bacterium as described herein in a medium to accumulate an L-amino acid in the medium and/or cells of the bacterium, and collecting the L-amino acid from the medium and/or cells of the bacterium. The L-amino acid produced is an L-amino acid other than L-aspartic acid. One kind of L-amino acid may be produced, or two or more kinds of L-amino acids may be produced.

The medium is not particularly limited, so long as the chosen bacterium can proliferate in the chosen medium, and an objective L-amino acid can be produced. As the medium, for example, a medium typically used for culture of bacteria such as coryneform bacteria and Enterobacteriaceae bacteria can be used. As the medium, for example, a medium containing a carbon source, nitrogen source, phosphorus source, and sulfur source, as well as other various organic components and inorganic components as required can be used. Types and concentrations of the medium components can be appropriately determined according to various conditions such as the type of bacterium to be used.

Specific examples of the carbon source can include, for example, saccharides such as glucose, fructose, sucrose, lactose, galactose, xylose, arabinose, blackstrap molasses, hydrolysates of starches, and hydrolysates of biomass, organic acids such as acetic acid, fumaric acid, citric acid, and succinic acid, alcohols such as glycerol, crude glycerol, and ethanol, and aliphatic acids. As the carbon source, plant-derived materials can be preferably used. Examples of the plant can include, for example, corn, rice, wheat, soybean, sugarcane, beet, and cotton. Examples of the plant-derived materials can include, for example, organs such as root, stem, trunk, branch, leaf, flower, and seed, plant bodies including them, and decomposition products of these plant organs. The forms of the plant-derived materials at the time of use thereof are not particularly limited, and they can be used in any form such as an unprocessed product, juice, ground product, and purified product. Pentoses such as xylose, hexoses such as glucose, or mixtures of them can be obtained from, for example, plant biomass, and used. Specifically, these saccharides can be obtained by subjecting a plant biomass to a treatment such as a steam treatment, hydrolysis with concentrated acid, hydrolysis with diluted acid, hydrolysis with an enzyme such as cellulase, and alkaline treatment. Since hemicellulose is generally more easily hydrolyzed compared with cellulose, hemicellulose in a plant biomass may be hydrolyzed beforehand to liberate pentoses, and then cellulose may be hydrolyzed to generate hexoses. Furthermore, xylose may be supplied by conversion from hexoses by, for example, imparting a pathway for converting hexose such as glucose to xylose to the bacterium. As the carbon source, a single kind of carbon source may be used, or two or more kinds of carbon sources may be used in combination.

Specific examples of the nitrogen source can include, for example, ammonium salts such as ammonium sulfate, ammonium chloride, and ammonium phosphate, organic nitrogen sources such as peptone, yeast extract, meat extract, and soybean protein decomposition products, ammonia, and urea. Ammonia gas or aqueous ammonia used for adjusting pH may also be used as the nitrogen source. As the nitrogen source, a single kind of nitrogen source may be used, or two or more kinds of nitrogen sources may be used in combination.

Specific examples of the phosphate source can include, for example, phosphoric acid salts such as potassium dihydrogenphosphate and dipotassium hydrogenphosphate, and phosphoric acid polymers such as pyrophosphoric acid. As the phosphate source, a single kind of phosphate source may be used, or two or more kinds of phosphate sources may be used in combination.

Specific examples of the sulfur source can include, for example, inorganic sulfur compounds such as sulfates, thiosulfates, and sulfites, and sulfur-containing amino acids such as cysteine, cystine, and glutathione. As the sulfur source, a single kind of sulfur source may be used, or two or more kinds of sulfur sources may be used in combination.

Specific examples of other various organic components and inorganic components can include, for example, inorganic salts such as sodium chloride and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing those such as peptone, casamino acid, yeast extract, and soybean protein decomposition product. As other various organic components and inorganic components, a single kind of component may be used, or two or more kinds of components may be used in combination.

Furthermore, when an auxotrophic mutant that requires an amino acid or the like for growth thereof is used, it is preferable to supply a required nutrient to the medium.

Furthermore, it is also preferable to, for example, restrict the amount of biotin in the medium, or add a surfactant or penicillin to the medium.

The culture conditions are not particularly limited so long as the chosen bacterium can proliferate, and an objective L-amino acid can be produced. The culture can be performed, for example, under conditions typically used for culturing bacteria such as coryneform bacteria and Enterobacteriaceae bacteria. The culture conditions can be appropriately set according to various conditions such as the type of chosen bacterium.

The culture can be performed by using a liquid medium. At the time of the culture, the bacterium cultured on a solid medium such as agar medium may be directly inoculated into a liquid medium, or the bacterium cultured in a liquid medium as seed culture may be inoculated into a liquid medium for main culture. That is, the culture may be performed separately as seed culture and main culture. In such a case, the culture conditions of the seed culture and the main culture may be or may not be the same. The amount of the bacterium present in the medium at the time of the start of the culture is not particularly limited. The main culture may be performed by, for example, inoculating a seed culture broth to a medium for main culture at an amount of 1 to 50% (v/v).

The culture can be performed as batch culture, fed-batch culture, continuous culture, or a combination of these. The medium used at the time of the start of the culture can also be referred to as "starting medium". The medium supplied to a culture system, such as a fermentation tank, in fed-batch culture or continuous culture can also be referred to as "feed medium". Furthermore, to supply a feed medium to a culture system in fed-batch culture or continuous culture can also be referred to as to "feed". Furthermore, when the culture is performed separately as seed culture and main culture, for example, both the seed culture and the main culture may be performed as batch culture. Alternatively, for example, the seed culture may be performed as batch culture, and the main culture may be performed as fed-batch culture or continuous culture.

The medium components each may be present in the starting medium, feed medium, or both. The types of the components present in the starting medium may be or may not be the same as the types of the components present in the feed medium. The concentration of each component present in the starting medium may be or may not be the same as the concentration of the component present in the feed medium. Furthermore, two or more kinds of feed media containing different types and/or different concentrations of components may be used. For example, when medium is intermittently fed a plurality of times, the types and/or concentrations of components present in the feed media may be or may not be the same for each feeding.

The concentration of the carbon source in the medium is not particularly limited, so long as the bacterium can proliferate and produce an L-amino acid. The concentration of the carbon source in the medium may be as high as possible within such a range that production of the L-amino acid is not inhibited. The concentration of the carbon source in the medium may be, as the initial concentration, that is, the concentration in the starting medium, for example, 1 to 30% (w/v), or 3 to 10% (w/v). Furthermore, the carbon source may be additionally supplied to the medium as required. For example, the carbon source may be additionally supplied to the medium in proportion to consumption of the carbon source accompanying progress of the fermentation.

The culture can be performed, for example, under an aerobic condition. The term "aerobic condition" can refer to a condition where the dissolved oxygen concentration in the liquid medium is not lower than 0.33 ppm, which is the detection limit for the detection with an oxygen membrane electrode, or may also refer to a condition where the dissolved oxygen concentration in the liquid medium is not lower than 1.5 ppm. The oxygen concentration can be controlled to, for example, 5 to 50%, or about 10%, of the saturated oxygen concentration. Specifically, the culture under an aerobic condition can be performed by aeration culture, shaking culture, stirring culture, or a combination thereof. The pH of the medium may be, for example, 3 to 10, or 4.0 to 9.5. During the culture, the pH of the medium can be adjusted as required. The pH of the medium can be adjusted by using various alkaline and acidic substances such as ammonia gas, aqueous ammonia, sodium carbonate, sodium bicarbonate, potassium carbonate, potassium bicarbonate, magnesium carbonate, sodium hydroxide, calcium hydroxide, and magnesium hydroxide. The culture temperature may be, for example, 20 to 45° C., or 25 to 37° C. The culture period may be, for example, 10 to 120 hours. The culture may be continued, for example, until the carbon source present in the medium is consumed, or until the bacterium loses the activity. By culturing the bacterium under such conditions as described above, an L-amino acid can be accumulated in the medium and/or cells of the bacterium.

Moreover, when L-glutamic acid is produced, the culture can be performed by using a liquid medium adjusted to satisfy a condition under which L-glutamic acid is precipitated, while precipitating L-glutamic acid in the medium. Examples of the condition under which L-glutamic acid is precipitated can include, for example, pH 5.0 to 4.0, pH 4.5 to 4.0, pH 4.3 to 4.0, or around pH 4.0 (EP1078989A).

Production of an L-amino acid can be confirmed by known methods used for detection or identification of compounds. Examples of such methods can include, for example, HPLC, LC/MS, GC/MS, and NMR. These methods can be independently used, or can be used in an appropriate combination.

The produced L-amino acid can be collected from the fermentation broth by known methods used for separation and purification of compounds. Examples of such methods can include, for example, ion-exchange resin method (Nagai, H. et al., Separation Science and Technology, 39(16), 3691-3710), precipitation, membrane separation (Japanese Patent Laid-open (Kokai) No. 9-164323 and Japanese Patent Laid-open (Kokai) No. 9-173792), and crystallization (WO2008/078448 and WO2008/078646). These methods can be independently used, or can be used in an appropriate combination. When the L-amino acid is accumulated in cells of the bacterium, for example, the cells can be disrupted with ultrasonic waves or the like, a supernatant can be obtained by removing the cells from the cell-disrupted suspension by centrifugation, and the L-amino acid can be collected from the supernatant by the ion exchange resin method or the like. The L-amino acid to be collected may be a free compound, a salt thereof, or a mixture thereof. Examples of the salt can include, for example, sulfate, hydrochloride, carbonate, ammonium salt, sodium salt, and potassium salt. When L-glutamic acid is produced, L-glutamic acid to be collected may specifically be, for example, free L-glutamic acid, sodium L-glutamate (monosodium L-glutamate, MSG), ammonium L-glutamate (monoammonium L-glutamate), or a mixture of these. For example, monosodium L-glutamate (MSG) can be obtained by adding an acid to the fermentation broth to crystallize ammonium L-glutamate contained therein, and then by adding an equimolar of sodium hydroxide to the crystals. In addition, decolorization can be performed by using activated carbon before and/or after the crystallization (see, Tetsuya KAWAKITA, "Industrial Crystallization for Monosodium L-Glutamate.", Bulletin of the Society of Sea Water Science, Japan, Vol. 56:5). The monosodium L-glutamate crystal can be used as, for example, an umami seasoning. The monosodium L-glutamate crystal may also be used as a seasoning in combination with a nucleic acid such as sodium guanylate and sodium inosinate, which also have umami taste.

When the L-amino acid is precipitated in the medium, it can be collected by centrifugation, filtration, or the like. The L-amino acid precipitated in the medium may also be isolated together with the L-amino acid dissolving in the medium, after the L-amino acid dissolving in the medium is crystallized.

The collected L-amino acid may contain such components as bacterial cells, medium components, moisture, and by-product metabolites of the bacterium in addition to the L-amino acid. The collected L-amino acid may also be purified at a desired extent. Purity of the collected L-amino acid may be, for example, 50% (w/w) or higher, 85% (w/w) or higher, or 95% (w/w) or higher (JP1214636B, U.S. Pat. Nos. 5,431,933, 4,956,471, 4,777,051, 4,946,654, 5,840,358, 6,238,714, and US2005/0025878).

EXAMPLES

Hereinafter, the present invention will be more specifically explained with reference to examples. However, the present invention is not limited by these examples.

Example

Glutamic Acid Production Culture Using *Corynebacterium glutamicum* Strain Having Enhanced Expression of C4-Dicarboxylic Acid-Uptake Carrier Gene In this Example, glutamic acid production was carried out by using a glutamic acid-producing strain of *C. glutamicum* introduced with a gene encoding C4-dicarboxylic acid-uptake carrier having uptake ability for aspartic acid (Cg-dctA, Ec-dctA, Ec-dcuA, or Ec-dcuB), and the effect of an enhanced expression of the C4-dicarboxylic acid-uptake carrier gene on glutamic acid production was evaluated.

(1) Materials

Materials used in this Example are as follows.

TABLE 1

<Primers used>

| Primer | SEQ ID NO | Nucleotide Sequence (5'→3') |
|---|---|---|
| 1 | 1 | CCAAGCTTGCATGCCAGGAGGATTATAATGGATTCAAACACAGAATCTTC |
| 2 | 2 | CGGTACCCGGGGATCCTAGTGGTCTTCTTCTAACTCCAC |
| 3 | 3 | CCAAGCTTGCATGCCAGGAGGATTATAATGAAAACCTCTCTGTTTAAAGCC |
| 4 | 4 | CGGTACCCGGGGATCTTAAGAGGATAATTCGTGCG |
| 5 | 5 | CCAAGCTTGCATGCCAGGAGGATTATAATGCTAGTTGTAGAACTCATCATAG |
| 6 | 6 | CGGTACCCGGGGATCTTACAGCATGAAGCTACCCAGCACG |
| 7 | 7 | CCAAGCTTGCATGCCAGGAGGATTATAATGTTATTTACTATCCAACTTATC |
| 8 | 8 | CGGTACCCGGGGATCTTATAAGAACCCGTACATCGCGGCG |

<Plasmids Used>
pVK9 (KmR; US2006-0141588)
pVK9-Cg-dctA (KmR; present application)
pVK9-Ec-dctA (KmR; present application)
pVK9-Ec-dcuA (KmR; present application)
pVK9-Ec-dcuB (KmR; present application)

<Strains Used>
*C. glutamicum* 2256ΔsucAΔldhA yggB* (WO2014/185430)
*C. glutamicum* 2256ΔsucAΔldhA yggB*/pVK9 (present application)
*C. glutamicum* 2256ΔsucAΔldhA yggB*/pVK9-Cg-dctA (present application)
*C. glutamicum* 2256ΔsucAΔldhA yggB*/pVK9-Ec-dctA (present application)
*C. glutamicum* 2256ΔsucAΔldhA yggB*/pVK9-Ec-dcuA (present application)
*C. glutamicum* 2256ΔsucAΔldhA yggB*/pVK9-Ec-dcuB (present application)

(2) Construction of Plasmids and Strains

PCR was carried out by using genomic DNA of the *C. glutamicum* 2256 strain (ATCC 13869) as the template, and primers 1 and 2, to amplify a DNA fragment containing the dctA gene of *C. glutamicum* (Cg-dctA). The obtained DNA fragment and pVK9 (US2006-0141588) digested with BamHI and PstI were mutually ligated by using Clontech In-fusion HD Cloning Kit (TaKaRa Inc.), to construct pVK9-Cg-dctA, which is an expression plasmid of Cg-dctA.

In the same manner, PCR was carried out by using genomic DNA of the *E. coli* K-12 MG1655 strain (ATCC 47076) as the template, in combination with primers 3 and 4 to amplify a DNA fragment containing the dctA gene of *E. coli* (Ec-dctA), primers 5 and 6 to amplify a DNA fragment containing the dcuA gene of *E. coli* (Ec-dcuA), and primers 7 and 8 to amplify a DNA fragment containing the dcuB gene of *E. coli* (Ec-dcuB), and the obtained DNA fragments each were ligated with pVK9, to construct pVK9-Ec-dctA, pVK9-Ec-dcuA, and pVK9-Ec-dcuB, which are expression plasmids of those genes.

The constructed plasmids were each introduced into the *C. glutamicum* 2256ΔsucAΔldhA yggB* strain (WO2014/185430), to construct strains having an enhanced expression of the respective C4-dicarboxylic acid-uptake carrier genes. The 2256ΔsucAΔldhA yggB* strain is a glutamic acid-producing strain derived from the *C. glutamicum* 2256 strain (ATCC 13869). The 2256ΔsucAΔldhA yggB* strain is deficient in ldhA and sucA genes, and has an IS mutation (V419::IS) in yggB gene. The nucleotide sequence of this mutant yggB gene (V419::IS) and the amino acid sequence of the mutant YggB protein (V419::IS) encoded by the gene are shown in SEQ ID NOS: 11 and 12, respectively.

(3) Glutamic Acid Production Culture

Glutamic acid production culture was carried out by using each strain. The composition of a medium used is shown in Table 2.

TABLE 2

| Medium composition | |
|---|---|
| Glucose | 80 g/L |
| $(NH_4)_2SO_4$ | 30 g/L |
| $KH_2PO_4$ | 1 g/L |
| $MgSO_4 \cdot 7H_2O$ | 0.4 g/L |
| $FeSO_4 \cdot 7H_2O$ | 0.01 g/L |
| $MnSO_4 \cdot 5H_2O$ | 0.01 g/L |
| $VB_1$ | 200 μg/L |
| Biotin | 300 μg/L |
| Mameno | 0.48 g/L |
| $CaCO_3$ | 50 g/L |
| Succinic acid | 1 g/L |

The medium of the aforementioned composition adjusted to pH8.0 with KOH was prepared, and sterilized by autoclave (115° C., 10 min). The sterilized medium was added with CaCO₃ sterilized by dry heating (180° C., 6 hr) at a final concentration of 50 g/L, and used for culture.

Each strain was inoculated into 5 mL of the medium containing 50 g/L CaCO₃ contained in a large test tube, and cultured at 31.5° C. with shaking at 120 rpm by using a box shaker (ABLE ML-190). At 18 hr after start of the culture, the culture broth was sampled. The concentrations of glutamic acid and aspartic acid in the culture broth were quantified by using a Biotech-analyzer AS-310 (SAKURA SI) and an amino acid analyzer L-8800A (HITACHI), respectively.

Figure 1B:
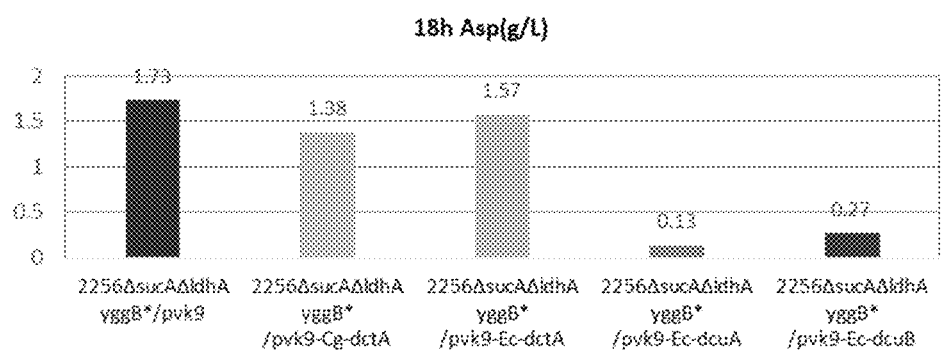
FIG. 1B shows the results of the same culture as FIG. 1A, but for the production and accumulation of aspartic acid (Asp).

Results are shown in FIGS. 1A and 1B. Accumulation of glutamic acid (Glu) was improved by an enhanced expression of Cg-dctA, Ec-dctA, Ec-dcuA, or Ec-dcuB. In addition, by-production of aspartic acid was decreased by an enhanced expression of Cg-dctA, Ec-dctA, Ec-dcuA, or Ec-dcuB.

As described above, while there has already been reported a method for producing an L-amino acid using a coryneform bacterium having an enhanced expression of dctA gene and L-glutamic acid is exemplified as an L-amino acid, it has not been demonstrated whether L-glutamic acid can be produced using the same bacterium (US2002-0106759). Rather, considering the fact that a protein encoded by dctA gene has uptake ability for L-glutamic acid (Youn et al., Characterization of the Dicarboxylate Transporter DctA in *Corynebacterium glutamicum*. Journal Of Bacteriology. 2009 September 5480-5488), a person of ordinary skill in the art should have been able to predict that an enhanced expression of dctA gene will promote uptake of L-glutamic acid into cells, and thereby the accumulation amount of L-glutamic acid in a medium can be decreased. That is, the person of ordinary skill in the art would not be able to predict that production of L-glutamic acid can be improved by an enhanced expression of dctA gene, and hence, US2002-0106759 does not substantially disclose a method for producing L-glutamic acid using a coryneform bacterium having an enhanced expression of dctA gene. In addition, for the same reason, it was difficult to enhance the expression of dctA gene for production of L-glutamic acid.

Furthermore, while a protein encoded by dctA gene has uptake ability for L-glutamic acid (Youn et al., Characterization of the Dicarboxylate Transporter DctA in *Corynebacterium glutamicum*. Journal Of Bacteriology. 2009 September 5480-5488), a protein encoded by yggB gene has excretion ability for L-glutamic acid (Nakamura et al., Mutations of the *Corynebacterium glutamicum* NCgl1221 Gene, Encoding a Mechanosensitive Channel Homolog, Induce 1-Glutamic Acid Production. Applied And Environmental Microbiology. 27 July 4491-4498). A person of ordinary skill in the art would not have been able to predict that use of dctA gene and yggB gene in combination, which have such contrary functions, is useful for production of L-glutamic acid, and hence, it was also difficult to use dctA gene and mutant yggB gene in combination for production of L-glutamic acid.

Explanation of Sequence Listing

SEQ ID NOS:

1-8: Primers

9: Nucleotide sequence of yggB gene of *Corynebacterium glutamicum* 2256 (ATCC 13869)

10: Amino acid sequence of YggB protein of *Corynebacterium glutamicum* 2256 (ATCC 13869)

11: Nucleotide sequence of mutant yggB gene (V419::IS) of *Corynebacterium glutamicum* 2256 (ATCC 13869)

12: Amino acid sequence of protein encoded by mutant yggB gene (V419::IS) of *Corynebacterium glutamicum* 2256 (ATCC 13869)

13: Nucleotide sequence of xfp gene of *Bifidobacterium longum* JCM1217

14: Amino acid sequence of Xfp protein of *Bifidobacterium longum* JCM1217

15: Nucleotide sequence of dctA gene of *Corynebacterium glutamicum* 2256 (ATCC 13869)

16: Amino acid sequence of DctA protein of *Corynebacterium glutamicum* 2256 (ATCC 13869)

17: Nucleotide sequence of dctA gene of *Escherichia coli* K-12 MG1655

18: Amino acid sequence of DctA protein of *Escherichia coli* K-12 MG1655

19: Nucleotide sequence of dcuA gene of *Escherichia coli* K-12 MG1655

20: Amino acid sequence of DcuA protein of *Escherichia coli* K-12 MG1655

21: Nucleotide sequence of dcuB gene of *Escherichia coli* K-12 MG1655

22: Amino acid sequence of DcuB protein of *Escherichia coli* K-12 MG1655

The invention claimed is:

1. A method for producing an L-amino acid, the method comprising the steps of:
   A) culturing a bacterium having an L-amino acid-producing ability in a medium resulting in accumulation of an L-amino acid in the medium; and
   B) collecting the L-amino acid from the medium;
   wherein the bacterium has been modified so that the activity of a C4-dicarboxylic acid-uptake carrier is increased as compared with a non-modified bacterium,
   wherein the C4-dicarboxylic acid-uptake carrier is a protein encoded by a gene selected from the group consisting of a dctA gene, a dcuA gene, a dcuB gene, and combinations thereof, and
   wherein the L-amino acid is an L-amino acid other than L-aspartic acid,
   provided that the L-amino acid is L-glutamic acid when the C4-dicarboxylic acid-uptake carrier is a protein encoded by a dctA gene, and
   provided that the bacterium has further been modified so as to harbor a mutant yggB gene when the bacterium is a coryneform bacterium and the C4-dicarboxylic acid-uptake carrier is a protein encoded by a dctA gene.

2. The method according to claim 1, wherein the dctA gene encodes a protein selected from the group consisting of:
   (a) a protein comprising the amino acid sequence of SEQ ID NO: 16 or 18;
   (b) a protein comprising the amino acid sequence of SEQ ID NO: 16 or 18, but which includes substitution, deletion, insertion, and/or addition of 1 to 10 amino acid residues, and wherein said protein has L-aspartic acid-uptake activity;
   (c) a protein comprising an amino acid sequence having an identity of 90% or higher to the amino acid sequence of SEQ ID NO: 16 or 18, and wherein said protein has aspartic acid-uptake activity.

3. The method according to claim 1, wherein the dcuA gene encodes a protein selected from the group consisting of:
   (a) a protein comprising the amino acid sequence of SEQ ID NO: 20;
   (b) a protein comprising the amino acid sequence of SEQ ID NO: 20, but which includes substitution, deletion, insertion, and/or addition of 1 to 10 amino acid residues, and wherein said protein has aspartic acid-uptake activity;
   (c) a protein comprising an amino acid sequence having an identity of 90% or higher to the amino acid sequence of SEQ ID NO: 20, and wherein said protein has aspartic acid-uptake activity.

4. The method according to claim 1, wherein the dcuB gene encodes a protein selected from the group consisting of:
   (a) a protein comprising the amino acid sequence of SEQ ID NO: 22;
   (b) a protein comprising the amino acid sequence of SEQ ID NO: 22, but which includes substitution, deletion, insertion, and/or addition of 1 to 10 amino acid residues, and wherein said protein has aspartic acid-uptake activity;
   (c) a protein comprising an amino acid sequence having an identity of 90% or higher to the amino acid sequence of SEQ ID NO: 22, and wherein said protein has aspartic acid-uptake activity.

5. The method according to claim 1, wherein the activity of the C4-dicarboxylic acid-uptake carrier is increased by increasing the expression of a gene encoding the C4-dicarboxylic acid-uptake carrier.

6. The method according to claim 5, wherein the expression of the gene is increased by increasing the copy number of the gene and/or modifying an expression control sequence of the gene.

7. The method according to claim 1, wherein the bacterium has further been modified so that the activity of phosphoketolase is increased as compared with a non-modified bacterium.

8. The method according to claim 7, wherein the phosphoketolase is D-xylulose-5-phosphate phosphoketolase and/or fructose-6-phosphate phosphoketolase.

9. The method according to claim 7, wherein the activity of the phosphoketolase is increased by increasing the expression of a gene encoding the phosphoketolase.

10. The method according to claim 1, wherein the bacterium is a coryneform bacterium or a bacterium belonging to the family *Enterobacteriaceae*.

11. The method according to claim 1, wherein the bacterium is a bacterium belonging to the genus *Corynebacterium*.

12. The method according to claim 11, wherein the bacterium is *Corynebacterium glutamicum*.

13. The method according to claim 1, wherein the bacterium is a bacterium belonging to the genus Pantoea or Escherichia.

14. The method according to claim 13, wherein the bacterium is *Pantoea ananatis* or *Escherichia coli*.

15. The method according to claim 1, wherein the L-amino acid is an L-amino acid of the glutamate family.

16. The method according to claim 15, wherein the L-amino acid of the glutamate family is selected from the group consisting of L-glutamic acid, L-glutamine, L-proline, L-arginine, L-citrulline, L-ornithine, and combinations thereof.

17. The method according to claim 15, wherein the L-amino acid of the glutamate family is L-glutamic acid.

18. The method according to claim 1, wherein the L-glutamic acid is monoammonium L-glutamate or monosodium L-glutamate.

19. The method according to claim 1,
   wherein the L-amino acid is an L-amino acid of glutamate family, and
   wherein the bacterium has further been modified so that the activity of α-ketoglutarate dehydrogenase and/or succinate dehydrogenase is reduced as compared with a non-modified bacterium.

20. The method according to claim 1,
wherein the bacterium is a coryneform bacterium, and
wherein the bacterium has further been modified so as to harbor a mutant yggB gene.

21. The method according to claim 20, wherein the mutant yggB gene has a mutation that imparts improved L-glutamic acid-producing ability to the coryneform bacterium.

22. The method according to claim 21, wherein the mutant yggB gene has a mutation selected from the group consisting of:
  (1) a mutation in the region coding for the amino acid residues at positions 419 to 533 of SEQ ID NO: 10,
  (2) a mutation in the region coding for a transmembrane region of SEQ ID NO: 10, and
  (3) a combination thereof.

23. The method according to claim 22, wherein the wild-type yggB gene encodes a YggB protein that is selected from the group consisting of:

(a) a protein comprising the amino acid sequence of SEQ ID NO: 10;

(b) a protein comprising the amino acid sequence of SEQ ID NO: 10, but which includes substitution, deletion, insertion, and/or addition of 1 to 10 amino acid residues, and wherein said protein, when overexpressed in the coryneform bacterium, imparts improved L-glutamic acid-producing ability to the coryneform bacterium;

(c) a protein comprising an amino acid sequence having an identity of 90% or higher to the amino acid sequence of SEQ ID NO: 10, and wherein said protein, when overexpressed in the coryneform bacterium, imparts improved L-glutamic acid-producing ability to the coryneform bacterium.

* * * * *